US011913044B2

United States Patent
Liu et al.

(10) Patent No.: US 11,913,044 B2
(45) Date of Patent: Feb. 27, 2024

(54) EVOLUTION OF CYTIDINE DEAMINASES

(71) Applicants: President and Fellows of Harvard College, Cambridge, MA (US); The Broad Institute, Inc., Cambridge, MA (US)

(72) Inventors: David R. Liu, Cambridge, MA (US); Tina Wang, Cambridge, MA (US)

(73) Assignees: President and Fellows of Harvard College, Cambridge, MA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 17/251,276

(22) PCT Filed: Jun. 14, 2019

(86) PCT No.: PCT/US2019/037216
§ 371 (c)(1),
(2) Date: Dec. 11, 2020

(87) PCT Pub. No.: WO2019/241649
PCT Pub. Date: Dec. 19, 2019

(65) Prior Publication Data
US 2021/0261938 A1    Aug. 26, 2021

Related U.S. Application Data

(60) Provisional application No. 62/685,252, filed on Jun. 14, 2018.

(51) Int. Cl.
*C12N 9/22* (2006.01)
*C12N 9/78* (2006.01)

(52) U.S. Cl.
CPC ............... *C12N 9/78* (2013.01); *C12N 9/22* (2013.01); *C12Y 305/04005* (2013.01)

(58) Field of Classification Search
None
See application file for complete search history.

(56) References Cited

U.S. PATENT DOCUMENTS

| | | |
|---|---|---|
| 5,057,432 A | 10/1991 | Wangersky et al. |
| 5,223,409 A | 6/1993 | Ladner et al. |
| 5,658,727 A | 8/1997 | Barbas et al. |
| 5,712,089 A | 1/1998 | Borrebaeck et al. |
| 5,821,047 A | 10/1998 | Garrard et al. |
| 5,880,275 A | 3/1999 | Fischhoff et al. |
| 5,965,124 A | 10/1999 | Feinberg et al. |
| 6,033,874 A | 3/2000 | Baum et al. |
| 6,156,509 A | 12/2000 | Schellenberger |
| 6,429,298 B1 | 8/2002 | Ellington et al. |
| 6,713,063 B1 | 3/2004 | Malvar et al. |
| 6,815,194 B2 * | 11/2004 | Honjo ............... C12N 9/78 435/254.2 |
| 6,962,705 B2 | 11/2005 | Malvar et al. |
| 6,969,731 B1 | 11/2005 | Tang et al. |
| 7,064,249 B2 | 6/2006 | Corbin et al. |
| 7,070,982 B2 | 7/2006 | Malvar et al. |
| 9,023,594 B2 | 5/2015 | Liu et al. |
| 9,228,207 B2 | 1/2016 | Liu et al. |
| 9,267,127 B2 | 2/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,394,537 B2 | 7/2016 | Liu et al. |
| 9,526,784 B2 | 12/2016 | Liu et al. |
| 9,567,589 B2 | 2/2017 | Jin et al. |
| 9,737,604 B2 | 8/2017 | Jin et al. |
| 9,766,216 B2 | 9/2017 | Wada et al. |
| 9,771,574 B2 | 9/2017 | Liu et al. |
| 10,179,911 B2 | 1/2019 | Liu et al. |
| 10,227,581 B2 | 3/2019 | Liu et al. |
| 10,336,997 B2 | 7/2019 | Liu et al. |
| 10,392,674 B2 | 8/2019 | Liu et al. |
| 10,597,679 B2 | 3/2020 | Liu et al. |
| 10,612,011 B2 | 4/2020 | Liu et al. |
| 10,682,410 B2 | 6/2020 | Liu et al. |

(Continued)

FOREIGN PATENT DOCUMENTS

| | | |
|---|---|---|
| EP | 0289479 A2 | 11/1988 |
| EP | 3115457 A1 | 1/2017 |

(Continued)

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Vincenzeti et al,. Protein Engineering, vol. 13, No. 11, pp. 791-799, 2000.*
Vincenzeti et al., Protein Engineering, vol. 16, No. 12, pp. 1055-1061, 2003.*
Extended European Search Report, dated Mar. 30, 2012, in connection with Application No. EP 09812363.
Extended European Search Report, dated May 26, 2017, in connection with Application No. EP 16 20 3684.
International Search Report and Written Opinion, dated Jun. 21, 2010, in connection with Application No. PCT/US2009/056194.

(Continued)

*Primary Examiner* — Richard G Hutson
(74) *Attorney, Agent, or Firm* — Wolf, Greenfield & Sacks, P.C.

(57) ABSTRACT

Some aspects of this disclosure relate to strategies, systems, methods, compositions, and kits that are useful for production (e.g., evolution) of cytidine deaminase protein variants that are characterized by increased soluble expression and/or stability relative to the wild-type cytidine deaminase protein from which they are evolved. In some embodiments, evolved cytidine deaminase variants described by the disclosure are useful for incorporation into targeted nucleic acid editing proteins, for example in fusion proteins with a Cas9 domain or variant thereof.

21 Claims, 8 Drawing Sheets

Specification includes a Sequence Listing.

(56) References Cited

U.S. PATENT DOCUMENTS

| | | |
|---|---|---|
| 10,920,208 B2 | 2/2021 | Liu et al. |
| 11,046,948 B2 | 6/2021 | Liu et al. |
| 11,078,469 B2 | 8/2021 | Liu et al. |
| 11,104,967 B2 | 8/2021 | Liu et al. |
| 11,214,792 B2 | 1/2022 | Liu et al. |
| 11,299,729 B2 | 4/2022 | Badran et al. |
| 11,447,809 B2 | 9/2022 | Bryson, Jr. et al. |
| 11,524,983 B2 | 12/2022 | Badran et al. |
| 11,624,130 B2 | 4/2023 | Liu et al. |
| 2002/0132327 A1 | 9/2002 | Hay et al. |
| 2003/0119764 A1 | 6/2003 | Loeb et al. |
| 2003/0167533 A1 | 9/2003 | Yadav et al. |
| 2003/0186292 A1 | 10/2003 | MacNeil et al. |
| 2003/0203480 A1 | 10/2003 | Kovesdi et al. |
| 2005/0019753 A1 | 1/2005 | Kukolj et al. |
| 2005/0100973 A1 | 5/2005 | Steward et al. |
| 2006/0112447 A1 | 5/2006 | Bogdanova et al. |
| 2006/0160222 A1 | 7/2006 | Rozwadowski et al. |
| 2006/0166319 A1 | 7/2006 | Chan et al. |
| 2008/0220502 A1 | 9/2008 | Schellenberger et al. |
| 2009/0215110 A1 | 8/2009 | Gibson et al. |
| 2009/0227463 A1 | 9/2009 | Reif et al. |
| 2009/0300777 A1 | 12/2009 | Nakayama |
| 2010/0297180 A1 | 11/2010 | Shone |
| 2011/0177495 A1 | 7/2011 | Liu et al. |
| 2011/0318385 A1 | 12/2011 | Jackson et al. |
| 2012/0128649 A1 | 5/2012 | Chaddock et al. |
| 2012/0190825 A1 | 7/2012 | Neumann et al. |
| 2013/0059931 A1 | 3/2013 | Petersen-Mahrt et al. |
| 2013/0117869 A1 | 5/2013 | Duchateau et al. |
| 2013/0345064 A1 | 12/2013 | Liu et al. |
| 2013/0345065 A1 | 12/2013 | Liu et al. |
| 2014/0201858 A1 | 7/2014 | Ostertag et al. |
| 2015/0056177 A1 | 2/2015 | Liu et al. |
| 2015/0259721 A1 | 9/2015 | Van Brunt et al. |
| 2015/0275202 A1 | 10/2015 | Liu et al. |
| 2016/0002301 A1 | 1/2016 | Je et al. |
| 2016/0201040 A1 | 7/2016 | Liu et al. |
| 2016/0348096 A1 | 12/2016 | Liu et al. |
| 2017/0009224 A1 | 1/2017 | Liu et al. |
| 2017/0029844 A1 | 2/2017 | Ball et al. |
| 2017/0044520 A1 | 2/2017 | Liu et al. |
| 2017/0233708 A1 | 8/2017 | Liu et al. |
| 2018/0057545 A9 | 3/2018 | Liu et al. |
| 2018/0087046 A1 | 3/2018 | Liu et al. |
| 2018/0237758 A1 | 8/2018 | Liu et al. |
| 2019/0219575 A1 | 7/2019 | Gray et al. |
| 2019/0256842 A1 | 8/2019 | Liu et al. |
| 2019/0276816 A1 | 9/2019 | Liu et al. |
| 2019/0276873 A1 | 9/2019 | Dong et al. |
| 2020/0071722 A1 | 3/2020 | Liu et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2021/0163924 A1 | 6/2021 | Packer et al. |
| 2021/0238569 A1 | 8/2021 | Liu et al. |
| 2021/0403887 A1 | 12/2021 | Liu et al. |
| 2022/0073887 A1 | 3/2022 | Liu et al. |
| 2022/0154237 A1 | 5/2022 | Liu et al. |
| 2022/0195418 A1 | 6/2022 | Liu et al. |
| 2022/0259269 A1 | 8/2022 | Liu et al. |
| 2022/0267754 A1 | 8/2022 | Liu et al. |
| 2023/0220016 A1 | 7/2023 | Liu et al. |

FOREIGN PATENT DOCUMENTS

| | | |
|---|---|---|
| JP | H0937764 A | 2/1997 |
| JP | 2011-081011 | 4/2011 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 94/18316 A2 | 8/1994 |
| WO | WO 96/04403 A1 | 2/1996 |
| WO | WO 98/32845 A1 | 7/1998 |
| WO | WO 99/23116 A1 | 5/1999 |
| WO | WO 00/71694 A1 | 11/2000 |
| WO | WO 01/05950 A2 | 1/2001 |
| WO | WO 01/61049 A1 | 8/2001 |
| WO | WO 2005/081632 A2 | 9/2005 |
| WO | WO 2007/066923 A1 | 6/2007 |
| WO | WO 2008/005529 A2 | 1/2008 |
| WO | WO 2009/082488 A2 | 7/2009 |
| WO | WO 2009/108180 A2 | 9/2009 |
| WO | WO 2010/028347 A2 | 3/2010 |
| WO | WO 2011/039518 A2 | 4/2011 |
| WO | WO 2011/125015 A2 | 10/2011 |
| WO | WO 2011/147590 A2 | 12/2011 |
| WO | WO 2011/066747 A1 | 6/2012 |
| WO | WO 2012/088381 A2 | 6/2012 |
| WO | WO 2012/138927 A2 | 10/2012 |
| WO | WO 2013/047844 A1 | 4/2013 |
| WO | WO 2014/039585 A2 | 3/2014 |
| WO | WO 2014/157820 A1 | 10/2014 |
| WO | WO 2014/158593 A1 | 10/2014 |
| WO | WO 2015/134121 A2 | 9/2015 |
| WO | WO 2015/193897 A1 | 12/2015 |
| WO | WO 2016/077052 A9 | 5/2016 |
| WO | WO 2016/168631 A1 | 10/2016 |
| WO | WO 2017/015559 A2 | 1/2017 |
| WO | WO 2017/070632 A2 | 4/2017 |
| WO | WO 2017/136792 A2 | 8/2017 |
| WO | WO 2018/009903 A2 | 1/2018 |
| WO | WO 2018/027078 A1 | 2/2018 |
| WO | WO 2018/039438 A1 | 3/2018 |
| WO | WO 2018/109447 A1 | 6/2018 |
| WO | WO 2018/119042 A1 | 6/2018 |
| WO | WO 2018/136939 A1 | 7/2018 |
| WO | WO 2019/040935 A1 | 2/2019 |
| WO | WO 2019/067815 A2 | 4/2019 |
| WO | WO 2019/118362 A1 | 6/2019 |
| WO | WO 2020/204836 A1 | 10/2020 |

OTHER PUBLICATIONS

International Preliminary Report on Patentability, dated Mar. 17, 2011, in connection with Application No. PCT/US2009/056194.
Extended European Search Report, dated May 16, 2017, in connection with Application No. EP 17 16 0955.
Invitation to Pay Additional Fees, dated Aug. 30, 2012, in connection with Application No. PCT/US2011/066747.
International Search Report and Written Opinion, dated Oct. 30, 2012, in connection with Application No. PCT/US2011/066747.
International Preliminary Report on Patentability, dated Jul. 4, 2013, in connection with Application No. PCT/US2011/066747.
International Search Report and Written Opinion, dated Jan. 30, 2015, in connection with Application No. PCT/US2014/052231.
International Preliminary Report on Patentability, dated Mar. 3, 2016, in connection with Application No. PCT/US2014/052231.
International Search Report and Written Opinion, dated Sep. 25, 2015, in connection with Application No. PCT/US2015/012022.
International Preliminary Report on Patentability, dated Aug. 4, 2016, in connection with Application No. PCT/US2015/012022.
Invitation to Pay Additional Fees, dated Jan. 12, 2017, in connection with Application No. PCT/US/2016/043559.
International Search Report and Written Opinion, dated Mar. 10, 2017, in connection with Application No. PCT/US/2016/043559.
International Preliminary Report on Patentability, dated Feb. 1, 2018, in connection with Application No. PCT/US/2016/043559.
International Search Report and Written Opinion, dated Jun. 10, 2016, in connection with Application No. PCT/US2015/057012.
International Preliminary Report on Patentability, dated May 4, 2017, in connection with Application No. PCT/US2015/057012.
International Search Report and Written Opinion, dated Aug. 11, 2016, in connection with Application No. PCT/US2016/027795.

(56) References Cited

OTHER PUBLICATIONS

International Preliminary Report on Patentability, dated Oct. 26, 2017, in connection with Application No. PCT/US2016/027795.
Invitation to Pay Additional Fees, dated Oct. 12, 2016, in connection with Application No. PCT/US2016/044546.
International Search Report and Written Opinion, dated Dec. 28, 2016, in connection with Application No. PCT/US2016/044546.
International Preliminary Report on Patentability, dated Feb. 8, 2018, in connection with Application No. PCT/US/2016/044546.
International Search Report and Written Opinion, dated Nov. 30, 2016, in connection with Application No. PCT/US2016/043513.
International Preliminary Report on Patentability, dated Feb. 1, 2018, in connection with Application No. PCT/US2016/043513.
Invitation to Pay Additional Fees, dated Apr. 5, 2018, in connection with Application No. PCT/US2018/14867.
International Search Report and Written Opinion, dated May 23, 2018, in connection with Application No. PCT/US2018/14867.
International Preliminary Report on Patentability, dated Aug. 1, 2019, in connection with Application No. PCT/US2018/14867.
Invitation to Pay Additional Fees, dated Sep. 12, 2018, in connection with Application No. PCT/US2018/040692.
International Search Report and Written Opinion, dated Nov. 15, 2018, in connection with Application No. PCT/US2018/040692.
International Preliminary Report on Patentability, dated Jan. 16, 2020, in connection with Application No. PCT/US2018/040692.
Invitation to Pay Additional Fees, dated Jan. 4, 2019, in connection with Application No. PCT/US2018/051557.
International Search Report and Written Opinion, dated Feb. 25, 2019, in connection with Application No. PCT/US2018/051557.
International Preliminary Report on Patentability, dated Apr. 2, 2020, in connection with Application No. PCT/US2018/051557.
International Search Report and Written Opinion, dated Nov. 21, 2018, in connection with Application No. PCT/US2018/044242.
International Search Report and Written Opinion, dated Sep. 4, 2019, in connection with Application No. PCT/US2019/037216.
International Preliminary Report on Patentability, dated Dec. 24, 2020, in connection with Application No. PCT/US2019/037216.
Invitation to Pay Additional Fees, dated Nov. 19, 2018, in connection with Application No. PCT/US18/48134.
International Search Report and Written Opinion, dated Jan. 22, 2019, in connection with Application No. PCT/US18/48134.
International Preliminary Report on Patentability, dated Mar. 5, 2020, in connection with Application No. PCT/US18/48134.
Invitation to Pay Additional Fees, dated Oct. 13, 2020, in connection with Application No. PCT/US2020/042016.
International Search Report and Written Opinion, dated Dec. 10, 2020, in connection with Application No. PCT/US2020/042016.
[No Author Listed] Genbank Submission. NCBI; Accession No. WP_010869888, version WP_010869888.1. tyrosine—tRNA ligase [Methanocaldococcus jannaschii]. Jun. 1, 2019.
[No Author Listed] NCBI Accession No. XP_015843220.1. C→U editing enzyme APOBEC-1 [Peromyscus maniculatus bairdii], XP002793540.
[No Author Listed] NCBI Accession No. XP_021505673.1. C→U editing enzyme APOBEC-1 [Meriones unguiculatus], XP002793541.
Genbank Submission. NCBI; Accession No. WP_011033391, version WP_011033391.1. pyrrolysine—tRNA(Pyl) ligase [Methanosarcina mazei]. Polycarpo et al.; Nov. 29, 2019.
Genbank Submission. NCBI; Accession No. WP_011305865, version WP_011305865.1. pyrrolysine—tRNA(Pyl) ligase [Methanosarcina barkeri].Polycarpo et al.; Nov. 29, 2019.
Agarwal et al., Mode of VAMP substrate recognition and inhibition of Clostridium botulinum neurotoxin F. Nat Struct Mol Biol. Jul. 2009;16(7):789-94. doi: 10.1038/nsmb.1626. Epub Jun. 21, 2009.
Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.

Akopian et al., Chimeric recombinases with designed DNA sequence recognition. Proc Natl Acad Sci U S A. Jul. 22, 2003;100(15):8688-91. Epub Jul. 1, 2003.
Amiram et al., Evolution of translation machinery in recoded bacteria enables multi-site incorporation of nonstandard amino acids. Nat Biotechnol. Dec. 2015;33(12):1272-1279. doi: 10.1038/nbt.3372. Epub Nov. 16, 2015.
Armstrong et al., Chapter 3. Vectors for Phage Display. In: Phage Display of Peptides and Proteins. Kay et al., eds. Academic Press. San Diego, CA. 1996:35-53.
Bade et al., Botulinum neurotoxin type D enables cytosolic delivery of enzymatically active cargo proteins to neurones via unfolded translocation intermediates. J Neurochem. Dec. 2004;91(6):1461-72.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennett et al., Unlocking of the filamentous bacteriophage virion during infection is mediated by the C domain of pIII. J Mol Biol. Feb. 17, 2006;356(2):266-73. Epub Dec. 9, 2005.
Binz et al., Clostridial neurotoxins: mechanism of SNARE cleavage and outlook on potential substrate specificity reengineering. Toxins. Apr. 2010;2(4):665-82. Epub Apr. 13, 2010.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.
Boch et al., Breaking the code of DNA binding specificity of TAL-type III effectors. Science. Dec. 11, 2009;326(5959):1509-12. doi: 10.1126/science.1178811.
Boeke et al., Effects of bacteriophage f1 gene III protein on the host cell membrane. Mol Gen Genet. 1982;186(2):185-92.
Boersma et al., Selection strategies for improved biocatalysts. FEBS J. May 2007;274(9):2181-95.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Box et al., A multi-domain protein system based on the HC fragment of tetanus toxin for targeting DNA to neuronal cells. J Drug Target. Jul. 2003;11(6):333-43. doi: 10.1080/10611863100010634667.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23, 2002;41(16):5144-9.
Buchholz et al., Alteration of Cre recombinase site specificity by substrate-linked protein evolution. Nat Biotechnol. Nov. 2001;19(11):1047-52.
Cadwell et al., Randomization of Genes by PCR Mutagenesis. PCR Methods Applic. 1992;2:28-33.
Camps et al., Targeted gene evolution in Escherichia coli using a highly error-prone DNA polymerase I. Proc Natl Acad Sci U S A. Aug. 19, 2003;100(17):9727-32. Epub Aug. 8, 2003.
Canitrot et al., Overexpression of DNA polymerase beta in cell results in a mutator phenotype and a decreased sensitivity to anticancer drugs. Proc Natl Acad Sci U S A. Oct. 13, 1998;95(21):12586-90. doi: 10.1073/pnas.95.21.12586.

(56) References Cited

OTHER PUBLICATIONS

Cao et al., Characterization of the transgenic rice event TT51-1 and construction of a reference plasmid. J Agric Food Chem. Aug. 24, 2011;59(16):8550-9. doi: 10.1021/jf201699s. Epub Jul. 21, 2011.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Cattaneo et al., SEL1L affects human pancreatic cancer cell cycle and invasiveness through modulation of PTEN and genes related to cell-matrix interactions. Neoplasia. 2005;7(11):1030-1038.
Chaddock et al., Inhibition of vesicular secretion in both neuronal and nonneuronal cells by a retargeted endopeptidase derivative of Clostridium botulinum neurotoxin type A. Infect. Immun. May 2000;68(5):2587-93.
Chaineau et al., Multiple roles of the vesicular-SNARE TI-VAMP in post-Golgi and endosomal trafficking. FEBS Letters. Oct. 2009;583:3817-26.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase-promoter complex. Nature. May 6, 1999;399(6731):80-3.
Chen et al., Information theory based T7-like promoter models: classification of bacteriophages and differential evolution of promoters and their polymerases. Nucleic Acids Res. Oct. 31, 2005;33(19):6172-87. Print 2005.
Chen, Clinical uses of botulinum neurotoxins: current indications, limitations and future developments. Toxins (Basel). 2012;4(10):913-939.
Chen et al., Engineering botulinum neurotoxin to extend therapeutic intervention. PNAS. Jun. 2009;106(23):9180-4.
Chen et al., SNARE-mediated membrane fusion. Nat Rev Mol Cell Biol. Feb. 2001;2(2):98-106.
Chen et al., VAMP8 facilitates cellular proliferation and temozolomide resistance in human glioma cells. Neuro-Oncology. 2015;17(3):407-18. Epub Sep. 10, 2014.
Chin, Expanding and reprogramming the genetic code of cells and animals. Annu Rev Biochem. 2014;83:379-408. doi: 10.1146/annurev-biochem-060713-035737. Epub Feb. 10, 2014.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Clackson et al., Making antibody fragments using phage display libraries. Nature. Aug. 15, 1991;352(6336):624-8.
Click et al., Filamentous phage infection: required interactions with the TolA protein. J Bacteriol. Oct. 1997;179(20):6464-71.
Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.
Cong et al., Multiplex genome engineering using CRISPR/Cas systems. Science. 2013; 339:819-23.
Corey et al., Trypsin display on the surface of bacteriophage. Gene. Jun. 15, 1993;128(1):129-34.
Crameri et al., Display of biologically active proteins on the surface of filamentous phages: a cDNA cloning system for selection of functional gene products linked to the genetic information responsible for their production. Gene. Dec. 27, 1993;137(1):69-75.
Craik et al., Proteases as therapeutics. Biochem J. Apr. 2011;435(1):16 pages.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.

Datsenko et al., One-step inactivation of chromosomal genes in Escherichia coli K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 25, 1999;274(26):18218-30.
Deltcheva et al., CRISPR RNA maturation by trans-encoded small RNA and host factor RNase III. Nature. Mar. 31, 2011;471(7340):602-7. doi: 10.1038/nature09886.
Deribe, Mechanistic insights into the role of truncating PREX2 mutations in melanoma. Mol Cell Oncol. 2016;3(3):e1160174.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dicarlo et al., Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.
Dickinson et al., A system for the continuous directed evolution of proteases rapidly reveals drug-resistance mutations. Nat Commun. Oct. 30, 2014;5:5352. doi: 10.1038/ncomms6352.
Dickinson et al., Experimental interrogation of the path dependence and stochasticity of protein evolution using phage-assisted continuous evolution. Proc Natl Acad Sci USA. May 2013;110(22):9007-12.
Dove et al., Conversion of the omega subunit of Escherichia coli RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Drake, A constant rate of spontaneous mutation in DNA-based microbes. Proc Natl Acad Sci U S A. Aug. 15, 1991;88(16):7160-4.
Duggan et al., Inhibition of Release of Neurotransmitters from Rat Dorsal Root Ganglia by a Novel Conjugate of a Clostridium botulinum Toxin A Endopeptidase Fragment and Erythrina cristagalli Lectin. The Journal of Biological Chemistry. Sep. 2002;277(38):34846-52.
Durai et al., A bacterial one-hybrid selection system for interrogating zinc finger-DNA interactions. Comb Chem High Throughput Screen. May 2006;9(4):301-11.
Durniak et al., The structure of a transcribing T7 RNA polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. Epub Apr. 10, 2011.
Fan et al., Rationally evolving tRNAPyl for efficient incorporation of noncanonical amino acids. Nucleic Acids Res. Dec. 15, 2015;43(22):e156. doi: 10.1093/nar/gkv800. Epub Aug. 6, 2015.
Feng et al., Exo1: A new chemical inhibitor of the exocytic pathway. PNAS. May 2003;100(11):6469-74.
Ferretti et al., Complete genome sequence of an M1 strain of Streptococcus pyogenes. Proc Natl Acad Sci U S A. Apr. 10, 2001;98(8):4658-63. doi: 10.1073/pnas.071559398.
Fijalkowska et al., Mutants in the Exo I motif of Escherichia coli dnaQ: defective proofreading and inviability due to error catastrophe. Proc Natl Acad Sci U S A. Apr. 2, 1996;93(7):2856-61.
Foster et al., Re-engineering the target specificity of Clostridial neurotoxins—A route to novel therapeutics. Neurotoxicity Research. May 2006;9(2,3):101-7.
Foster et al., Targeted Secretion Inhibitors—Innovative Protein Therapeutics. Toxins. Dec. 2010;2:2795-815.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fu et al., Promises and Pitfalls of Intracellular Delivery of Proteins. Bioconjugate Chemistry. Aug. 2014;25:1602-8.
Fuchs et al., Targeting Recombinant Antibodies to the Surface of Escherichia coli: Fusion to a Peptidoglycan Associated Lipoprotein. Bio/Technology. 1991;9:1370-72.

(56) References Cited

OTHER PUBLICATIONS

Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Garrard et al., Fab assembly and enrichment in a monovalent phage display system. Biotechnology (N Y). Dec. 1991;9(12):1373-7.
Gibson et al., Enzymatic assembly of DNA molecules up to several hundred kilobases. Nat Methods. May 2009;6(5):343-5. Epub Apr. 12, 2009.
Gill, Bacterial Toxins: a Table of Letal Amounts. Microbiological Reviews. Mar. 1982;46(1):86-94.
Goodnough et al., Development of a delivery vehicle for intracellular transport of botulinum neurotoxin antagonists. FEBS Lett. Feb. 27, 2002;513(2-3):163-8.
Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993;12(2):725-34.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat. Biotechnol. 2014; 32(6): 577-82. doi: 10.1038/nbt.2909. Epub Apr. 25, 2014.
Guo et al., Evolution of amber suppressor tRNAs for efficient bacterial production of proteins containing nonnatural amino acids. Angew Chem Int Ed Engl. 2009;48(48):9148-51. doi: 10.1002/anie.200904035.
Guo et al., Polyspecific pyrrolysyl-tRNA synthetases from directed evolution. Proc Natl Acad Sci U S A. Nov. 25, 2014;111(47):16724-9. doi: 10.1073/pnas.1419737111. Epub Nov. 10, 2014.
Guzman et al., Tight regulation, modulation, and high-level expression by vectors containing the arabinose PBAD promoter. J Bacteriol. 1995;177(14):4121-4130.
Harris et al., Measurement of enzyme activity. Methods Enzymol. 2009;463:57-71.
Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and *Escherichia coli* expression of a human IgM Fab. Hum Antibodies Hybridomas. Apr. 1992;3(2):81-5.
Hedstrom et al., Converting trypsin to chymotrypsin: the role of surface loops. Science. Mar. 1992;255(5049):1249-53.
Hendricks et al., The S. cerevisiae Mag1 3-methyladenine DNA glycosylase modulates susceptibility to homologous recombination. DNA Repair (Amst). 2002;1(8):645-659.
Herring et al., The amino-terminal domain of pyrrolysyl-tRNA synthetase is dispensable in vitro but required for in vivo activity. FEBS Lett. Jul. 10, 2007;581(17):3197-203. doi: 10.1016/j.febslet.2007.06.004. Epub Jun. 12, 2007.
Ho et al., Recombinant botulinum neurotoxin A heavy chainbased delivery vehicles for neuronal cell targeting. Protein Engineering, Design & Selection. 2011;24(3):247-53. Epub Nov. 4, 2010.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Hu et al., *Escherichia coli* one- and two-hybrid systems for the analysis and identification of protein-protein interactions. Methods. Jan. 2000;20(1):80-94.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. With Supplementary Information.
Huse et al., Generation of a large combinatorial library of the immunoglobulin repertoire in phage lambda. Science. Dec. 8, 1989;246(4935):1275-81.
Husimi et al., Cellstat—a continuous culture system of a bacteriophage for the study of the mutation rate and the selection process of the DNA level. Rev Sci Instrum. Apr. 1982;53(4):517-22.
Husimi, Selection and evolution of bacteriophages in cellstat. Adv Biophys. 1989;25:1-43.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.
Ikeda et al., In vivo and in vitro activities of point mutants of the bacteriophage T7 RNA polymerase promoter. Biochemistry. Sep. 22, 1992;31(37):9073-80.
Ikeda et al., Selection and characterization of a mutant T7 RNA polymerase that recognizes an expanded range of T7 promoter-like sequences. Biochemistry. Sep. 7, 1993;32(35):9115-24.
Imburgio et al., Studies of promoter recognition and start site selection by T7 RNA polymerase using a comprehensive collection of promoter variants. Biochemistry. Aug. 29, 2000;39(34):10419-30.
Irion et al., Identification and targeting of the ROSA26 locus in human embryonic stem cells. Nat Biotechnol. Dec. 2007;25(12):1477-82. Epub Nov. 25, 2007.
Jankovic et al., Direct selection and phage display of a Gram-positive secretome. Genome Biology. Dec. 13, 2007; 8(266):1-15.
Jiang et al., PylSn and the homologous N-terminal domain of pyrrolysyl-tRNA synthetase bind the tRNA that is essential for the genetic encoding of pyrrolysine. J Biol Chem. Sep. 21, 2012;287(39):32738-46. doi: 10.1074/jbc.M112.396754. Epub Jul. 31, 2012.
Jiang et al., RNA guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Joung et al., A bacterial two-hybrid selection system for studying protein-DNA and protein-protein interactions. Proc Natl Acad Sci U S A. Jun. 20, 2000;97(13):7382-7.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kavran et al., Structure of pyrrolysyl-tRNA synthetase, an archaeal enzyme for genetic code innovation. Proc Natl Acad Sci U S A. Jul. 3, 2007;104(27):11268-73. doi: 10.1073/pnas.0704769104. Epub Jun. 25, 2007.

(56) References Cited

OTHER PUBLICATIONS

Kawarasaki et al., Enhanced crossover SCRATCHY: construction and high-throughput screening of a combinatorial library containing multiple non-homologous crossovers. Nucleic Acids Res. Nov. 1, 2003;31(21):e126.

Khlebnikov et al., Modulation of gene expression from the arabinose-inducible araBAD promoter. J Ind Microbiol Biotechnol. Jul. 2002;29(1):34-7.

Kim et al., DJ-1, a novel regulator of the tumor suppressor PTEN. Cancer Cell. 2005;7(3):263-273.

Kim et al., Increasing the genome-targeting scope and precision of base editing with engineered Cas9-cytidine deaminase fusions. Nature Biotechnology; Feb. 13, 2007; 35(4): 371-376.

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Köhler, A yeast-based growth assay for the analysis of site-specific proteases. Nucleic Acids Res. 2003;31(4):e16. 5 pages.

Komor et al., Programmable editing of a target base in genomic DNA without double-stranded DNA cleavage. Nature. May 19, 2016;533(7603):420-4. doi: 10.1038/nature17946. Epub Apr. 20, 2016.

Kozak et al., Structural features in eukaryotic mRNAs that modulate the initiation of translation. J Biol Chem. Oct. 25, 1991;266(30):19867-70.

Kuzmine et al., Binding of the priming nucleotide in the initiation of transcription by T7 RNA polymerase. J Biol Chem. Jan. 31, 2003;278(5):2819-23. Epub Nov. 9, 2002.

Laskowska et al., IbpA and IbpB, the new heat-shock proteins, bind to endogenous *Escherichia coli* proteins aggregated intracellularly by heat shock. Biochimie. 1996;78(2):117-22.

Latimer et al., Specificity of monoclonal antibodies produced against phosphorothioate and ribo modified DNAs. Mol Immunol. Oct. 1995;32(14-15):1057-64.

Lebeda et al., The Zinc-Dependent Protease Activity of the Botulinum Neurotoxins. Toxins. May 2010;2:978-97.

Leconte et al., A population-based experimental model for protein evolution: effects of mutation rate and selection stringency on evolutionary outcomes. Biochemistry. Feb. 26, 2013;52(8): 1490-1499.

Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.

Lincoln et al., Self-sustained replication of an RNA enzyme. Science. Feb. 27, 2009;323(5918):1229-32. Epub Jan. 8, 2009.

Lindemann et al., Evolution of bacteriophage in continuous culture: a model system to test antiviral gene therapies for the emergence of phage escape mutants. J Virol. Jun. 2002;76(11):5784-92.

Liu et al., Adding new chemistries to the genetic code. Annu Rev Biochem. 2010;79:413-44. doi: 10.1146/annurev.biochem.052308.105824.

Lu, The destructive effect of botulinum neurotoxins on the SNARE protein: SNAP-25 and synaptic membrane fusion. PeerJ. 2015;3:e1065. Published Jun. 30, 2015.

Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19. doi: 10.1074/jbc.272.34.21408.

Lutz et al., Creating multiple-crossover DNA libraries independent of sequence identity. Proc Natl Acad Sci U S A. Sep. 25, 2001;98(20):11248-53. Epub Sep. 18, 2001.

Maeder et al., Robust, synergistic regulation of human gene expression using TALE activators. Nat Methods. Mar. 2013;10(3):243-5. doi: 10.1038/nmeth.2366. Epub Feb. 10, 2013.

Makeyev et al., Evolutionary potential of an RNA virus. J Virol. Feb. 2004;78(4):2114-20.

Mali et al., RNA-guided human genome engineering via Cas9. Science. 2013; 339:823-26.

Malmborg et al., Selective phage infection mediated by epitope expression on F pilus. J Mol Biol. Oct. 31, 1997;273(3):544-51.

Marcet-Palacios et al., Vesicle-associated membrane protein 7 (VAMP-7) is essential for target cell killing in a natural killer cell line. Biochem Biophys Res Commun. Feb. 15, 2008;366(3):617-23. doi: 10.1016/j.bbrc.2007.11.079. Epub Nov. 26, 2007.

Martin et al., Kinetic analysis of T7 RNA polymerase-promoter interactions with small synthetic promoters. Biochemistry. May 19, 1987;26(10):2690-6.

Masuyer et al., Engineered botulinum neurotoxins as new therapeutics. Annu Rev Pharmacol Toxicol. 2014;54:27-51.

McCafferty et al., Phage antibodies: filamentous phage displaying antibody variable domains. Nature. Dec. 6, 1990;348(6301):552-4.

McConnell et al., Constrained peptide libraries as a tool for finding mimotopes. Gene. Dec. 30, 1994;151(1-2):115-8.

McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

Mihai et al., PTEN inhibition improves wound healing in lung epithelia through changes in cellular mechanics that enhance migration. Am J Physiol Lung Cell Mol Physiol. 2012;302(3):L287-L299.

Miller et al., A TALE nuclease architecture for efficient genome editing. Nat Biotechnol. Feb. 2011;29(2):143-8. doi:10.1038/nbt.1755. Epub Dec. 22, 2010.

Milligan et al., Oligoribonucleotide synthesis using T7 RNA polymerase and synthetic DNA templates. Nucleic Acids Res. Nov. 11, 1987;15(21):8783-98.

Mills et al., An extracellular Darwinian experiment with a self-duplicating nucleic acid molecule. Proc Natl Acad Sci U S A. Jul. 1967;58(1):217-24.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Nelson et al., Filamentous phage DNA cloning vectors: a noninfective mutant with a nonpolar deletion in gene III. Virology. Jan. 30, 1981;108(2):338-50.

Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.

Nozawa et al., Pyrrolysyl-tRNA synthetase-tRNA(Pyl) structure reveals the molecular basis of orthogonality. Nature. Feb. 26, 2009;457(7233):1163-7. doi: 10.1038/nature07611. Epub Dec. 31, 2008.

O'Donoghue et al., Upgrading protein synthesis for synthetic biology. Nat Chem Biol. Oct. 2013;9(10):594-8. doi: 10.1038/nchembio.1339.

O'Maille et al., Structure-based combinatorial protein engineering (SCOPE). J Mol Biol. Aug. 23, 2002;321(4):677-91.

Oeemig et al., Solution structure of DnaE intein from Nostoc punctiforme: structural basis for the design of a new split intein suitable for site-specific chemical modification. FEBS Lett. May 6, 2009;583(9):1451-6.

Opperman et al., A model for a umuDC-dependent prokaryotic DNA damage checkpoint. Proc Natl Acad Sci U S A. Aug. 3, 1999;96(16):9218-23.

Ostendorf et al., Characterization of a dam mutant of Serratia marcescens and nucleotide sequence of the dam region. J Bacteriol. Jul. 1999;181(13):3880-5.

Ostermeier et al., A combinatorial approach to hybrid enzymes independent of DNA homology. Nat Biotechnol. Dec. 1999;17(12):1205-9.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Pickett et al., Towards New Uses of Botulinum Toxin as a Novel Therapeutic Tool. Toxins. Jan. 2011;3:63-81.

Pogson et al., Engineering Next Generation Proteases. Curr Opin Biotechnol. Aug. 2009;20(4):390-7.

(56) References Cited

OTHER PUBLICATIONS

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46. doi: 10.1006/jmbi.1999.2605.
Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.
Rakonjac et al., Filamentous phage are released from the bacterial membrane by a two-step mechanism involving a short C-terminal fragment of pIII. J Mol Biol. Jun. 25, 1999;289(5):1253-65.
Rakonjac et al., Filamentous phage infection-mediated gene expression: construction and propagation of the gIII deletion mutant helper phage R408d3. Gene. Oct. 1, 1997;198(1-2):99-103.
Rakonjac et al., Roles of pIII in filamentous phage assembly. J Mol Biol. Sep. 11, 1998;282(1):25-41.
Raskin et al., Substitution of a single bacteriophage T3 residue in bacteriophage T7 RNA polymerase at position 748 results in a switch in promoter specificity. J Mol Biol. Nov. 20, 1992;228(2):506-15.
Raskin et al., T7 RNA polymerase mutants with altered promoter specificities. Proc Natl Acad Sci U S A. Apr. 15, 1993;90(8):3147-51.
Rawlings et al., MEROPS: the database of proteolytic enzymes, their substrates and inhibitors. Nucleic Acids Res. Jan. 2014;42(Database issue):D503-9.
Rebar et al., Phage display methods for selecting zinc finger proteins with novel DNA-binding specificities. Methods Enzymol. 1996;267:129-49.
Reidhaar-Olson et al., Random mutagenesis of protein sequences using oligonucleotide cassettes. Methods Enzymol. 1991;208:564-86.
Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.
Riechmann et al., The C-terminal domain of TolA is the coreceptor for filamentous phage infection of *E. coli*. Cell. Jul. 25, 1997;90(2):351-60.
Ringquist et al., Translation initiation in *Escherichia coli:* sequences within the ribosome-binding site. Mol Microbiol. May 1992;6(9):1219-29.
Rosenberg et al., T7 Select® Phage Display System: A Powerful new protein display system based on bacteriophage T7. Innovations. 1996;6:1-6.
Rossetto et al., Botulinum neurotoxins: genetic, structural and mechanistic insights. Nat Rev Microbiol. Aug. 2014;12(8):535-49. doi: 10.1038/nrmicro3295. Epub Jun. 30, 2014.
Santini et al., Efficient display of an HCV cDNA expression library as C-terminal fusion to the capsid protein D of bacteriophage lambda. J Mol Biol. Sep. 11, 1998;282(1):125-35.
Santoro et al., Directed evolution of the site specificity of Cre recombinase. Proc Natl Acad Sci U S A. Apr. 2, 2002;99(7):4185-90. Epub Mar. 19, 2002.
Schultz et al., Oligo-2'-fluoro-2'-deoxynucleotide N3'-->P5' phosphoramidates: synthesis and properties. Nucleic Acids Res. Aug. 1, 1996;24(15):2966-73.
Scott et al., Searching for peptide ligands with an epitope library. Science. Jul. 27, 1990;249(4967):386-90.
Sices et al., A genetic screen for the isolation and characterization of site-specific proteases. Proc Natl Acad Sci U S A. Mar. 17, 1998;95(6):2828-33.
Sices et al., Rapid genetic selection of inhibitor-resistant protease mutants: clinically relevant and novel mutants of the HIV protease. AIDS Res Hum Retroviruses. Sep. 1, 2001;17(13):1249-55.
Sieber et al., Libraries of hybrid proteins from distantly related sequences. Nat Biotechnol. May 2001;19(5):456-60.

Sikorra et al., Substrate Recognition Mechanism of VAMP/Synaptobrevin-cleaving Clostridial Neurotoxins. Journal of Biological Chemistry. 2008;283:21145-52. Epub May 29, 2008.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Smith, Filamentous fusion phage: novel expression vectors that display cloned antigens on the virion surface. Science. Jun. 14, 1985;228(4705):1315-7.
Somm et al., A botulinum toxin—drived targeted secretion inhibitor downregulates the GH/IGF1 axis. The Journal of Clinical Investigation. Sep. 2012;122(9):3295-306.
Steffen et al., MT1-MMP-Dependent Invasion is Regulated by TI-VAMP/VAMP7. Current Biology. Jun. 2008;18:926-31.
Stemmer, Rapid evolution of a protein in vitro by DNA shuffling. Nature. Aug. 4, 1994;370(6488):389-91.
Sutter et al., Non-replicating vaccinia vector efficiently expresses bacteriophage T7 RNA polymerase. FEBS Lett. Aug. 28, 1995;371(1):9-12.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tsai et al., Targeting botulinum neurotoxin persistence by the ubiquitin-proteasome system. PNAS. Sep. 2010;107(38):16554-9.
Tsuji et al., Random multi-recombinant PCR for the construction of combinatorial protein libraries. Nucleic Acids Res. Oct. 15, 2001;29(20):E97.
Turner et al., Structural plasticity of an aminoacyl-tRNA synthetase active site. Proc Natl Acad Sci U S A. Apr. 25, 2006;103(17):6483-8. doi: 10.1073/pnas.0601756103. Epub Apr. 17, 2006.
Tzagoloff et al., The Initial Steps in Infection With Coliphage M13. Virology. Nov. 1964;24:372-80.
Umehara et al., N-acetyl lysyl-tRNA synthetases evolved by a CcdB-based selection possess N-acetyl lysine specificity in vitro and in vivo. FEBS Lett. Mar. 23, 2012;586(6):729-33. doi: 10.1016/j.febslet.2012.01.029. Epub Jan. 28, 2012.
Varadarajan et al., Engineering of protease variants exhibiting high catalytic activity and exquisite substrate selectivity. PNAS. May 2005;102(19):6855-60.
Varadarajan et al., Highly active and selective endopeptidases with programmed substrate specificities. Nat Chem Biol. May 2008;4(5):290-4.
Vidal et al., Yeast forward and reverse 'n'-hybrid systems. Nucleic Acids Res. Feb. 15, 1999;27(4):919-29.
Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.
Wang et al., Continuous directed evolutions of proteins with improved soluble expression. Nature Chemical Biology. Nat Publishing Group. Aug. 20, 2018; 14(10):972-980.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Wang et al., Syntaxin Requirement for Ca2+-Triggered Exocytosis in Neurons and Endocrine Cells Demonstrated with an Engineered Neurotoxin. Boiochemistry. Apr. 2011;50(14):2711-3.
Webb et al., Production of catalytically inactive BoNT/A1 holoprotein and comparison with BoNT/A1 subunit vaccines against toxin subtypes A1, A2, and A3. Vaccine. 2009;27(33):4490-4497.

(56) References Cited

OTHER PUBLICATIONS

Wharton et al., A new-specificity mutant of 434 repressor that defines an amino acid-base pair contact. Nature. Apr. 30-May 6, 1987;326(6116):888-91.

Wharton et al., Changing the binding specificity of a repressor by redesigning an alpha-helix. Nature. Aug. 15-21, 1985;316(6029):601-5.

Williams et al., SNAP23, Syntaxin4, and vesicle-associated membrane protein 7 (VAMP7) mediate trafficking of membrane type 1-matrix metalloproteinase (MT1-MMP) during invadopodium formation and tumor cell invasion. MBoC. Jul. 2014;25:2061-70.

Wright et al., Continuous in vitro evolution of catalytic function. Science. Apr. 25, 1997;276(5312):614-7.

Yamamoto et al., Virological and immunological bases for HIV-1 vaccine design. Uirusu 2007;57(2):133-139. https://doi.org/10.2222/jsv.57.133.

Yanagisawa et al., Crystallographic studies on multiple conformational states of active-site loops in pyrrolysyl-tRNA synthetase. J Mol Biol. May 2, 2008;378(3):634-52. doi: 10.1016/j.jmb.2008.02.045. Epub Feb. 29, 2008.

Yanagisawa et al., Multistep engineering of pyrrolysyl-tRNA synthetase to genetically encode N(epsilon)-(o-azidobenzyloxycarbonyl) lysine for site-specific protein modification. Chem Biol. Nov. 24, 2008;15(11):1187-97. doi: 10.1016/j.chembiol.2008.10.004.

Yeh et al., Retargeted Clostridial neurotoxins as Novel Agents for Treating Chronic Diseases. Biochemistry. Nov. 2011;50:10419-21.

Yi et al., Engineering of TEV protease variants by yeast ER sequestration screening (YESS) of combinatorial libraries. PNAS. Apr. 2013;110(18):7229-34.

Yuan et al., Laboratory-directed protein evolution. Microbiol Mol Biol Rev. Sep. 2005;69(3):373-92.

Zhou et al., Optimization of the Tet-On system for regulated gene expression through viral evolution. Gene Ther. Oct. 2006;13(19):1382-90. Epub May 25, 2006.

Ziemann et al., Gene name errors are widespread in the scientific literature. Genome Biol. Aug. 23, 2016;17(1):177. doi: 10.1186/s13059-016-1044-7.

Partial European Search Report for Application No. 18847527.1, dated Apr. 21, 2021.

Extended European Search Report for Application No. 18847527.1, dated Aug. 2, 2021.

International Preliminary Report on Patentability dated Jan. 27, 2022, in connection with Application No. PCT/US2020/042016.

Blum et al., Phage-assisted evolution of botulinum neurotoxin proteases with reprogrammed specificity. Science. Feb. 19, 2021;371(6531):803-810. doi: 10.1126/science.abf5972.

Blum, Continuous evolution of bacterial neurotoxins for intracellular protease therapy. 2019. Poster. 1 page.

Blum, Generation of selective botulinum neurotoxin proteases with reprogrammed substrate specificity through phage-assisted directed evolution. Apr. 7, 2020. Powerpoint. 36 pages.

Blum, Generation of selective botulinum neurotoxin proteases with reprogrammed substrate specificity through phage-assisted directed evolution. Jun. 4, 2019. Powerpoint. 24 pages.

Kasai et al., Distinct initial SNARE configurations underlying the diversity of exocytosis. Physiol Rev. Oct. 2012;92(4):1915-64. doi: 10.1152/physrev.00007.2012.

Liu et al., PTEN deletion enhances the regenerative ability of adult corticospinal neurons. Nat Neurosci. Sep. 2010;13(9):1075-81. doi: 10.1038/nn.2603. Epub Aug. 8, 2010.

Meng et al., Role of SNARE proteins in tumourigenesis and their potential as targets for novel anti-cancer therapeutics. Biochim Biophys Acta. Aug. 2015;1856(1):1-12. doi: 10.1016/j.bbcan.2015.04.002. Epub May 5, 2015.

Nicholson-Fish et al., VAMP4 is an Essential Cargo Molecule for Activity-Dependent Bulk Endocytosis. Neuron. Dec. 2, 2015;88(5):973-984. doi: 10.1016/j.neuron.2015.10.043. Epub Nov. 19, 2015.

Raingo et al., VAMP4 directs synaptic vesicles to a pool that selectively maintains asynchronous neurotransmission. Nat Neurosci. Mar. 11, 2012;15(5):738-45. doi: 10.1038/nn.3067.

Ruiz-Martinez et al., YKT6 expression, exosome release, and survival in non-small cell lung cancer. Oncotarget. Aug. 9, 2016;7(32):51515-51524. doi: 10.18632/oncotarget.9862.

Zhang et al., Identification and characterization of a novel botulinum neurotoxin. Nat Commun. Aug. 3, 2017;8:14130. doi: 10.1038/ncomms14130.

Sikorra et al., Identification and Characterization of Botulinum Neurotoxin A Substrate Binding Pockets and Their Re-Engineering for Human SNAP-23. J Mol Biol. Jan. 29, 2016;428(2 Pt A):372-384. doi: 10.1016/j.jmb.2015.10.024. Epub Oct. 30, 2015.

Sikorra et al., Identification of the amino acid residues rendering TI-VAMP insensitive toward botulinum neurotoxin B. J Mol Biol. Mar. 24, 2006;357(2):574-82. doi: 10.1016/j.jmb.2005.12.075. Epub Jan. 18, 2006.

U.S. Appl. No. 18/050,014, filed Oct. 26, 2022, Liu et al.

Burland et al., Analysis of the *Escherichia coli* genome VI: DNA sequence of the region from 92.8 through 100 minutes. Nucleic Acids Res. Jun. 25, 1995;23(12):2105-19. doi: 10.1093/nar/23.12.2105.

Chen et al., Mechanism of substrate recognition by botulinum neurotoxin serotype A. J Biol Chem. Mar. 30, 2007;282(13):9621-9627. doi: 10.1074/jbc.M611211200. Epub Jan. 23, 2007.

Esvelt et al., A system for the continuous directed evolution of biomolecules. Nature. Apr. 28, 2011;472(7344):499-503. doi: 10.1038/nature09929. Epub Apr. 10, 2011.

Jones et al., Phage-Assisted Continuous Evolution and Selection of Enzymes for Chemical Synthesis. ACS Cent Sci. Sep. 22, 2021;7(9):1581-1590. doi: 10.1021/acscentsci.1c00811. Epub Sep. 13, 2021.

Lee et al., Enhanced production of human full-length immunoglobulin G1 in the periplasm of *Escherichia coli*. Appl Microbiol Biotechnol. Feb. 2014;98(3):1237-46. doi: 10.1007/s00253-013-5390-z. Epub Nov. 26, 2013.

Manta et al., Disulfide Bond Formation in the Periplasm of *Escherichia coli*. EcoSal Plus. Feb. 2019;8(2). doi: 10.1128/ecosalplus.ESP-0012-2018.

Morrison et al., Disulfide-compatible phage-assisted continuous evolution in the periplasmic space. Nat Commun. Oct. 13, 2021;12(1):5959. doi: 10.1038/s41467-021-26279-8.

Popa et al., Phage-Assisted Continuous Evolution (PACE): A Guide Focused on Evolving Protein—DNA Interactions. ACS Omega. Oct. 16, 2020;5(42):26957-26966. doi: 10.1021/acsomega.0c03508. eCollection Oct. 27, 2020.

\* cited by examiner

|     | rAPOBEC1 residue number |    |    |     |     |     |     | eT7n residue |    |    |     |
| --- | --- | --- | --- | --- | --- | --- | --- | --- | --- | --- | --- |
|     | 24 | 63 | 64 | 113 | 123 | 149 | 205 | 21 | 81 | 93 | 129 |
| wt   | E | E | V | F | A | S | F | N | I | A | N |
| 35.1 | E | E | V | C | E | S | F | N | I | A | K |
| 35.2 | E | E | V | F | A | Y | S | K | I | A | N |
| 36.1 | E | E | V | C | E | S | S | N | T | A | K |
| 36.2 | E | A | V | C | E | S | S | N | I | A | K |

FIG. 2B

|         | rAPOBEC1 residue |    |    |    |    |    |     |     |     |     |     |     |     |     |
| ------- | --- | --- | --- | --- | --- | --- | --- | --- | --- | --- | --- | --- | --- | --- |
|         | 33 | 45 | 57 | 63 | 65 | 75 | 101 | 113 | 123 | 149 | 165 | 166 | 204 | 205 | 224 |
| wt      | R | G | N | E | N | Y | T | F | A | S | A | H | T | F | W |
| 43.1    | R | D | N | E | N | H | T | C | E | S | A | N | T | S | W |
| 43.2    | R | G | N | A* | N | Y | T | C | E | S | T | H | T | S | W |
| 43.2-rev| R | G | N | E | N | Y | T | C | E | S | T | H | T | S | W |
| 43.3    | R | G | S | E | N | Y | I | R | E | S | A | H | T | S | W |
| 43.4    | C | G | N | E | N | Y | T | C | E | Y | A | H | T | S | W |
| 43.5    | R | G | N | E | N | Y | T | C | E | S | A | H | P | S | W |
| 43.6    | R | G | N | E | D | Y | T | C | E | S | A | H | T | S | R |

FIG. 2C

SEQUENCE LISTING

<160> NUMBER OF SEQ IDS: 48

<210> SEQ ID NO 1
<211> LENGTH: 339
<212> TYPE: DNA
<213> ORGANISM: Artificial Sequence
<220> FEATURE:
<223> OTHER INFORMATION: Synthetic polypeptide

<400> SEQUENCE: 1

```
atgaaaaaat tattattcgc aattcctttta tgtctcagct acgaaaccga atcttgacc      60 gtcgaatatg gtctgctgcc aatcggcaag attgttgaaa acgtattga atgtacggtc     120 tactcagtgg ataacaacgg caatatctac acccagccgg tggcccagtg gcatgaccgt    180
ggtgaacagg aagtgttcga atattgtctg aagacggat ctttaatccg tgccacaaag     240
gatcacaaat ttatgactgt agatggtcag atgctcccaa tcgacgaaat ttttgaacgc    300
gaattagacc tgatgcgcgt ggataatctc ccgaattaa                            339
```

<210> SEQ ID NO 2
<211> LENGTH: 1362
<212> TYPE: DNA
<213> ORGANISM: Artificial Sequence
<220> FEATURE:
<223> OTHER INFORMATION: Synthetic polypeptide

<400> SEQUENCE: 2

```
atgatcaaaa ttgccacgcg taaatatta ggcaaacaga atgtttatga tatcggtgtc       60
gagcgcgatc ataatttcgc gctgaaaaac ggctttatcg ccagcaattg ttttaatgtt    120
gttcctttct attctcactc cgctgaaact gttgaaagtt gtttagcaaa accccataca    180
gaaaattcat ttactaacgt ctggaaagac gacaaaactt tagatcgtta cgctaactat    240
gagggctgtc tgtggaatgc tacaggcgtt gtagtttgta ctggtgacga aactcagtgt    300
tacggtacat gggttcctat tgggcttgct atccctgaaa atgagggtgg tggctctgag    360
ggtggcggtt ctgagggtgg cggttctgag ggtggcggta ctaaacctcc tgagtacggt    420
```

```
gatacaccta ttccgggcta tacttatatc aaccctctcg acggcactta tccgcctggt      480
actgagcaaa accccgctaa tcctaatcct tctcttgagg agtctcagcc tcttaatact      540
ttcatgtttc agaataatag gttccgaaat aggcaggggg cattaactgt ttatacgggc      600
actgttactc aaggcactga ccccgttaaa acttattacc agtacactcc tgtatcatca      660
aaagccatgt atgacgctta ctggaacggt aaattcagag actgcgcttt ccattctggc      720
tttaatgagg atccattcgt ttgtgaatat caaggccaat cgtctgacct gcctcaacct      780
cctgtcaatg ctggcggcgg ctctggtggt ggttctggtg gcggctctga gggtggtggc      840
tctgagggtg gcggttctga gggtggcggc tctgagggag gcggttccgg tggtggctct      900
ggttccggtg attttgatta tgaaaagatg gcaaacgcta ataaggggc tatgaccgaa       960 aatgccgatg aaaacgcgct acagtctgac gctaaaggca aacttgattc tgtcgctact     1020
gattacggtg ctgctatcga tggtttcatt ggtgacgttt ccggccttgc taatggtaat     1080
ggtgctactg gtgattttgc tggctctaat tcccaaatgg ctcaagtcgg tgacggtgat     1140
aattcacctt taatgaataa tttccgtcaa tatttacctt ccctccctca atcggttgaa     1200
tgtcgccctt ttgtctttgg cgctggtaaa ccttacgagt tcagtatcga ctgcgataag     1260
atcaacctgt tccgcggtgt ctttgcgttt cttttatatg ttgccacctt tatgtatgta     1320
ttttctacgt ttgctaacat actgcgtaat aaggagtctt aa                        1362

<210> SEQ ID NO 3
<211> LENGTH: 534
<212> TYPE: DNA
<213> ORGANISM: Artificial Sequence
<220> FEATURE:
<223> OTHER INFORMATION: Synthetic polypeptide

<400> SEQUENCE: 3
aacacgatta acatcgctaa gaacgacttc tctgacatcg aactggctgc tatcccgttc       60
aacactctgg ctgaccatta cggtgagcgt ttagctcgcg aacagttggc ccttgagcat      120
gagtcttacg agatgggtga agcacgcttc cgcaagatgt tgagcgtca acttaaagct       180 ggtgaggttg cggataacgc tgccgccaag cctctcatca ctaccctact ccctaagatg      240
attgcacgca tcaacgactg gtttgaggaa gtgaaagcta agcgcggcaa gcgcccgaca      300
gccttccagt tcctgcaaga aatcaagccg gaagccgtag cgtacatcac cattaagacc      360
actctggctt gcctaaccag tgctgacaat acaaccgttc aggctgtagc aagcgcaatc      420
ggtcgggcca ttgaggacga ggctcgcttc ggtcgtatcc gtgaccttga agctaagcac      480
ttcaagaaaa acgttgagga caaactcaac aagcgcgtag ggcacgtcta caag            534

<210> SEQ ID NO 4
<211> LENGTH: 534
<212> TYPE: DNA
<213> ORGANISM: Artificial Sequence
<220> FEATURE:
<223> OTHER INFORMATION: Synthetic polypeptide

<400> SEQUENCE: 4
aacaccatta atatcgctaa gaacggcttc tctgatatcg aactggctgc tatcccgttc       60
aacactctgg ctgaccatta cggtgagcgt ttagctcgcg aacagttggc ccttgagcat      120
gagtcttacg agatggatga agcacgcttc cgcaagatgt tgagcgtca acttaaagct       180 ggtgaggttg cggataacac tgccgccaat cctctcatca ctaccctact ccttaagatg      240
```

```
attgcacgca tcaaggactg gtttgaggaa gtgaaagcta agcgcggcaa gcgcccgaca    300
gccttccatt tcctgaaaga aatcaagccg gaagccgtag cgtacatcac cattaaggcc    360
actctggctt gcctaaccag tgctaacaaa acaaccgttc aggctgtagc aagcgcaatc    420
ggtcgggcca ttgaggacga ggctcgcttc ggtcgtatcc gttaccttga agctaagcac    480
ttcaagaaaa acgttgagga acaactcaac aagcgcgtag ggcacgtcca caag          534

<210> SEQ ID NO 5
<211> LENGTH: 105
<212> TYPE: DNA
<213> ORGANISM: Artificial Sequence
<220> FEATURE:
<223> OTHER INFORMATION: Synthetic polypeptide

<400> SEQUENCE: 5
ttgcaaagaa tgaaacaact tgaaccgaag gttgaagaat tgcttccgaa aaattatcac     60
ttggaaaatg aggttgccag attaaagaaa ttagttggcg aacgc                    105

<210> SEQ ID NO 6
<211> LENGTH: 684
<212> TYPE: DNA
<213> ORGANISM: Artificial Sequence
<220> FEATURE:
<223> OTHER INFORMATION: Synthetic polypeptide

<400> SEQUENCE: 6
tcttctgaaa ccggtccggt tgcggttgac ccgaccctgc gtcgtcgtat cgaaccgcac     60
gaattcgaag ttttcttcga cccgcgtgaa ctgcgtaaag aaacctgcct gctgtacgaa    120
atcaactggg gtggtcgtca ctctatctgg cgtcacacct ctcagaacac caacaaacac    180
gttgaagtta acttcatcga aaaattcacc accgaacgtt acttctgccc gaacacccgt    240
tgctctatca cctggttcct gtcttggtct ccgtgcggtg aatgctctcg tgcgatcacc    300
gaattcctgt ctcgttaccc gcacgttacc ctgttcatct acatcgcgcg tctgtaccac    360
cacgcggacc cgcgtaaccg tcagggtctg cgtgacctga tctcttctgg tgttaccatc    420
cagatcatga ccgaacagga atctggttac tgctggcgta acttcgttaa ctactctccg    480
tctaacgaag cgcactggcc gcgttacccg cacctgtggg ttcgtctgta cgttctggaa    540
ctgtactgca tcatcctggg tctgccgccg tgcctgaaca tcctgcgtcg taaacagccg    600
cagctgacct tcttcaccat cgcgctgcag tcttgccact accagcgtct gccgccgcac    660
atcctgtggg cgaccggtct gaaa                                           684

<210> SEQ ID NO 7
<211> LENGTH: 684
<212> TYPE: DNA
<213> ORGANISM: Artificial Sequence
<220> FEATURE:
<223> OTHER INFORMATION: Synthetic polypeptide

<400> SEQUENCE: 7
tcttctgaaa ccggtccggt tgcggttgac ccgaccctgc gtcgtcgtat cgaaccgcac     60
gaattcgaag ttttcttcga cccgcgtgaa ctgcgtaaag aaacctgcct gctgtacgaa    120
atcaactggg gtggtcgtca ctctatctgg cgtcacacct ctcagaacac caacaaacac    180
gttgaagtta acttcatcga aaaattcacc accgaacgtt acttctgccc gaacacccgt    240
tgctctatca cctggttcct gtcttggtct ccgtgcggtg aatgctctcg tgcgatcacc    300
gaattcctgt ctcgttaccc gcacgttacc ctgtgcatct acatcgcgcg tctgtaccac    360
```

```
cacgaggacc cgcgtaaccg tcagggtctg cgtgacctga tctcttctgg tgttaccatc    420
cagatcatga ccgaacagga atctggttac tgctggcgta acttcgttaa ctactctccg    480
tctaacgaag cgcactggcc gcgttacccg cacctgtggg ttcgtctgta cgttctggaa    540
ctgtactgca tcatcctggg tctgccgccg tgcctgaaca tcctgcgtcg taaacagccg    600
cagctgacct ccttcaccat cgcgctgcag tcttgccact accagcgtct gccgccgcac    660
atcctgtggg cgaccggtct gaaa                                          684
```

<210> SEQ ID NO 8
<211> LENGTH: 684
<212> TYPE: DNA
<213> ORGANISM: Artificial Sequence
<220> FEATURE:
<223> OTHER INFORMATION: Synthetic polypeptide

<400> SEQUENCE: 8

```
tcttctgaaa ccggtccggt tgcggttgac ccgaccctgc gtcgtcgtat cgaaccgcac     60
gaattcgaag ttttcttcga cccgcgtgaa ctgcgtaaag aaacctgcct gctgtacgaa    120
atcaactggg atggtcgtca ctctatctgg cgtcacacct ctcagaacac caacaaacac    180
gttgaagtta acttcatcga aaaattcacc accgaacgtc acttctgccc taacacccgt    240
tgctctatca cctggttcct gtcttggtct ccgtgcggtg aatgctctcg tgcgatcacc    300
gaattcctgt ctcgttaccc gcacgttacc ctgtgcatct acatcgcgcg tctgtaccac    360
cacgaggacc cgcgtaaccg tcagggtctg cgtgacctga tctcttctgg tgttaccatc    420
cagatcatga ccgaacagga atctggttac tgctggcgta acttcgttaa ctactctccg    480
tctaacgaag cgaactggcc gcgttacccg cacctgtggg ttcgtctgta cgttctggaa    540
ctgtactgca tcatcctggg tctgccgccg tgcctgaaca tcctgcgtcg taaacagccg    600
cagctgacct ccttcaccat cgcgctgcag tcttgccact accagcgtct gccgccgcac    660
atcctgtggg cgcccggtct gaaa                                          684
```

<210> SEQ ID NO 9
<211> LENGTH: 684
<212> TYPE: DNA
<213> ORGANISM: Artificial Sequence
<220> FEATURE:
<223> OTHER INFORMATION: Synthetic polypeptide

<400> SEQUENCE: 9

```
tcttctgaaa ccggtccggt tgcggttgac ccgaccctgc gtcgtcgtat cgaaccgcac     60
gaattcgaag ttttcttcga cccgcgtgaa ctgcgtaaag aaacctgtct gctgtacgaa    120
atcaactggg gtggtcgtca ctctatctgg cgtcacacct ctcagaacac caacaaacac    180
gttgcagtta acttcatcga aaaattcacc accgaacgtt acttctgccc gaacacccgt    240
tgctctatca cctggttcct gtcttggtct ccgtgcggtg aatgctctcg tgcgatcacc    300
gaattcctgt ctcgttaccc gcacgttacc ctgtgcatct acatcgcgcg tctgtaccac    360
cacgaggacc cgcgtaaccg tcagggtctg cgtgacctga tctcttctgg tgttaccatc    420
cagatcatga ccgaacagga atctggttac tgctggcgta acttcgttaa ctactctccg    480
tctaacgaaa cgcactggcc gcgttacccg cacctgtggg ttcgtctgta cgttctggaa    540
ctgtactgca tcatcctggg tctgccgccg tgcctgaaca tcctgcgtcg taaacagccg    600
cagctgacct ccttcaccat cgcgctgcag tcttgccact accagcgtct gccgccgcac    660
```

```
atcctgtggg cgaccggtct gaaa                                          684
```

<210> SEQ ID NO 10
<211> LENGTH: 684
<212> TYPE: DNA
<213> ORGANISM: Artificial Sequence
<220> FEATURE:
<223> OTHER INFORMATION: Synthetic polypeptide

<400> SEQUENCE: 10

```
tcttctgaaa ccggtccggt tgcggttgac ccgaccctgc gtcgtcgtat cgaaccgcac    60
gaattcgaag ttttcttcga cccgcgtgaa ctgcgtaaag aaacctgtct gctgtacgaa   120
atcaactggg gtggtcgtca ctctatctgg cgtcacacct ctcagaacac caacaaacac   180
gttgaagtta acttcatcga aaaattcacc accgaacgtt acttctgccc gaacacccgt   240
tgctctatca cctggttcct gtcttggtct ccgtgcggtg aatgctctcg tgcgatcacc   300
gaattcctgt ctcgttaccc gcacgttacc ctgtgcatct acatcgcgcg tctgtaccac   360
cacgaggacc cgcgtaaccg tcagggtctg cgtgacctga tctcttctgg tgttaccatc   420
cagatcatga ccgaacagga atctggttac tgctggcgta acttcgttaa ctactctccg   480
tctaacgaaa cgcactggcc gcgttacccg cacctgtggg ttcgtctgta cgttctggaa   540
ctgtactgca tcatcctggg tctgccgccg tgcctgaaca tcctgcgtcg taaacagccg   600
cagctgacct ccttcaccat cgcgctgcag tcttgccact accagcgtct gccgccgcac   660
atcctgtggg cgaccggtct gaaa                                          684
```

<210> SEQ ID NO 11
<211> LENGTH: 684
<212> TYPE: DNA
<213> ORGANISM: Artificial Sequence
<220> FEATURE:
<223> OTHER INFORMATION: Synthetic polypeptide

<400> SEQUENCE: 11

```
agctcagaga ctggcccagt ggctgtggac cccacattga gacggcggat cgagccccat    60
gagtttgagg tattcttcga tccgagagag ctccgcaagg agacctgcct gctttacgaa   120
attaattggg ggggccggca ctccatttgg cgacatacat cacagaacac taacaagcac   180
gtcgaagtca acttcatcga gaagttcacg acagaaagat attctgtcc gaacacaagg   240
tgcagcatta cctggttcct cagctggagc ccatgcggcg aatgtagtag gccatcact   300
gaattcctgt caaggtatcc ccacgtcact ctgtttattt acatcgcaag gctgtaccac   360
cacgctgacc cccgcaatcg acaaggcctg cgggatttga tctcttcagg tgtgactatc   420
caaattatga ctgagcagga gtcaggatac tgctggagaa actttgtgaa ttatagcccg   480
agtaatgaag cccactggcc taggtatccc catctgtggg tacgactgta cgttcttgaa   540
ctgtactgca tcatactggg cctgcctcct tgtctcaaca ttctgagaag gaagcagcca   600
cagctgacat tctttaccat cgctcttcag tcttgtcatt accagcgact gcccccacac   660
attctctggg ccaccgggtt gaaa                                          684
```

<210> SEQ ID NO 12
<211> LENGTH: 684
<212> TYPE: DNA
<213> ORGANISM: Artificial Sequence
<220> FEATURE:
<223> OTHER INFORMATION: Synthetic polypeptide

<400> SEQUENCE: 12

```
agctcagaga ctggcccagt ggctgtggac cccacattga dacggcggat cgagcccat      60 gagtttgagg tattcttcga tccgagagag ctccgcaagg agacctgcct gctttacgaa    120
attaattggg ggggccggca ctccatttgg cgacatacat cacagaacac taacaagcac    180
gtcgaagtca acttcatcga gaagttcacg acagaaagat atttctgtcc gaacacaagg    240
tgcagcatta cctggtttct cagctggagc ccatgcggcg aatgtagtag ggccatcact    300
gaattcctgt caaggtatcc ccacgtcact ctgtgtattt acatcgcaag gctgtaccac    360
cacgaagacc cccgcaatcg acaaggcctg cgggatttga tctcttcagg tgtgactatc    420
caaattatga ctgagcagga gtcaggatac tgctggagaa actttgtgaa ttatagcccg    480
agtaatgaag cccactggcc taggtatccc catctgtggg tacgactgta cgttcttgaa    540
ctgtactgca tcatactggg cctgcctcct tgtctcaaca ttctgagaag gaagcagcca    600
cagctgacat cctttaccat cgctcttcag tcttgtcatt accagcgact gcccccacac    660
attctctggg ccaccgggtt gaaa                                           684

<210> SEQ ID NO 13
<211> LENGTH: 684
<212> TYPE: DNA
<213> ORGANISM: Artificial Sequence
<220> FEATURE:
<223> OTHER INFORMATION: Synthetic polypeptide

<400> SEQUENCE: 13
agctcagaga ctggcccagt ggctgtggac cccacattga dacggcggat cgagcccat      60 gagtttgagg tattcttcga tccgagagag ctccgcaagg agacctgcct gctttacgaa    120
attaattggg atggccggca ctccatttgg cgacatacat cacagaacac taacaagcac    180
gtcgaagtca acttcatcga gaagttcacg acagaaagac acttctgtcc gaacacaagg    240
tgcagcatta cctggtttct cagctggagc ccatgcggcg aatgtagtag ggccatcact    300
gaattcctgt caaggtatcc ccacgtcact ctgtgtattt acatcgcaag gctgtaccac    360
cacgaagacc cccgcaatcg acaaggcctg cgggatttga tctcttcagg tgtgactatc    420
caaattatga ctgagcagga gtcaggatac tgctggagaa actttgtgaa ttatagcccg    480
agtaatgaag ccaactggcc taggtatccc catctgtggg tacgactgta cgttcttgaa    540
ctgtactgca tcatactggg cctgcctcct tgtctcaaca ttctgagaag gaagcagcca    600
cagctgacat cctttaccat cgctcttcag tcttgtcatt accagcgact gcccccacac    660
attctctggg ccaccgggtt gaaa                                           684

<210> SEQ ID NO 14
<211> LENGTH: 684
<212> TYPE: DNA
<213> ORGANISM: Artificial Sequence
<220> FEATURE:
<223> OTHER INFORMATION: Synthetic polypeptide

<400> SEQUENCE: 14
agctcagaga ctggcccagt ggctgtggac cccacattga dacggcggat cgagcccat      60 gagtttgagg tattcttcga tccgagagag ctccgcaagg agacctgcct gctttacgaa    120
attaattggg ggggccggca ctccatttgg cgacatacat cacagaacac taacaagcac    180
gtcgaagtca acttcatcga gaagttcacg acagaaagat atttctgtcc gaacacaagg    240
tgcagcatta cctggtttct cagctggagc ccatgcggcg aatgtagtag ggccatcact    300
```

-continued

```
gaattcctgt caaggtatcc ccacgtcact ctgtgtattt acatcgcaag gctgtaccac      360
cacgaagacc cccgcaatcg acaaggcctg cgggatttga tctcttcagg tgtgactatc      420
caaattatga ctgagcagga gtcaggatac tgctggagaa actttgtgaa ttatagcccg      480
agtaatgaaa cccactggcc taggtatccc catctgtggg tacgactgta cgttcttgaa      540
ctgtactgca tcatactggg cctgcctcct tgtctcaaca ttctgagaag gaagcagcca      600
cagctgacat cctttaccat cgctcttcag tcttgtcatt accagcgact gccccacac       660 attctctggg ccaccgggtt gaaa                                              684
```

<210> SEQ ID NO 15
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 15

```
Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
    210                 215                 220

Ala Thr Gly Leu Lys
225
```

<210> SEQ ID NO 16
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 16

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
                100                 105                 110

Cys Ile Tyr Ile Ala Arg Leu Tyr His His Glu Asp Pro Arg Asn Arg
            115                 120                 125

Gln Gly Leu Arg Asp Leu Ile Ser Ser Gly Val Thr Ile Gln Ile Met
130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Ser Phe Thr Ile
            195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 17
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 17

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30

Arg Lys Glu Thr Cys Leu Leu Tyr Glu Ile Asn Trp Asp Gly Arg His
            35                  40                  45

Ser Ile Trp Arg His Thr Ser Gln Asn Thr Asn Lys His Val Glu Val
50                  55                  60

Asn Phe Ile Glu Lys Phe Thr Thr Glu Arg His Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
                100                 105                 110

Cys Ile Tyr Ile Ala Arg Leu Tyr His His Glu Asp Pro Arg Asn Arg
            115                 120                 125

```
Gln Gly Leu Arg Asp Leu Ile Ser Ser Gly Val Thr Ile Gln Ile Met
            130                 135                 140

Thr Glu Gln Glu Ser Gly Tyr Cys Trp Arg Asn Phe Val Asn Tyr Ser
145                 150                 155                 160

Pro Ser Asn Glu Ala Asn Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Ser Phe Thr Ile
            195                 200                 205

Ala Leu Gln Ser Cys His Tyr Gln Arg Leu Pro Pro His Ile Leu Trp
210                 215                 220

Ala Pro Gly Leu Lys
225

<210> SEQ ID NO 18
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 18

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Ala Val
50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Cys Ile Tyr Ile Ala Arg Leu Tyr His His Glu Asp Pro Arg Asn Arg
            115                 120                 125

Gln Gly Leu Arg Asp Leu Ile Ser Ser Gly Val Thr Ile Gln Ile Met
            130                 135                 140

Thr Glu Gln Glu Ser Gly Tyr Cys Trp Arg Asn Phe Val Asn Tyr Ser
145                 150                 155                 160

Pro Ser Asn Glu Thr His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Ser Phe Thr Ile
            195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 19
<211> LENGTH: 229
```

<212> TYPE: PRT
<213> ORGANISM: Artificial Sequence
<220> FEATURE:
<223> OTHER INFORMATION: Synthetic polypeptide

<400> SEQUENCE: 19

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Cys Ile Tyr Ile Ala Arg Leu Tyr His His Glu Asp Pro Arg Asn Arg
        115                 120                 125

Gln Gly Leu Arg Asp Leu Ile Ser Ser Gly Val Thr Ile Gln Ile Met
130                 135                 140

Thr Glu Gln Glu Ser Gly Tyr Cys Trp Arg Asn Phe Val Asn Tyr Ser
145                 150                 155                 160

Pro Ser Asn Glu Thr His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Ser Phe Thr Ile
        195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 20
<211> LENGTH: 1367
<212> TYPE: PRT
<213> ORGANISM: Artificial Sequence
<220> FEATURE:
<223> OTHER INFORMATION: Synthetic polypeptide

<400> SEQUENCE: 20

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

-continued

Phe His Arg Leu Glu Glu Ser Phe Leu Val Glu Asp Lys Lys His
            100                 105                 110

Glu Arg His Pro Ile Phe Gly Asn Ile Val Asp Glu Val Ala Tyr His
            115                 120                 125

Glu Lys Tyr Pro Thr Ile Tyr His Leu Arg Lys Lys Leu Val Asp Ser
        130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

```
Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
```

```
                930             935             940
Asn Asp Lys Leu Ile Arg Glu Val Lys Val Ile Thr Leu Lys Ser Lys
945             950             955             960

Leu Val Ser Asp Phe Arg Lys Asp Phe Gln Phe Tyr Lys Val Arg Glu
            965             970             975

Ile Asn Asn Tyr His His Ala His Asp Ala Tyr Leu Asn Ala Val Val
                980             985             990

Gly Thr Ala Leu Ile Lys Lys Tyr Pro Lys Leu Glu Ser Glu Phe Val
        995             1000            1005

Tyr Gly Asp Tyr Lys Val Tyr Asp Val Arg Lys Met Ile Ala Lys
    1010            1015            1020

Ser Glu Gln Glu Ile Gly Lys Ala Thr Ala Lys Tyr Phe Phe Tyr
    1025            1030            1035

Ser Asn Ile Met Asn Phe Phe Lys Thr Glu Ile Thr Leu Ala Asn
    1040            1045            1050

Gly Glu Ile Arg Lys Arg Pro Leu Ile Glu Thr Asn Gly Glu Thr
    1055            1060            1065

Gly Glu Ile Val Trp Asp Lys Gly Arg Asp Phe Ala Thr Val Arg
    1070            1075            1080

Lys Val Leu Ser Met Pro Gln Val Asn Ile Val Lys Lys Thr Glu
    1085            1090            1095

Val Gln Thr Gly Gly Phe Ser Lys Glu Ser Ile Leu Pro Lys Arg
    1100            1105            1110

Asn Ser Asp Lys Leu Ile Ala Arg Lys Lys Asp Trp Asp Pro Lys
    1115            1120            1125

Lys Tyr Gly Gly Phe Asp Ser Pro Thr Val Ala Tyr Ser Val Leu
    1130            1135            1140

Val Val Ala Lys Val Glu Lys Gly Lys Ser Lys Lys Leu Lys Ser
    1145            1150            1155

Val Lys Glu Leu Leu Gly Ile Thr Ile Met Glu Arg Ser Ser Phe
    1160            1165            1170

Glu Lys Asn Pro Ile Asp Phe Leu Glu Ala Lys Gly Tyr Lys Glu
    1175            1180            1185

Val Lys Lys Asp Leu Ile Ile Lys Leu Pro Lys Tyr Ser Leu Phe
    1190            1195            1200

Glu Leu Glu Asn Gly Arg Lys Arg Met Leu Ala Ser Ala Gly Glu
    1205            1210            1215

Leu Gln Lys Gly Asn Glu Leu Ala Leu Pro Ser Lys Tyr Val Asn
    1220            1225            1230

Phe Leu Tyr Leu Ala Ser His Tyr Glu Lys Leu Lys Gly Ser Pro
    1235            1240            1245

Glu Asp Asn Glu Gln Lys Gln Leu Phe Val Glu Gln His Lys His
    1250            1255            1260

Tyr Leu Asp Glu Ile Ile Glu Gln Ile Ser Glu Phe Ser Lys Arg
    1265            1270            1275

Val Ile Leu Ala Asp Ala Asn Leu Asp Lys Val Leu Ser Ala Tyr
    1280            1285            1290

Asn Lys His Arg Asp Lys Pro Ile Arg Glu Gln Ala Glu Asn Ile
    1295            1300            1305

Ile His Leu Phe Thr Leu Thr Asn Leu Gly Ala Pro Ala Ala Phe
    1310            1315            1320

Lys Tyr Phe Asp Thr Thr Ile Asp Arg Lys Arg Tyr Thr Ser Thr
    1325            1330            1335
```

-continued

Lys Glu Val Leu Asp Ala Thr Leu Ile His Gln Ser Ile Thr Gly
1340                1345                1350

Leu Tyr Glu Thr Arg Ile Asp Leu Ser Gln Leu Gly Gly Asp
    1355                1360                1365

<210> SEQ ID NO 21
<211> LENGTH: 1367
<212> TYPE: PRT
<213> ORGANISM: Artificial Sequence
<220> FEATURE:
<223> OTHER INFORMATION: Synthetic polypeptide

<400> SEQUENCE: 21

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

```
Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
            370                 375                 380

Thr Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
            405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
            450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
            485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
            530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
            565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
            610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
            645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
            690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
            725                 730                 735

Leu Gln Thr Val Lys Val Val Asp Glu Leu Val Lys Val Met Gly Arg
            740                 745                 750
```

-continued

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe

```
                       1160                1165                1170

Glu  Lys  Asn  Pro  Ile  Asp  Phe  Leu  Glu  Ala  Lys  Gly  Tyr  Lys  Glu
        1175                1180                1185

Val  Lys  Lys  Asp  Leu  Ile  Ile  Lys  Leu  Pro  Lys  Tyr  Ser  Leu  Phe
        1190                1195                1200

Glu  Leu  Glu  Asn  Gly  Arg  Lys  Arg  Met  Leu  Ala  Ser  Ala  Gly  Glu
        1205                1210                1215

Leu  Gln  Lys  Gly  Asn  Glu  Leu  Ala  Leu  Pro  Ser  Lys  Tyr  Val  Asn
        1220                1225                1230

Phe  Leu  Tyr  Leu  Ala  Ser  His  Tyr  Glu  Lys  Leu  Lys  Gly  Ser  Pro
        1235                1240                1245

Glu  Asp  Asn  Glu  Gln  Lys  Gln  Leu  Phe  Val  Glu  Gln  His  Lys  His
        1250                1255                1260

Tyr  Leu  Asp  Glu  Ile  Ile  Glu  Gln  Ile  Ser  Glu  Phe  Ser  Lys  Arg
        1265                1270                1275

Val  Ile  Leu  Ala  Asp  Ala  Asn  Leu  Asp  Lys  Val  Leu  Ser  Ala  Tyr
        1280                1285                1290

Asn  Lys  His  Arg  Asp  Lys  Pro  Ile  Arg  Glu  Gln  Ala  Glu  Asn  Ile
        1295                1300                1305

Ile  His  Leu  Phe  Thr  Leu  Thr  Asn  Leu  Gly  Ala  Pro  Ala  Ala  Phe
        1310                1315                1320

Lys  Tyr  Phe  Asp  Thr  Thr  Ile  Asp  Arg  Lys  Arg  Tyr  Thr  Ser  Thr
        1325                1330                1335

Lys  Glu  Val  Leu  Asp  Ala  Thr  Leu  Ile  His  Gln  Ser  Ile  Thr  Gly
        1340                1345                1350

Leu  Tyr  Glu  Thr  Arg  Ile  Asp  Leu  Ser  Gln  Leu  Gly  Gly  Asp
        1355                1360                1365

<210> SEQ ID NO 22
<211> LENGTH: 84
<212> TYPE: PRT
<213> ORGANISM: Artificial Sequence
<220> FEATURE:
<223> OTHER INFORMATION: Synthetic polypeptide

<400> SEQUENCE: 22

Met  Thr  Asn  Leu  Ser  Asp  Ile  Ile  Glu  Lys  Glu  Thr  Gly  Lys  Gln  Leu
1               5                   10                  15

Val  Ile  Gln  Glu  Ser  Ile  Leu  Met  Leu  Pro  Glu  Glu  Val  Glu  Glu  Val
            20                  25                  30

Ile  Gly  Asn  Lys  Pro  Glu  Ser  Asp  Ile  Leu  Val  His  Thr  Ala  Tyr  Asp
        35                  40                  45

Glu  Ser  Thr  Asp  Glu  Asn  Val  Met  Leu  Leu  Thr  Ser  Asp  Ala  Pro  Glu
    50                  55                  60

Tyr  Lys  Pro  Trp  Ala  Leu  Val  Ile  Gln  Asp  Ser  Asn  Gly  Glu  Asn  Lys
65                  70                  75                  80

Ile  Lys  Met  Leu

<210> SEQ ID NO 23
<211> LENGTH: 4104
<212> TYPE: DNA
<213> ORGANISM: Streptococcus pyogenes

<400> SEQUENCE: 23
atggataaga aatactcaat aggcttagat atcggcacaa atagcgtcgg atgggcggtg     60
atcactgatg attataaggt tccgtctaaa aagttcaagg ttctgggaaa tacagaccgc    120
```

```
cacagtatca aaaaaaatct tatagggget cttttatttg gcagtggaga gacagcggaa      180
gcgactcgtc tcaaacggac agctcgtaga aggtatacac gtcggaagaa tcgtatttgt      240
tatctacagg agattttttc aaatgagatg gcgaaagtag atgatagttt ctttcatcga      300
cttgaagagt ctttttggt ggaagaagac aagaagcatg aacgtcatcc tattttggga      360
aatatagtag atgaagttgc ttatcatgag aaatatccaa ctatctatca tctgcgaaaa      420 aaaattggcag attctactga taaagcggat ttgcgcttaa tctatttggc cttagcgcat      480
atgattaagt ttcgtggtca tttttttgatt gagggagatt taaatcctga taatagtgat      540
gtggacaaac tatttatcca gttggtacaa atcacaatc aattatttga agaaaaccct      600
attaacgcaa gtagagtaga tgctaaagcg attctttctg cacgattgag taaatcaaga      660
cgattagaaa atctcattgc tcagctcccc ggtgagaaga gaaatggctt gtttgggaat      720
ctcattgctt tgtcattggg attgacccct aattttaaat caaattttga tttggcagaa      780
gatgctaaat tacagctttc aaaagatact tacgatgatg atttagataa tttattggcg      840
caaattggag atcaatatgc tgatttgttt ttggcagcta agaatttatc agatgctatt      900
ttactttcag atatcctaag agtaaatagt gaaataacta aggctcccct atcagcttca      960
atgattaagc gctacgatga acatcatcaa gacttgactc ttttaaaagc tttagttcga     1020
caacaacttc cagaaaagta taagaaaatc ttttttgatc aatcaaaaaa cggatatgca     1080
ggttatattg atgggggagc tagccaagaa gaattttata aatttatcaa accaattttta    1140 gaaaaaatgg atggtactga ggaattattg gtgaaactaa atcgtgaaga tttgctgcgc     1200
aagcaacgga cctttgacaa cggctctatt ccccatcaaa ttcacttggg tgagctgcat     1260
gctattttga aagacaaga agactttat ccattttaa aagacaatcg tgagaagatt       1320
gaaaaaatct tgacttttcg aattccttat tatgttggtc cattggcgcg tggcaatagt     1380
cgttttgcat ggatgactcg gaagtctgaa gaaacaatta ccccatgaa ttttgaagaa      1440 gttgtcgata aggtgcttc agctcaatca tttattgaac gcatgacaaa ctttgataaa     1500
aatcttccaa atgaaaaagt actaccaaaa catagtttgc tttatgagta ttttacggtt     1560
tataacgaat tgacaaaggt caaatatgtt actgagggaa tgcgaaaacc agcattttct     1620
tcaggtgaac agaagaaagc cattgttgat ttactcttca aaacaaatcg aaaagtaacc     1680
gttaagcaat taaagaaga ttatttcaaa aaaatagaat gttttgatag tgttgaaatt      1740
tcaggagttg aagatagatt taatgcttca ttaggcgcct accatgattt gctaaaaatt     1800
attaaagata aagattttt ggataatgaa gaaaatgaag atatcttaga ggatatttgtt     1860 ttaacattga ccttatttga agataggggg atgattgagg aaagacttaa aacatatgct     1920
cacctctttg atgataaggt gatgaaacag cttaaacgtc gccgttatac tggttgggga     1980
cgtttgtctc gaaaattgat taatggtatt agggataagc aatctggcaa aacaatatta     2040 gatttttttga aatcagatgg ttttgccaat cgcaatttta tgcagctgat ccatgatgat     2100
agtttgacat ttaaagaaga tattcaaaaa gcacaggtgt ctggacaagg ccatagttta     2160
catgaacaga ttgctaactt agctggcagt cctgctatta aaaaggtat tttacagact     2220 gtaaaaattg ttgatgaact ggtcaaagta atggggcata agccagaaaa tatcgttatt     2280
gaaatggcac gtgaaaatca gacaactcaa aagggccaga aaaattcgcg agagcgtatg     2340
aaacgaatcg aagaaggtat caagaattaa ggaagtcaga ttcttaaaga gcatcctgtt     2400
gaaaatactc aattgcaaaa tgaaaagctc tatctctatt atctacaaaa tggaagagac     2460
```

| | | |
|---|---|---|
| atgtatgtgg accaagaatt agatattaat cgtttaagtg attatgatgt cgatcacatt | 2520 | |
| gttccacaaa gtttcattaa agacgattca atagacaata aggtactaac gcgttctgat | 2580 | |
| aaaaatcgtg gtaaatcgga taacgttcca agtgaagaag tagtcaaaaa gatgaaaaac | 2640 | |
| tattggagac aacttctaaa cgccaagtta atcactcaac gtaagtttga taatttaacg | 2700 | |
| aaagctgaac gtggaggttt gagtgaactt gataaagctg gttttatcaa acgccaattg | 2760 | |
| gttgaaactc gccaaatcac taagcatgtg gcacaaattt tggatagtcg catgaatact | 2820 | |
| aaatacgatg aaaatgataa acttattcga gaggttaaag tgattacctt aaaatctaaa | 2880 | |
| ttagtttctg acttccgaaa agatttccaa ttctataaag tacgtgagat taacaattac | 2940 | |
| catcatgccc atgatgcgta tctaaatgcc gtcgttggaa ctgctttgat taagaaatat | 3000 | |
| ccaaaacttg aatcggagtt tgtctatggt gattataaag tttatgatgt tcgtaaaatg | 3060 | |
| attgctaagt ctgagcaaga aataggcaaa gcaaccgcaa atatttctt ttactctaat | 3120 | |
| atcatgaact tcttcaaaac agaaattaca cttgcaaatg gagagattcg caaacgccct | 3180 | |
| ctaatcgaaa ctaatgggga aactggagaa attgtctggg ataaagggcg agattttgcc | 3240 | |
| acagtgcgca aagtattgtc catgccccaa gtcaatattg tcaagaaaac agaagtacag | 3300 | |
| acaggcggat tctccaagga gtcaattta ccaaaaagaa attcggacaa gcttattgct | 3360 | |
| cgtaaaaaag actgggatcc aaaaaaatat ggtggttttg atagtccaac ggtagcttat | 3420 | |
| tcagtcctag tggttgctaa ggtggaaaaa gggaaatcga agaagttaaa atccgttaaa | 3480 | |
| gagttactag ggatcacaat tatggaaaga agttcctttg aaaaaaatcc gattgacttt | 3540 | |
| ttagaagcta aaggatataa ggaagttaaa aaagacttaa tcattaaact acctaaatat | 3600 | |
| agtcttttg agttagaaaa cggtcgtaaa cggatgctgg ctagtgccgg agaattacaa | 3660 | |
| aaaggaaatg agctggctct gccaagcaaa tatgtgaatt ttttatattt agctagtcat | 3720 | |
| tatgaaaagt tgaagggtag tccagaagat aacgaacaaa aacaattgtt tgtggagcag | 3780 | |
| cataagcatt atttagatga gattattgag caaatcagtg aattttctaa gcgtgttatt | 3840 | |
| ttagcagatg ccaatttaga taaagttctt agtgcatata caaacatag agacaaacca | 3900 | |
| atacgtgaac aagcagaaaa tattattcat ttatttacgt tgacgaatct ggagctccc | 3960 | |
| gctgcttta aatattttga tacaacaatt gatcgtaaac gatatacgtc tacaaaagaa | 4020 | |
| gttttagatg ccactcttat ccatcaatcc atcactggtc tttatgaaac acgcattgat | 4080 | |
| ttgagtcagc taggaggtga ctga | 4104 | |

<210> SEQ ID NO 24
<211> LENGTH: 1367
<212> TYPE: PRT
<213> ORGANISM: Streptococcus pyogenes

<400> SEQUENCE: 24

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser

-continued

```
                500                 505                 510
Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Gly Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925
```

```
His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr Pro Lys Leu Glu Ser Glu Phe Val
        995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320
```

| | | | | | | | | | | | |
|---|---|---|---|---|---|---|---|---|---|---|---|
| Lys | Tyr | Phe | Asp | Thr | Thr | Ile | Asp | Arg | Lys | Arg | Tyr | Thr Ser Thr |
| 1325 | | | | | 1330 | | | | | 1335 | |

| | | | | | | | | | | | |
|---|---|---|---|---|---|---|---|---|---|---|---|
| Lys | Glu | Val | Leu | Asp | Ala | Thr | Leu | Ile | His | Gln | Ser | Ile Thr Gly |
| 1340 | | | | | 1345 | | | | | 1350 | |

| | | | | | | | | | | | |
|---|---|---|---|---|---|---|---|---|---|---|---|
| Leu | Tyr | Glu | Thr | Arg | Ile | Asp | Leu | Ser | Gln | Leu | Gly | Gly Asp |
| 1355 | | | | | 1360 | | | | | 1365 | |

<210> SEQ ID NO 25
<211> LENGTH: 4212
<212> TYPE: DNA
<213> ORGANISM: Artificial Sequence
<220> FEATURE:
<223> OTHER INFORMATION: Synthetic polypeptide

<400> SEQUENCE: 25

| | |
|---|---|
| atggataaaa agtattctat tggtttagac atcggcacta attccgttgg atgggctgtc | 60 |
| ataaccgatg aatacaaagt accttcaaag aaatttaagg tgttggggaa cacagaccgt | 120 |
| cattcgatta aaagaatcct tatcggtgcc ctcctattcg atagtggcga aacggcagag | 180 |
| gcgactcgcc tgaaacgaac cgctcggaga aggtatacac gtcgcaagaa ccgaatatgt | 240 |
| tacttacaag aaattttttag caatgagatg gccaaagttg acgattcttt ctttcaccgt | 300 |
| ttggaagagt ccttccttgt cgaagaggac aagaaacatg aacggcaccc catctttgga | 360 |
| aacatagtag atgaggtggc atatcatgaa agtacccaa cgatttatca cctcagaaaa | 420 |
| aagctagttg actcaactga taaagcggac ctgaggttaa tctacttggc tcttgcccat | 480 |
| atgataaagt ccgtgggca ctttctcatt gagggtgatc taaatccgga caactcggat | 540 |
| gtcgacaaac tgttcatcca gttagtacaa acctataatc agttgtttga agagaacccct | 600 |
| ataaatgcaa gtggcgtgga tgcgaaggct attcttagcg cccgcctctc taaatcccga | 660 |
| cggctagaaa acctgatcgc acaattaccc ggagagaaga aaaatgggtt gttcggtaac | 720 |
| cttatagcgc tctcactagg cctgacacca aatttttaagt cgaacttcga cttagctgaa | 780 |
| gatgccaaat tgcagcttag taaggacacg tacgatgacg atctcgacaa tctactggca | 840 |
| caaattggag atcagtatgc ggacttattt ttggctgcca aaaaccttag cgatgcaatc | 900 |
| ctccctatctg acatactgag agttaatact gagattacca aggcgccgtt atccgcttca | 960 |
| atgatcaaaa ggtacgatga acatcaccaa gacttgacac ttctcaaggc cctagtccgt | 1020 |
| cagcaactgc ctgagaaata taaggaaata ttctttgatc agtcgaaaaa cgggtacgca | 1080 |
| ggttatattg acggcggagc gagtcaagag gaattctaca gtttatcaa acccatatta | 1140 |
| gagaagatga tgggacgga agagttgctt gtaaaactca atcgcgaaga tctactgcga | 1200 |
| aagcagcgga ctttcgacaa cggtagcatt ccacatcaaa tccacttagg cgaattgcat | 1260 |
| gctatactta gaaggcagga ggatttttat ccgttcctca agacaatcg tgaaaagatt | 1320 |
| gagaaaatcc taaccttctcg cataccttac tatgtgggac ccctggcccg agggaactct | 1380 |
| cggttcgcat ggatgacaag aaagtccgaa gaaacgatta ctccatggaa ttttgaggaa | 1440 |
| gttgtcgata aggtgcgtc agctcaatcg ttcatcgaga ggatgaccaa ctttgacaag | 1500 |
| aatttaccga acgaaaaagt attgcctaag cacagtttac tttacgagta tttcacagtg | 1560 |
| tacaatgaac tcacgaaagt taagtatgtc actgagggca tgcgtaaacc cgcctttcta | 1620 |
| agcggagaac agaagaaagc aatagtagat ctgttattca gaccaaccg caaagtgaca | 1680 |
| gttaagcaat tgaaagagga ctactttaag aaaattgaat gcttcgattc tgtcgagatc | 1740 |
| tccggggtag aagatcgatt taatgcgtca cttggtacgt atcatgacct cctaaagata | 1800 |

```
attaaagata aggacttcct ggataacgaa gagaatgaag atatcttaga agatatagtg    1860
ttgactctta ccctctttga agatcgggaa atgattgagg aaagactaaa aacatacgct    1920
cacctgttcg acgataaggt tatgaaacag ttaaagaggc gtcgctatac gggctgggga    1980
cgattgtcgc ggaaacttat caacgggata agagacaagc aaagtggtaa aactattctc    2040
gattttctaa agagcgacgg cttcgccaat aggaacttta tgcagctgat ccatgatgac    2100
tctttaacct tcaaagagga tatacaaaag gcacaggttt ccggacaagg ggactcattg    2160
cacgaacata ttgcgaatct tgctggttcg ccagccatca aaagggcat actccagaca     2220 gtcaaagtag tggatgagct agttaaggtc atgggacgtc acaaaccgga aaacattgta    2280
atcgagatgg cacgcgaaaa tcaaacgact cagaaggggc aaaaaaacag tcgagagcgg    2340
atgaagagaa tagaagaggg tattaaagaa ctgggcagcc agatcttaaa ggagcatcct    2400
gtggaaaata cccaattgca gaacgagaaa ctttacctct attacctaca aaatggaagg    2460
gacatgtatg ttgatcagga actggacata aaccgtttat ctgattacga cgtcgatcac    2520
attgtacccc aatccttttt gaaggacgat tcaatcgaca ataaagtgct tacacgctcg    2580
gataagaacc gagggaaaag tgacaatgtt ccaagcgagg aagtcgtaaa gaaaatgaag    2640
aactattggc ggcagctcct aaatgcgaaa ctgataacgc aaagaaagtt cgataactta    2700
actaaagctg agaggggtgg cttgtctgaa cttgacaagg ccggatttat taaacgtcag    2760
ctcgtggaaa cccgccaaat cacaaagcat gttgcacaga tactagattc ccgaatgaat    2820
acgaaatacg acgagaacga taagctgatt cgggaagtca agtaatcac tttaaagtca     2880 aaattggtgt cggacttcag aaaggatttt caattctata agttaggga gataaataac     2940 taccaccatg cgcacgacgc ttatcttaat gccgtcgtag ggaccgcact cattaagaaa    3000
tacccgaagc tagaaagtga gtttgtgtat ggtgattaca agtttatga cgtccgtaag     3060 atgatcgcga aaagcgaaca ggagataggc aaggctacag ccaaatactt cttttattct    3120
aacattatga atttctttaa gacggaaatc actctggcaa acggagagat acgcaaacga    3180
cctttaattg aaaccaatgg ggagacaggt gaaatcgtat gggataaggg ccgggacttc    3240
gcgacggtga gaaaagtttt gtccatgccc caagtcaaca tagtaaagaa aactgaggtg    3300
cagaccggag ggttttcaaa ggaatcgatt cttccaaaaa ggaatagtga taagctcatc    3360
gctcgtaaaa aggactggga cccgaaaaag tacggtggct tcgatagccc tacagttgcc    3420
tattctgtcc tagtagtggc aaaagttgag aagggaaaat ccaagaaact gaagtcagtc    3480
aaagaattat ggggataaac gattatggag cgctcgtctt ttgaaaagaa ccccatcgac    3540
ttccttgagg cgaaaggtta caggaagta aaaaaggatc tcataattaa actaccaaag      3600
tatagtctgt ttgagttaga aaatggccga aacggatgt tggctagcgc cggagagctt      3660
caaaagggga acgaactcgc actaccgtct aaatacgtga atttcctgta tttagcgtcc    3720
cattacgaga agttgaaagg ttcacctgaa gataacgaac agaagcaact ttttgttgag    3780
cagcacaaac attatctcga cgaaatcata gagcaaattt cggaattcag taagagagtc    3840
atcctagctg atgccaatct ggacaaagta ttaagcgcat acaacaagca cagggataaa    3900
cccatacgtg agcaggcgga aaatattatc catttgttta ctcttaccaa cctcggcgct    3960
ccagccgcat tcaagtattt tgacacaacg atagatcgca aacgatacac ttctaccaag    4020
gaggtgctag acgcgacact gattcaccaa tccatcacgg gattatatga aactcggata    4080
gatttgtcac agcttggggg tgacggatcc cccaagaaga gaggaaagt ctcgagcgac      4140 tacaaagacc atgacggtga ttataaagat catgacatcg attacaagga tgacgatgac    4200
```
aaggctgcag ga                                                     4212

<210> SEQ ID NO 26
<211> LENGTH: 1368
<212> TYPE: PRT
<213> ORGANISM: Artificial Sequence
<220> FEATURE:
<223> OTHER INFORMATION: Synthetic polypeptide

<400> SEQUENCE: 26

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350
```

```
Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
```

```
                770             775             780
Glu Glu Gly Ile Lys Glu Leu Gly Ser Gln Ile Leu Lys Glu His Pro
785             790             795             800
Val Glu Asn Thr Gln Leu Gln Asn Glu Lys Leu Tyr Leu Tyr Tyr Leu
                805             810             815
Gln Asn Gly Arg Asp Met Tyr Val Asp Gln Glu Leu Asp Ile Asn Arg
                820             825             830
Leu Ser Asp Tyr Asp Val Asp His Ile Val Pro Gln Ser Phe Leu Lys
                835             840             845
Asp Asp Ser Ile Asp Asn Lys Val Leu Thr Arg Ser Asp Lys Asn Arg
                850             855             860
Gly Lys Ser Asp Asn Val Pro Ser Glu Glu Val Val Lys Lys Met Lys
865             870             875             880
Asn Tyr Trp Arg Gln Leu Leu Asn Ala Lys Leu Ile Thr Gln Arg Lys
                885             890             895
Phe Asp Asn Leu Thr Lys Ala Glu Arg Gly Gly Leu Ser Glu Leu Asp
                900             905             910
Lys Ala Gly Phe Ile Lys Arg Gln Leu Val Glu Thr Arg Gln Ile Thr
                915             920             925
Lys His Val Ala Gln Ile Leu Asp Ser Arg Met Asn Thr Lys Tyr Asp
                930             935             940
Glu Asn Asp Lys Leu Ile Arg Glu Val Lys Val Ile Thr Leu Lys Ser
945             950             955             960
Lys Leu Val Ser Asp Phe Arg Lys Asp Phe Gln Phe Tyr Lys Val Arg
                965             970             975
Glu Ile Asn Asn Tyr His His Ala His Asp Ala Tyr Leu Asn Ala Val
                980             985             990
Val Gly Thr Ala Leu Ile Lys Lys Tyr Pro Lys Leu Glu Ser Glu Phe
                995             1000            1005
Val Tyr Gly Asp Tyr Lys Val Tyr Asp Val Arg Lys Met Ile Ala
    1010            1015            1020
Lys Ser Glu Gln Glu Ile Gly Lys Ala Thr Ala Lys Tyr Phe Phe
    1025            1030            1035
Tyr Ser Asn Ile Met Asn Phe Phe Lys Thr Glu Ile Thr Leu Ala
    1040            1045            1050
Asn Gly Glu Ile Arg Lys Arg Pro Leu Ile Glu Thr Asn Gly Glu
    1055            1060            1065
Thr Gly Glu Ile Val Trp Asp Lys Gly Arg Asp Phe Ala Thr Val
    1070            1075            1080
Arg Lys Val Leu Ser Met Pro Gln Val Asn Ile Val Lys Lys Thr
    1085            1090            1095
Glu Val Gln Thr Gly Gly Phe Ser Lys Glu Ser Ile Leu Pro Lys
    1100            1105            1110
Arg Asn Ser Asp Lys Leu Ile Ala Arg Lys Lys Asp Trp Asp Pro
    1115            1120            1125
Lys Lys Tyr Gly Gly Phe Asp Ser Pro Thr Val Ala Tyr Ser Val
    1130            1135            1140
Leu Val Val Ala Lys Val Glu Lys Gly Lys Ser Lys Lys Leu Lys
    1145            1150            1155
Ser Val Lys Glu Leu Leu Gly Ile Thr Ile Met Glu Arg Ser Ser
    1160            1165            1170
Phe Glu Lys Asn Pro Ile Asp Phe Leu Glu Ala Lys Gly Tyr Lys
    1175            1180            1185
```

| | | | | | | | | | | |
|---|---|---|---|---|---|---|---|---|---|---|
|Glu|Val|Lys|Lys|Asp|Leu|Ile|Ile|Lys|Leu|Pro|Lys|Tyr|Ser|Leu|
| |1190| | | |1195| | | |1200| |

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 27
<211> LENGTH: 4107
<212> TYPE: DNA
<213> ORGANISM: Streptococcus pyogenes

<400> SEQUENCE: 27

```
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tataggggct cttttatttg acagtggaga gacagcggaa     180
gcgactcgtc tcaaacggac agctcgtaga aggtatacac gtcggaagaa tcgtatttgt     240
tatctacagg agatttttc aaatgagatg gcgaaagtag atgatagttt ctttcatcga     300
cttgaagagt ctttttggt ggaagaagac aagaagcatg aacgtcatcc tattttttgga    360 aatatagtag atgaagttgc ttatcatgag aaatatccaa ctatctatca tctgcgaaaa     420
aaattggtag attctactga taaagcggat tgcgcttaa tctatttggc cttagcgcat     480
atgattaagt tcgtggtca ttttttgatt gagggagatt aaatcctga ataatagtgat      540 gtggacaaac tatttatcca gttggtacaa acctacaatc aattatttga gaaaaccct      600 attaacgcaa gtggagtaga tgctaaagcg attctttctg cacgattgag taaatcaaga    660
cgattagaaa atctcattgc tcagctcccc ggtgagaaga aaatggctt atttgggaat     720 ctcattgctt tgtcattggg tttgaccccc aattttaaat caattttga tttggcagaa     780 gatgctaaat tacagctttc aaaagatact tacgatgatg atttagataa ttttattggcg     840 caaattggag atcaatatgc tgatttgttt ttggcagcta agaattttatc agatgctatt     900 ttactttcag atatcctaag agtaaatact gaaataacta ggctccct atcagcttca      960 atgattaaac gctacgatga acatcatcaa gacttgactc ttttaaaagc tttagttcga    1020
```

```
caacaacttc cagaaaagta taaagaaatc ttttttgatc aatcaaaaaa cggatatgca    1080
ggttatattg atgggggagc tagccaagaa gaattttata aatttatcaa accaatttta    1140
gaaaaaatgg atggtactga ggaattattg gtgaaactaa atcgtgaaga tttgctgcgc    1200
aagcaacgga cctttgacaa cggctctatt ccccatcaaa ttcacttggg tgagctgcat    1260
gctattttga gaagacaaga agactttat ccattttaa aagacaatcg tgagaagatt    1320
gaaaaaatct tgacttttcg aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc agctcaatca tttattgaac gcatgacaaa ctttgataaa    1500
aatcttccaa atgaaaaagt actaccaaaa catagtttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
gttaagcaat taaagaaga ttatttcaaa aaaatagaat gttttgatag tgttgaaatt    1740
tcaggagttg aagatagatt taatgcttca ttaggtacct accatgattt gctaaaaatt    1800
attaaagata aagattttt ggataatgaa gaaatgaag atatcttaga ggatattgtt    1860
ttaacattga ccttatttga agataggag atgattgagg aaagacttaa aacatatgct    1920
cacctctttg atgataaggt gatgaaacag cttaaacgtc gccgttatac tggttgggga    1980
cgtttgtctc gaaaattgat taatggtatt agggataagc aatctggcaa acaatatta    2040 gattttttga aatcagatgg ttttgccaat cgcaattta tgcagctgat ccatgatgat    2100
agtttgacat ttaagaaga cattcaaaaa gcacaagtgt ctggacaagg cgatagttta    2160
catgaacata ttgcaaattt agctggtagc cctgctatta aaaaaggtat tttacagact    2220 gtaaagttg ttgatgaatt ggtcaaagta atggggcggc ataagccaga aaatatcgtt    2280
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taacttatt cgagaggtta aagtgattac cttaaaatct    2880
aaattagttt ctgacttccg aaaagatttc aattctata aagtacgtga gattaacaat    2940
taccatcatg cccatgatgc gtatctaaat gccgtcgttg gaactgcttt gattaagaaa    3000
tatccaaaac ttgaatcgga gtttgtctat ggtgattata agtttatga tgttcgtaaa    3060 atgattgcta agtctgagca agaaataggc aaagcaaccg caaaatattt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
```

-continued

```
tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540 ttttagaag ctaaaggata taaggaagtt aaaaaagact taatcattaa actacctaaa     3600
tatagtcttt ttgagttaga aaacggtcgt aaacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta acgatatac gtctacaaaa     4020 gaagttttag atgccactct tatccatcaa tccatcactg gtctttatga aacacgcatt    4080
gatttgagtc agctaggagg tgactga                                        4107
```

<210> SEQ ID NO 28
<211> LENGTH: 1368
<212> TYPE: PRT
<213> ORGANISM: Streptococcus pyogenes

<400> SEQUENCE: 28

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
```

```
            245                 250                 255
Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280             285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670
```

```
Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
    995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080
```

```
Arg Lys Val Leu Ser Met Pro Gln Val Asn Ile Val Lys Lys Thr
    1085            1090                1095

Glu Val Gln Thr Gly Gly Phe Ser Lys Glu Ser Ile Leu Pro Lys
    1100            1105                1110

Arg Asn Ser Asp Lys Leu Ile Ala Arg Lys Lys Asp Trp Asp Pro
    1115            1120                1125

Lys Lys Tyr Gly Gly Phe Asp Ser Pro Thr Val Ala Tyr Ser Val
    1130            1135                1140

Leu Val Val Ala Lys Val Glu Lys Gly Lys Ser Lys Lys Leu Lys
    1145            1150                1155

Ser Val Lys Glu Leu Leu Gly Ile Thr Ile Met Glu Arg Ser Ser
    1160            1165                1170

Phe Glu Lys Asn Pro Ile Asp Phe Leu Glu Ala Lys Gly Tyr Lys
    1175            1180                1185

Glu Val Lys Lys Asp Leu Ile Ile Lys Leu Pro Lys Tyr Ser Leu
    1190            1195                1200

Phe Glu Leu Glu Asn Gly Arg Lys Arg Met Leu Ala Ser Ala Gly
    1205            1210                1215

Glu Leu Gln Lys Gly Asn Glu Leu Ala Leu Pro Ser Lys Tyr Val
    1220            1225                1230

Asn Phe Leu Tyr Leu Ala Ser His Tyr Glu Lys Leu Lys Gly Ser
    1235            1240                1245

Pro Glu Asp Asn Glu Gln Lys Gln Leu Phe Val Glu Gln His Lys
    1250            1255                1260

His Tyr Leu Asp Glu Ile Ile Glu Gln Ile Ser Glu Phe Ser Lys
    1265            1270                1275

Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 29
<211> LENGTH: 1368
<212> TYPE: PRT
<213> ORGANISM: Artificial Sequence
<220> FEATURE:
<223> OTHER INFORMATION: Synthetic polypeptide

<400> SEQUENCE: 29

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60
```

```
Lys Arg Thr Ala Arg Arg Tyr Thr Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
```

```
                485                 490                 495
Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910
```

-continued

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

```
Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
            1355                1360                1365
```

<210> SEQ ID NO 30
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 30

```
Met Thr Ser Glu Lys Gly Pro Ser Thr Gly Asp Pro Thr Leu Arg Arg
1               5                   10                  15

Arg Ile Glu Pro Trp Glu Phe Asp Val Phe Tyr Asp Pro Arg Glu Leu
            20                  25                  30

Arg Lys Glu Ala Cys Leu Leu Tyr Glu Ile Lys Trp Gly Met Ser Arg
        35                  40                  45

Lys Ile Trp Arg Ser Ser Gly Lys Asn Thr Thr Asn His Val Glu Val
50                  55                  60

Asn Phe Ile Lys Lys Phe Thr Ser Glu Arg Asp Phe His Pro Ser Met
65                  70                  75                  80

Ser Cys Ser Ile Thr Trp Phe Leu Ser Trp Ser Pro Cys Trp Glu Cys
                85                  90                  95

Ser Gln Ala Ile Arg Glu Phe Leu Ser Arg His Pro Gly Val Thr Leu
            100                 105                 110

Val Ile Tyr Val Ala Arg Leu Phe Trp His Met Asp Gln Gln Asn Arg
        115                 120                 125

Gln Gly Leu Arg Asp Leu Val Asn Ser Gly Val Thr Ile Gln Ile Met
    130                 135                 140

Arg Ala Ser Glu Tyr Tyr His Cys Trp Arg Asn Phe Val Asn Tyr Pro
145                 150                 155                 160

Pro Gly Asp Glu Ala His Trp Pro Gln Tyr Pro Pro Leu Trp Met Met
                165                 170                 175

Leu Tyr Ala Leu Glu Leu His Cys Ile Ile Leu Ser Leu Pro Pro Cys
            180                 185                 190

Leu Lys Ile Ser Arg Arg Trp Gln Asn His Leu Thr Phe Phe Arg Leu
        195                 200                 205

His Leu Gln Asn Cys His Tyr Gln Thr Ile Pro Pro His Ile Leu Leu
    210                 215                 220

Ala Thr Gly Leu Ile His Pro Ser Val Ala Trp Arg
225                 230                 235
```

<210> SEQ ID NO 31
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 31

```
Gly Gly Gly Ser Gly Gly Gly Ser Gly Gly Gly Ser Gly Gly Gly Ser
1               5                   10                  15
```

Gly Gly Gly Ser Gly Gly Gly Ser Gly Gly Gly Ser
            20                  25                  30

Gly Gly Gly Ser Gly Gly Gly Ser Gly Gly Gly Ser
            35                  40                  45

Gly Gly Gly Ser Gly Gly Gly Ser Gly Gly Gly Ser
    50                  55                  60

Gly Gly Gly Ser Gly Gly Gly Ser Gly Gly Gly Ser
65                  70                  75                  80

Gly Gly Gly Ser Gly Gly Gly Ser Gly Gly Gly Ser
            85                  90                  95

Gly Gly Gly Ser Gly Gly Gly Ser Gly Gly Gly Ser
            100                 105                 110

Gly Gly Gly Ser Gly Gly Gly Ser
        115                 120

<210> SEQ ID NO 32
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 32

Gly Gly Gly Gly Ser Gly Gly Gly Gly Ser Gly Gly Gly Ser Gly
1               5                   10                  15

Gly Gly Ser Gly Gly Gly Gly Ser Gly Gly Gly Ser Gly Gly
            20                  25                  30

Gly Gly Ser Gly Gly Gly Gly Ser Gly Gly Gly Ser Gly Gly
        35                  40                  45

Gly Ser Gly Gly Gly Gly Ser Gly Gly Gly Ser Gly Gly Gly
    50                  55                  60

Ser Gly Gly Gly Gly Ser Gly Gly Gly Ser Gly Gly Gly Ser
65                  70                  75                  80

Gly Gly Gly Gly Ser Gly Gly Gly Ser Gly Gly Gly Ser Gly
            85                  90                  95

Gly Gly Gly Ser Gly Gly Gly Ser Gly Gly Gly Ser Gly Gly
            100                 105                 110

Gly Gly Ser Gly Gly Gly Ser Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Gly Ser
145                 150

<210> SEQ ID NO 33
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 33

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Glu Ala Ala Ala Lys Glu Ala Ala

```
                35                  40                  45
Ala Lys Glu Ala Ala Ala Lys Glu Ala Ala Ala Lys Glu Ala Ala
 50                  55                  60
Lys Glu Ala Ala Ala Lys Glu Ala Ala Ala Lys Glu Ala Ala Lys
 65                  70                  75                  80
Glu Ala Ala Ala Lys Glu Ala Ala Ala Lys Glu Ala Ala Lys Glu
                 85                  90                  95
Ala Ala Ala Lys Glu Ala Ala Lys Glu Ala Ala Lys Glu Ala
            100                 105                 110
Ala Ala Lys Glu Ala Ala Lys Glu Ala Ala Lys Glu Ala Ala
        115                 120                 125
Ala Lys Glu Ala Ala Lys Glu Ala Ala Lys Glu Ala Ala Ala
    130                 135                 140
Lys Glu Ala Ala Ala Lys
145                 150

<210> SEQ ID NO 34
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 34

Ser Gly Ser Glu Thr Pro Gly Thr Ser Glu Ser Ala Thr Pro Glu Ser
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 35

Pro Lys Lys Lys Arg Lys Val
1               5

<210> SEQ ID NO 36
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 36

Met Asp Ser Leu Leu Met Asn Arg Arg Lys Phe Leu Tyr Gln Phe Lys
1               5                   10                  15
Asn Val Arg Trp Ala Lys Gly Arg Arg Glu Thr Tyr Leu Cys
            20                  25                  30

<210> SEQ ID NO 37
<211> LENGTH: 81
<212> TYPE: RNA
<213> ORGANISM: Artificial Sequence
<220> FEATURE:
<223> OTHER INFORMATION: Synthetic polypeptide

<400> SEQUENCE: 37
guuuuagagc uagaaauagc aaguuaaaau aaggcuaguc cguuaucaac uugaaaaagu     60
ggcaccgagu cggugcuuuu u                                              81
```

<210> SEQ ID NO 38
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 38

Met Lys Lys Leu Leu Pro Ala Ile Pro
1               5

<210> SEQ ID NO 39
<211> LENGTH: 414
<212> TYPE: PRT
<213> ORGANISM: Artificial Sequence
<220> FEATURE:
<223> OTHER INFORMATION: Synthetic polypeptide

<400> SEQUENCE: 39

Val Val Pro Phe Tyr Ser His Ser Ala Glu Thr Val Glu Ser Cys Leu
1               5                   10                  15

Ala Lys Pro His Thr Glu Asn Ser Phe Thr Asn Val Trp Lys Asp Asp
                20                  25                  30

Lys Thr Leu Asp Arg Tyr Ala Asn Tyr Glu Gly Cys Leu Trp Asn Ala
            35                  40                  45

Thr Gly Val Val Val Cys Thr Gly Asp Glu Thr Gln Cys Tyr Gly Thr
        50                  55                  60

Trp Val Pro Ile Gly Leu Ala Ile Pro Glu Asn Glu Gly Gly Ser
65                  70                  75                  80

Glu Gly Gly Gly Ser Glu Gly Gly Gly Ser Glu Gly Gly Thr Lys
                85                  90                  95

Pro Pro Glu Tyr Gly Asp Thr Pro Ile Pro Gly Tyr Thr Tyr Ile Asn
                100                 105                 110

Pro Leu Asp Gly Thr Tyr Pro Pro Gly Thr Glu Gln Asn Pro Ala Asn
            115                 120                 125

Pro Asn Pro Ser Leu Glu Glu Ser Gln Pro Leu Asn Thr Phe Met Phe
        130                 135                 140

Gln Asn Asn Arg Phe Arg Asn Arg Gln Gly Ala Leu Thr Val Tyr Thr
145                 150                 155                 160

Gly Thr Val Thr Gln Gly Thr Asp Pro Val Lys Thr Tyr Tyr Gln Tyr
                165                 170                 175

Thr Pro Val Ser Ser Lys Ala Met Tyr Asp Ala Tyr Trp Asn Gly Lys
            180                 185                 190

Phe Arg Asp Cys Ala Phe His Ser Gly Phe Asn Glu Asp Pro Phe Val
        195                 200                 205

Cys Glu Tyr Gln Gly Gln Ser Ser Asp Leu Pro Gln Pro Pro Val Asn
    210                 215                 220

Ala Gly Gly Gly Ser Gly Gly Ser Gly Gly Gly Ser Glu Gly Gly
225                 230                 235                 240

Gly Ser Glu Gly Gly Gly Ser Glu Gly Gly Gly Ser Glu Gly Gly Gly
                245                 250                 255

Ser Gly Gly Gly Ser Gly Ser Gly Asp Phe Asp Tyr Glu Lys Met Ala
            260                 265                 270

Asn Ala Asn Lys Gly Ala Met Thr Glu Asn Ala Asp Glu Asn Ala Leu
        275                 280                 285

Gln Ser Asp Ala Lys Gly Lys Leu Asp Ser Val Ala Thr Asp Tyr Gly
    290                 295                 300

```
Ala Ala Ile Asp Gly Phe Ile Gly Asp Val Ser Gly Leu Ala Asn Gly
305                 310                 315                 320

Asn Gly Ala Thr Gly Asp Phe Ala Gly Ser Asn Ser Gln Met Ala Gln
            325                 330                 335

Val Gly Asp Gly Asp Asn Ser Pro Leu Met Asn Asn Phe Arg Gln Tyr
        340                 345                 350

Leu Pro Ser Leu Pro Gln Ser Val Glu Cys Arg Pro Phe Val Phe Gly
            355                 360                 365

Ala Gly Lys Pro Tyr Glu Phe Ser Ile Asp Cys Asp Lys Ile Asn Leu
        370                 375                 380

Phe Arg Gly Val Phe Ala Phe Leu Leu Tyr Val Ala Thr Phe Met Tyr
385                 390                 395                 400

Val Phe Ser Thr Phe Ala Asn Ile Leu Arg Asn Lys Glu Ser
                405                 410
```

<210> SEQ ID NO 40
<211> LENGTH: 32
<212> TYPE: DNA
<213> ORGANISM: Artificial Sequence
<220> FEATURE:
<223> OTHER INFORMATION: Synthetic polypeptide

<400> SEQUENCE: 40
taatggaaac ttcctcatga aaaagtcttt ag         32

<210> SEQ ID NO 41
<211> LENGTH: 30
<212> TYPE: DNA
<213> ORGANISM: Artificial Sequence
<220> FEATURE:
<223> OTHER INFORMATION: Synthetic polypeptide

<400> SEQUENCE: 41
acagagagaa taacataaaa acagggaagc         30

<210> SEQ ID NO 42
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 42

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Phe Asn Val Pro Phe Tyr Ser His Ser Ala
        35                  40                  45

Glu Thr Val Glu Ser Cys Leu Ala Lys Pro His Thr Glu Asn Ser Phe
    50                  55                  60

Thr Asn Val Trp Lys Asp Asp Lys Thr Leu Asp Arg Tyr Ala Asn Tyr
65              70                  75                  80

Glu Gly Cys Leu Trp Asn Ala Thr Gly Val Val Cys Thr Gly Asp
            85                  90                  95

Glu Thr Gln Cys Tyr Gly Thr Trp Val Pro Ile Gly Leu Ala Ile Pro
            100                 105                 110

Glu Asn Glu Gly Gly Gly Ser Glu Gly Gly Gly Ser Glu Gly Gly Gly
            115                 120                 125
```

Ser Glu Gly Gly Gly Thr Lys Pro Pro Glu Tyr Gly Asp Thr Pro Ile
130                 135                 140

Pro Gly Tyr Thr Tyr Ile Asn Pro Leu Asp Gly Thr Tyr Pro Pro Gly
145                 150                 155                 160

Thr Glu Gln Asn Pro Ala Asn Pro Asn Pro Ser Leu Glu Glu Ser Gln
                165                 170                 175

Pro Leu Asn Thr Phe Met Phe Gln Asn Asn Arg Phe Arg Asn Arg Gln
            180                 185                 190

Gly Ala Leu Thr Val Tyr Thr Gly Thr Val Thr Gln Gly Thr Asp Pro
        195                 200                 205

Val Lys Thr Tyr Tyr Gln Tyr Thr Pro Val Ser Ser Lys Ala Met Tyr
    210                 215                 220

Asp Ala Tyr Trp Asn Gly Lys Phe Arg Asp Cys Ala Phe His Ser Gly
225                 230                 235                 240

Phe Asn Glu Asp Pro Phe Val Cys Glu Tyr Gln Gly Gln Ser Ser Asp
                245                 250                 255

Leu Pro Gln Pro Pro Val Asn Ala Gly Gly Ser Gly Gly Gly Ser
            260                 265                 270

Gly Gly Gly Ser Glu Gly Gly Ser Glu Gly Gly Ser Glu Gly
        275                 280                 285

Gly Gly Ser Glu Gly Gly Ser Gly Gly Ser Gly Ser Gly Asp
        290                 295                 300

Phe Asp Tyr Glu Lys Met Ala Asn Ala Asn Lys Gly Ala Met Thr Glu
305                 310                 315                 320

Asn Ala Asp Glu Asn Ala Leu Gln Ser Asp Ala Lys Lys Leu Asp
                325                 330                 335

Ser Val Ala Thr Asp Tyr Gly Ala Ala Ile Asp Gly Phe Ile Gly Asp
            340                 345                 350

Val Ser Gly Leu Ala Asn Gly Asn Gly Ala Thr Gly Asp Phe Ala Gly
        355                 360                 365

Ser Asn Ser Gln Met Ala Gln Val Gly Asp Gly Asp Asn Ser Pro Leu
370                 375                 380

Met Asn Asn Phe Arg Gln Tyr Leu Pro Ser Leu Pro Gln Ser Val Glu
385                 390                 395                 400

Cys Arg Pro Phe Val Phe Gly Ala Gly Lys Pro Tyr Glu Phe Ser Ile
                405                 410                 415

Asp Cys Asp Lys Ile Asn Leu Phe Arg Gly Val Phe Ala Phe Leu Leu
            420                 425                 430

Tyr Val Ala Thr Phe Met Tyr Val Phe Ser Thr Phe Ala Asn Ile Leu
        435                 440                 445

Arg Asn Lys Glu Ser
    450

<210> SEQ ID NO 43
<211> LENGTH: 23
<212> TYPE: DNA
<213> ORGANISM: Artificial Sequence
<220> FEATURE:
<223> OTHER INFORMATION: Synthetic polypeptide

<400> SEQUENCE: 43
tgcccctccc tccctggccc agg                                        23

<210> SEQ ID NO 44
<211> LENGTH: 23

```
<212> TYPE: DNA
<213> ORGANISM: Artificial Sequence
<220> FEATURE:
<223> OTHER INFORMATION: Synthetic polypeptide

<400> SEQUENCE: 44
ggaatccctt ctgcagcacc tgg                                             23

<210> SEQ ID NO 45
<211> LENGTH: 23
<212> TYPE: DNA
<213> ORGANISM: Artificial Sequence
<220> FEATURE:
<223> OTHER INFORMATION: Synthetic polypeptide

<400> SEQUENCE: 45
gaacacaaag catagactgc ggg                                             23

<210> SEQ ID NO 46
<211> LENGTH: 23
<212> TYPE: DNA
<213> ORGANISM: Artificial Sequence
<220> FEATURE:
<223> OTHER INFORMATION: Synthetic polypeptide

<400> SEQUENCE: 46
ggcccagact gagcacgtga tgg                                             23

<210> SEQ ID NO 47
<211> LENGTH: 23
<212> TYPE: DNA
<213> ORGANISM: Artificial Sequence
<220> FEATURE:
<223> OTHER INFORMATION: Synthetic polypeptide

<400> SEQUENCE: 47
ggcactgcgg ctggaggtgg ggg                                             23

<210> SEQ ID NO 48
<211> LENGTH: 23
<212> TYPE: DNA
<213> ORGANISM: Artificial Sequence
<220> FEATURE:
<223> OTHER INFORMATION: Synthetic polypeptide

<400> SEQUENCE: 48
gtcatcttag tcattacctg agg                                             23
```

EVOLUTION OF CYTIDINE DEAMINASES

RELATED APPLICATIONS

This application is a national stage filing under 35 U.S.C. § 371 of international PCT application, PCT/US2019/037216, filed Jun. 14, 2019, which claims priority under 35 U.S.C. § 119(e) to U.S. Provisional Application Ser. No. 62/685,252, filed Jun. 14, 2018, entitled "Evolution of Cytidine Deaminases," each of which is incorporated herein by reference.

GOVERNMENT SUPPORT

This invention was made with government support under grant numbers GM118062, GM119228, EB022376, and HG009490, awarded by the National Institutes of Health. The government has certain rights in the invention.

BACKGROUND

Targeted editing of nucleic acid sequences, for example, the targeted cleavage or the targeted introduction of a specific modification into genomic DNA, is a highly promising approach for the study of gene function and also has the potential to provide new therapies for human genetic diseases. One drawback to the current technologies is that both NHEJ and HDR are stochastic processes that typically result in modest gene editing efficiencies as well as unwanted gene alterations that can compete with the desired alteration. Since many genetic diseases in principle can be treated by effecting a specific nucleotide change at a specific location in the genome (for example, a C to T change in a specific codon of a gene associated with a disease), the development of a programmable way to achieve such precision gene editing would represent both a powerful new research tool, as well as a potential new approach to gene editing-based human therapeutics.

Soluble protein expression is a desirable characteristic for the production and application of gene editing proteins. It is estimated that <50% of bacterial and <15% of non-bacterial proteins can be recombinantly expressed in soluble form in *E. coli*. However, many of these recombinantly expressed proteins either undergo proteolysis or are misfold into inclusion bodies. Moreover, engineering or evolving proteins towards improved or novel function can often lead to reduced soluble expression, impeding the development and application of proteins with tailor-made functional properties.

In addition to the challenge associated with simultaneously yet independently selecting for soluble expression and protein function, traditional directed evolution approaches to improving protein expression introduce additional drawbacks, including substantial time and effort requirements. Each round of traditional laboratory protein evolution can take a week or longer, rendering the prospect of evolving improvements in soluble expression in addition to new or improved functions an unattractive one. As a result, otherwise interesting targets for protein evolution are often not pursued due to the intractability of expression under standard laboratory conditions. A system that allows for the rapid improvement of protein expression, coupled with the preservation or improvement of protein function would therefore offer substantial benefits.

SUMMARY

Cytidine deaminase proteins have been observed to be useful for correcting T to C mutations in genes associated with disease, for example, as described in International PCT Application No. PCT/US2016/058344, published on Apr. 27, 2017 as WO 2017/070632, the entire contents of which are incorporated herein by reference. However, certain cytidine deaminase proteins (e.g., apolipoprotein B mRNA editing catalytic subunit 1 (APOBEC1) proteins, such as rat APOBEC1) express poorly in *E. coli* and localize almost exclusively to the insoluble fraction, making recombinant production of such proteins difficult.

Some aspects of this disclosure relate to compositions (e.g., isolated nucleic acids, vectors, protein variants, etc.), and methods for improving physiochemical properties (e.g., thermostability, solubility, catalytic activity, etc.) of cytidine deaminase proteins using Phage-Assisted Continuous Evolution (PACE). Phage-assisted continuous evolution (PACE) can serve as a rapid, high-throughput system for evolving genes of interest. One advantage of the PACE technology is that both the time and human effort required to evolve a gene of interest are dramatically decreased as compared to conventional iterative evolution methods. During PACE, a phage vector carrying a gene encoding a gene of interest replicates in a flow of host cells through a fixed-volume vessel (a "lagoon"). For example, in some embodiments of PACE described herein, a population of bacteriophage vectors replicates in a continuous flow of bacterial host cells through the lagoon, wherein the flow rate of the host cells is adjusted so that the average time a host cell remains in the lagoon is shorter than the average time required for host cell division, but longer than the average life cycle of the vector, e.g., shorter than the average M13 bacteriophage life cycle. As a result, the population of vectors replicating in the lagoon can be varied by inducing mutations, and then enriching the population for desired variants by applying selective pressure, while the host cells do not effectively replicate in the lagoon.

Some aspects of this disclosure relate to systems for improving the stability and/or solubility of cytidine deaminase proteins evolved during PACE, and are referred to in some embodiments as evolution of cytidine deaminase proteins using Soluble Expression PACE (SE-PACE). The systems, including recombinant expression constructs, also referred to as vectors if they are in the form of a plasmid, can enhance selection of evolved proteins that are properly folded, have increased stability (e.g., thermodynamic stability), and/or solubility (e.g., enhanced soluble expression in bacteria, such as *E. coli*) while maintaining desired protein function. SE-PACE is generally described in U.S. Provisional Application Ser. No. 62/559,919, filed Sep. 18, 2017, the entire contents of which are incorporated herein by reference. In some aspects, the disclosure relates to cytidine deaminase protein variants that are produced using SE-PACE.

In some aspects, the disclosure relates to a cytidine deaminase protein (e.g., cytidine deaminase protein variant) comprising an amino acid sequence that is at least 90% identical to a cytidine deaminase protein (for example an APOBEC protein, such as a rat APOBEC protein, rAPOBEC1, SEQ ID NO: 15), wherein the amino acid sequence includes at least one mutation occurring at a position selected from R33, G45, N57, N65, Y75, T101, F113, F113, A123, S149, A165, H166, T204, F205, and W224, or at a corresponding position in another cytidine deaminase.

In some embodiments, an amino acid sequence encoding a cytidine deaminase protein is at least 96%, at least 97%, at least 98%, or at least 99% identical to SEQ ID NO: 15

In some embodiments, a cytidine deaminase protein variant includes at least one of the following mutations: R33C, G45D, N57S, N65D, Y75H, T101, F113C, F113R, A123E, S149Y, A165T, H166N, T204P, F205S, or W224R.

In some embodiments, a cytidine deaminase protein variant does not comprise a mutation at position E63.

In some embodiments, the amino acid sequence of a cytidine deaminase protein variant includes mutations at positions F113, A123, and F205. In some embodiments, the amino acid sequence of a cytidine deaminase protein variant includes mutations at positions F113C, A123E, and F205S. In some embodiments, the amino acid sequence of a cytidine deaminase protein variant is represented by SEQ ID NO: 16.

In some embodiments, the amino acid sequence of a cytidine deaminase protein variant includes mutations at positions G45, Y75, F113, A123, H166, and F205. In some embodiments, the amino acid sequence of a cytidine deaminase protein variant includes mutations at positions G45D, Y75H, F113C, A123E, H166N, and F205S. In some embodiments, the amino acid sequence of a cytidine deaminase protein variant is represented by SEQ ID NO: 17.

In some embodiments, the amino acid sequence of a cytidine deaminase protein variant includes mutations at positions F113, A123, A165, and F205. In some embodiments, the amino acid sequence of a cytidine deaminase protein variant includes mutations at positions F113C, A123E, A165T, and F205S. In some embodiments, the amino acid sequence of a cytidine deaminase protein variant is represented by SEQ ID NO: 19.

In some aspects, the disclosure relates to an isolated nucleic acid encoding a cytidine deaminase protein variant as described by the disclosure. In some embodiments, an isolated nucleic acid comprises or consists of the sequence set forth in any one of SEQ ID NOs: 7, 8, or 10. In some embodiments, an isolated nucleic acid comprises or consists of a sequence that is at least 70%, at least 80%, at least 90%, at least 95%, or at least 99% identical to the sequence set forth in any one of SEQ ID NOs: 7, 8, or 10.

In some embodiments, an isolated nucleic acid is codon optimized for expression (e.g., optimized for expression in E. coli cells or mammalian cells). In some embodiments, and isolated nucleic acid comprises or consists of the sequence set forth in any one of SEQ ID NOs: 12-14. In some embodiments, an isolated nucleic acid comprises or consists of a sequence that is at least 70%, at least 80%, at least 90%, at least 95%, or at least 99% identical to the sequence set forth in any one of SEQ ID NOs: 12-14.

In some aspects, the disclosure relates to a host cell comprising a cytidine deaminase protein variant as described by the disclosure. In some aspects, the disclosure relates to an isolated nucleic acid as described by the disclosure. In some embodiments, a host cell is a bacterial cell. In some aspects, a host cell is a mammalian cell. In some embodiments, a bacterial cell is an E. coli cell. In some embodiments, a mammalian cell is a human cell.

In some aspects, the disclosure relates to a fusion protein comprising: (i) a RNA-programmable nuclease (e.g., a Cas9 domain); and (ii) a cytosine deaminase protein variant as described by the disclosure. In some embodiments, a fusion protein further comprises (iii) a uracil glycosylase inhibitor (UGI) domain.

In some embodiments, a RNA-programmable nuclease (e.g. a Cas9 domain) comprises an amino acid sequence that is at least 85% identical to the amino acid sequence provided in SEQ ID NO: 20.

In some embodiments, a Cas9 domain is a Cas9 nickase domain that cuts a nucleotide target strand of a nucleotide duplex, wherein the nucleotide target strand is the strand that binds to a gRNA of the Cas9 nickase domain, for example as provided in SEQ ID NO: 21.

In some embodiments, a UGI domain comprises a domain capable of inhibiting Uracil DNA Glycosylase (UDG) activity. In some embodiments, a UGI domain comprises an amino acid sequence that is at least 85% identical to SEQ ID NO: 22.

In some embodiments, fusion proteins provided herein further comprise a nuclear localization sequence (NLS).

In some aspects, the disclosure relates to a vector system comprising: (i) a selection phagemid comprising an isolated nucleic acid comprising an expression construct encoding a fusion protein comprising, in the following order: a GCN4 peptide, a cytidine deaminase protein, a T7 RNA polymerase, and an E. coli RNA polymerase omega subunit (rpoZ); (ii) a first accessory plasmid comprising an isolated nucleic acid comprising an expression construct encoding a RNA polymerase I promoter operably linked to an expression cassette comprising, in the following order: a sequence encoding a M13 phage gIII protein signal peptide, and a sequence encoding a Npu split intein N-terminal portion, wherein the sequence encoding the gIII protein signal peptide lacks one or more nucleic acid bases of the signal peptide domain; and (iii) a second accessory plasmid comprising an isolated nucleic acid comprising an expression construct encoding a T7 promoter operably linked to an expression cassette comprising, in the following order: a sequence encoding a Npu split intein C-terminal portion, and a sequence encoding a M13 phage gIII protein, wherein the sequence encoding the gIII protein lacks one or more nucleic acid bases in the signal peptide domain.

In some embodiments, a vector system as described by the disclosure further comprises a mutagenesis plasmid.

In some aspects, the disclosure relates to a kit comprising: a first container housing a selection phagemid as described by the disclosure; a second container housing a first accessory plasmid as described by the disclosure; and a third container housing a second accessory plasmid as described by the disclosure.

In some embodiments, a kit further comprises a container housing one or more bacterial cells. In some embodiments, the bacterial cells are E. coli cells.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

FIG. 1A is a schematic depicting a protein of interest (POI) fused between an affinity tag (e.g., a GCN4 peptide) and T7n-rpoZ, allowing both the protein expression and protein binding selections to operate. As the selection phage (SP) carries the GCN4 peptide linked to rpoZ, they begin PACE with the ability to pass the protein binding selection. FIG. 1B is a schematic showing that any selection phage (SP) that cheat by forming truncations in the POI lose the ability to propagate on the protein binding selection, as the GCN4 peptide is no longer connected to rpoZ. Therefore, these phage are expected to wash out of the lagoon.

FIGS. 2A-2C show activity independent SE-PACE of rAPBOEC1. FIG. 2A shows representative data for expression of rAPOBEC and rAPOBEC variants (36.1, 43.1, 43.2rev) in BL21 DE3 cells at 37° C. FIG. 2B shows consensus mutations from SP isolated from lagoons 1 and 2 of first two PACE experiments. FIG. 2C shows mutations in rAPOBEC1 and rAPOBEC1 variants after 370 h of PACE.

FIG. 3A shows representative plaque forming unit (pfu) data from activity independent SE-PACE of cytidine deaminase rAPOBEC1. The stringency of the protein expression selection was modulated through increasing the rate of lagoon dilution (flow rate), as well as the use of activity-diminishing T7 RNAP and T7 promoter mutants in the accessory plasmid (AP). FIG. 3B shows rAPOBEC1 variants obtained after 186 h and 370 h show greatly improved soluble expression at 37° C. when compared to wild-type rAPOBEC1. FIG. 3C shows that Base Editor (BE2) variants employing evolved rAPOBEC1 variants have enhanced apparent activity in $E.$ $coli$, as measured by cells surviving selection on increasing concentrations of chloramphenicol due to BE2-dependent reversion of an active site mutation in chloramphenicol acetyl transferase. Data reflects the mean and s.d. of three technical replicates (unique clones).

FIG. 3D shows data indicating that Base Editor (BE3) variants that include evolved rAPOBEC1 variants 36.1 and 43.1 show enhanced editing efficiency in HEK293T cells. Data reflects the mean and s.e.m. of four biological replicates (experiments performed on different days).

FIG. 4A shows rAPOBEC1 variants from PACE retain deaminase activity in $E.$ $coli$, as measured by cells surviving selection on rifampin. FIG. 4B shows total colony forming units (cfu) from overnight cultures of BL21 cells after induction of rAPOBEC1 variants. Data reflect the mean and s.e.m. of six biological replicates.

DEFINITIONS

Figure 1A:
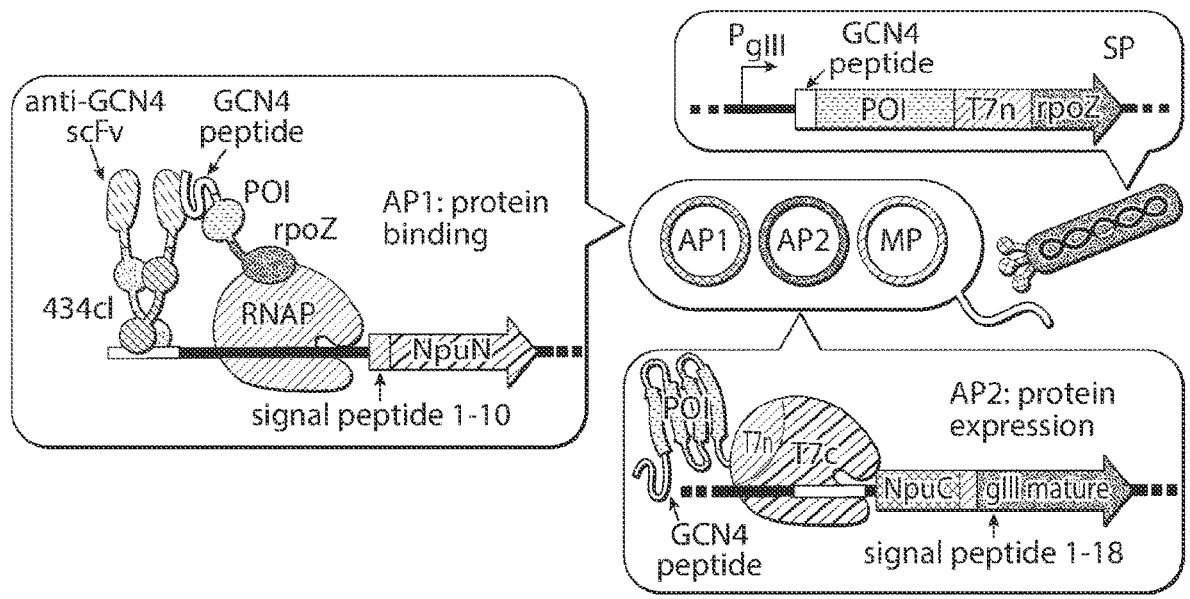
FIGS. 1A-1B show a schematic depicting cheat-resistant, activity-independent selection for protein expression (e.g., activity independent SE-PACE).

The term "phage-assisted continuous evolution (PACE)," as used herein, refers to continuous evolution that employs phage as viral vectors. The general concept of PACE technology has been described, for example, in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; U.S. Pat. No. 9,023,594, issued May 5, 2015, International PCT Application, PCT/US2015/012022, filed Jan. 20, 2015, published as WO 2015/134121 on Sep. 11, 2015, and International PCT Application, PCT/US2016/027795, filed Apr. 15, 2016, published as WO 2016/168631 on Oct. 20, 2016, the entire contents of each of which are incorporated herein by reference.

The term "soluble expression phage-assisted continuous evolution (SE-PACE)," as used herein, refers to continuous evolution that employs a PACE-compatible "AND" gate that uses a split-intein pIII, which renders T7 RNA polymerase (T7 RNAP) activity dependent on the soluble expression of a target protein, and also uses the resulting T7 RNAP activity to drive gene III expression. In some embodiments, SE-PACE allows for two positive selections to take place in the same PACE experiment. The general concept of SE-PACE technology has been described, for example, in U.S. Provisional Application Ser. No. 62/559,919, filed Sep. 18, 2017, the entire contents of which are incorporated herein by reference. One embodiment of a SE-PACE system is described in FIG. 1A.

The term "continuous evolution," as used herein, refers to an evolution process, in which a population of nucleic acids encoding a gene to be evolved is subjected to multiple rounds of (a) replication, (b) mutation, and (c) selection to produce a desired evolved version of the gene to be evolved that is different from the original version of the gene, for example, in that a gene product, such as, e.g., an RNA or protein encoded by the gene, exhibits a new activity not present in the original version of the gene product, or in that an activity of a gene product encoded by the original gene to be evolved is modulated (increased or decreased). The multiple rounds can be performed without investigator intervention, and the steps (a)-(c) can be carried out simultaneously. Typically, the evolution procedure is carried out in vitro, for example, using cells in culture as host cells. In general, a continuous evolution process provided herein relies on a system in which a gene encoding a gene product of interest is provided in a nucleic acid vector that undergoes a life-cycle including replication in a host cell and transfer to another host cell, wherein a critical component of the life-cycle is deactivated and reactivation of the component is dependent upon an activity of the gene to be evolved that is a result of a mutation in the nucleic acid vector.

The term "vector," as used herein, refers to a nucleic acid that can be modified to encode a gene of interest and that is able to enter into a host cell, mutate and replicate within the host cell, and then transfer a replicated form of the vector into another host cell. Exemplary suitable vectors include viral vectors, such as retroviral vectors or bacteriophages, and conjugative plasmids. Additional suitable vectors will be apparent to those of skill in the art based on the instant disclosure.

The term "viral vector," as used herein, refers to a nucleic acid comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene of interest to be evolved.

The term "phage," as used herein interchangeably with the term "bacteriophage," refers to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art and non-limiting examples of phages that are useful for carrying out the methods provided herein are λ(Lysogen), T2, T4, T7, T12, R17, M13, MS2, G4, P1, P2, P4, Phi X174, N4, 16, and Φ29. In certain embodiments, the phage utilized in the present invention is M13. Additional suitable phages and host cells will be apparent to those of skill in the art and the invention is not limited in this aspect. For an exemplary description of additional suitable phages and host cells, see Elizabeth Kutter and Alexander Sulakvelidze: *Bacteriophages: Biology and Applications*. CRC Press; 1$^{st}$ edition (December 2004), ISBN: 0849313368; Martha R. J. Clokie and Andrew M. Kropinski: *Bacteriophages: Methods and Protocols, Volume 1: Isolation, Characterization, and Interactions (Methods in Molecular Biology)* Humana Press; 1$^{st}$ edition (December, 2008), ISBN: 1588296822; Martha R. J. Clokie and Andrew M. Kropinski: *Bacteriophages: Methods and Protocols, Volume 2: Molecular and Applied Aspects (Methods in Molecular Biology)* Humana Press; 1$^{st}$ edition (December 2008), ISBN: 1603275649; all of which are incorporated herein in their entirety by reference for disclosure of suitable phages and host cells as well as methods and protocols for isolation, culture, and manipulation of such phages).

The term "accessory plasmid," as used herein, refers to a plasmid comprising a gene required for the generation of infectious viral particles under the control of a conditional promoter. In the context of continuous evolution of genes, transcription from the conditional promoter of the accessory plasmid is typically activated, directly or indirectly, by a function of the gene to be evolved. Accordingly, the accessory plasmid serves the function of conveying a competitive advantage to those viral vectors in a given population of viral vectors that carry a version of the gene to be evolved able to activate the conditional promoter or able to activate the conditional promoter more strongly than other versions of the gene to be evolved. In some embodiments, only viral vectors carrying an "activating" version of the gene to be evolved will be able to induce expression of the gene required to generate infectious viral particles in the host cell, and, thus, allow for packaging and propagation of the viral genome in the flow of host cells. Vectors carrying non-activating versions of the gene to be evolved, on the other hand, will not induce expression of the gene required to generate infectious viral vectors, and, thus, will not be packaged into viral particles that can infect fresh host cells.

The term "helper phage," as used herein, interchangeable with the terms "helper phagemid" and "helper plasmid," refers to a nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes for the generation of infectious phage particles. Helper phages are useful to allow modified phages that lack a gene for the generation of infectious phage particles to complete the phage life cycle in a host cell. Typically, a helper phage will comprise the genes for the generation of infectious phage particles that are lacking in the phage genome, thus complementing the phage genome. In the continuous evolution context, the helper phage typically complements the selection phage, but both lack a phage gene required for the production of infectious phage particles.

The term "selection phage," as used herein interchangeably with the term "selection plasmid," refers to a modified phage that comprises a nucleic acid sequence encoding a cytidine deaminase to be evolved, and lacks a full-length gene encoding a protein required for the generation of infectious phage particles. For example, some M13 selection phages provided herein comprise a nucleic acid sequence encoding a gene to be evolved, e.g., under the control of an M13 promoter, and lack all or part of a phage gene encoding a protein required for the generation of infectious phage particles, e.g., gI, gII, gIII, gIV, gV, gVI, gVII, gVIII, gIX, or gX, or any combination thereof. For example, some M13 selection phages provided herein comprise a nucleic acid sequence encoding a cytidine deaminase protein to be evolved, e.g., under the control of an M13 promoter, and lack all or part of a gene encoding a protein required for the generation of infective phage particles, e.g., the gIII gene encoding the pIII protein.

The term "mutagenesis plasmid," as used herein, refers to a plasmid comprising a gene encoding a gene product that acts as a mutagen. In some embodiments, the gene encodes a DNA polymerase lacking a proofreading capability. In some embodiments, the gene is a gene involved in the bacterial SOS stress response, for example, a UmuC, UmuD', or RecA gene. In some embodiments, the gene is a GATC methylase gene, for example, a deoxyadenosine methylase (dam methylase) gene. In some embodiments, the gene is involved in binding of hemimethylated GATC sequences, for example, a seqA gene. In some embodiments, the gene is involved with repression of mutagenic nucleobase export, for example emrR. In some embodiments, the gene is involved with inhibition of uracil DNA-glycosylase, for example a Uracil Glycosylase Inhibitor (ugi) gene. In some embodiments, the gene is involved with deamination of cytidine (e.g., a cytidine deaminase from *Petromyzon marinus*), for example, cytidine deaminase 1 (CDA1). Mutagenesis plasmids (also referred to as mutagenesis constructs) are described, for example by International Patent Application, PCT/US2016/027795, filed Apr. 16, 2016, published as WO2016/168631 on Oct. 20, 2016, the entire contents of which are incorporated herein by reference.

The term "nucleic acid," as used herein, refers to a polymer of nucleotides. The polymer may include natural nucleosides (i.e., adenosine, thymidine, guano sine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

The term "protein," as used herein, refers to a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain; see, for example, cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term "evolved deaminase protein," as used herein, refers to a cytidine deaminase protein variant that is expressed by a gene of interest (e.g., a gene encoding a cytidine deaminase protein) that has been subjected to continuous evolution, such as PACE or SE-PACE.

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* (4$^{th}$ ed., Cold Spring Harbor Laboratory Press, Cold Spring Harbor, N.Y. (2012)).

The term "deaminase", "deaminase protein", or "deaminase domain," as used herein, refers to a protein or enzyme that catalyzes a deamination reaction. In some embodiments, the deaminase or deaminase domain is a cytidine deaminase, catalyzing the hydrolytic deamination of cytidine or deoxycytidine to uridine or deoxyuridine, respectively. In some embodiments, the deaminase or deaminase domain is a cytosine deaminase, catalyzing the hydrolytic deamination of cytosine to uracil. In some embodiments, the deaminase or deaminase domain is a naturally-occurring deaminase from an organism, such as a human, chimpanzee, gorilla, monkey, cow, dog, rat, or mouse.

The term "cytidine deaminase protein variant," as used herein, refers to a cytidine deaminase protein having one or more amino acid variations introduced into the amino acid sequence, e.g., as a result of application of the PACE method or SE-PACE method, as compared to the amino acid sequence of a naturally-occurring or wild-type cytidine deaminase protein. Amino acid sequence variations may include one or more mutated residues within the amino acid sequence of the cytidine deaminase protein variant, e.g., as a result of a change in the nucleotide sequence encoding the protein that results in a change in the codon at any particular position in the coding sequence, the deletion of one or more amino acids (e.g., a truncated protein), the insertion of one or more amino acids, or any combination of the foregoing. In some embodiments, the deaminase or deaminase domain variant is a variant of a naturally-occurring deaminase from an organism, that does not occur in nature. In some embodiments, a deaminase variant or deaminase domain variant is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occurring deaminase from an organism.

A "wild-type cytidine deaminase protein" refers to the amino acid sequence of a cytidine deaminase protein as it naturally occurs in the genome of the host from which it is derived. Examples of a wild-type cytidine deaminase proteins include rat apolipoprotein B mRNA editing catalytic subunit 1 (rAPOBEC1), which is represented by the amino acid sequence set forth in SEQ ID NO: 15, and human APOBEC1, which is represented by the amino acid sequence of NCBI Accession Number NP_001291495.1.

The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a nucleic-acid editing protein. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4$^{th}$ ed., Cold Spring Harbor Laboratory Press, Cold Spring Harbor, N.Y. (2012)), the entire contents of which are incorporated herein by reference.

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease:RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is identical or homologous to a tracrRNA as provided in Jinek et al., Science 337:816-821(2012), the entire contents of which is incorporated herein by reference. Other examples of gRNAs (e.g., those including domain 2) can be found in U.S. Provisional Patent Application Ser. No. 61/874,682, filed Sep. 6, 2013, entitled "Switchable Cas9 Nucleases And Uses Thereof," and U.S. Provisional Patent Application Ser. No. 61/874,746, filed Sep. 6, 2013, entitled "Delivery System For Functional Nucleases," the entire contents of each are hereby incorporated by reference in their entirety. In some embodiments, a gRNA comprises two or more of domains (1) and (2), and may be referred to as an "extended gRNA." For example, an extended gRNA will, e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example Cas9 (Csn1) from Streptococcus pyogenes (see, e.g., "Complete genome sequence of an M1 strain of Streptococcus pyogenes." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference.

Because RNA-programmable nucleases (e.g., Cas9) use RNA:DNA hybridization to target DNA cleavage sites, these proteins are able to be targeted, in principle, to any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. Science 339, 819-823 (2013); Mali, P. et al. RNA-guided human genome engineering via Cas9. Science 339, 823-826 (2013); Hwang, W. Y. et al. Efficient genome editing in zebrafish using a CRISPR-Cas system. Nature biotechnology 31, 227-229 (2013); Jinek, M. et al. RNA-programmed genome editing in human cells. eLife 2, e00471 (2013); Dicarlo, J. E. et al. Genome engineering in Saccharomyces cerevisiae using CRISPR-Cas systems. Nucleic acids research (2013); Jiang, W. et al. RNA-guided editing of bacterial genomes using CRISPR-Cas systems. Nature biotechnology 31, 233-239 (2013); the entire contents of each of which are incorporated herein by reference).

The term "Cas9" or "Cas9 nuclease" refers to an RNA-guided nuclease comprising a Cas9 protein, or a fragment thereof (e.g., a protein comprising an active, inactive, or partially active DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. Science 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of Streptococcus pyogenes." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference). Cas9 orthologs have been described in various species, including, but not limited to, S. pyogenes and S. thermophilus. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase.

A nuclease-inactivated Cas9 protein may interchangeably be referred to as a "dCas9" protein (for nuclease-"dead" Cas9). Methods for generating a Cas9 protein (or a fragment thereof) having an inactive DNA cleavage domain are known (See, e.g., Jinek et al., Science. 337:816-821(2012); Qi et al., "Repurposing CRISPR as an RNA-Guided Platform for Sequence-Specific Control of Gene Expression" (2013) Cell. 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., *Science.* 337:816-821(2012); Qi et al., *Cell.* 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to wild type Cas9. In some embodiments, the Cas9 variant may have 1, 2, 3, 4, 5, or more amino acid changes compared to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequence: NC_017053.1, SEQ ID NO: 23 (nucleotide); SEQ ID NO 24 (amino acid)).

(SEQ ID NO: 23)
ATGGATAAGAAATACTCAATAGGCTTAGATATCGGCACAAATAGCGTCGG

ATGGGCGGTGATCACTGATGATTATAAGGTTCCGTCTAAAAAGTTCAAGG

TTCTGGGAAATACAGACCGCCACAGTATCAAAAAAAATCTTATAGGGCT

CTTTTATTTGGCAGTGGAGAGACAGCGGAAGCGACTCGTCTCAAACGGAC

AGCTCGTAGAAGGTATACACGTCGGAAGAATCGTATTTGTTATCTACAGG

AGATTTTTTCAAATGAGATGGCGAAAGTAGATGATAGTTTCTTTCATCGA

CTTGAAGAGTCTTTTTTGGTGGAAGAAGACAAGAAGCATGAACGTCATCC

TATTTTTGGAAATATAGTAGATGAAGTTGCTTATCATGAGAAATATCCAA

CTATCTATCATCTGCGAAAAAAATTGGCAGATTCTACTGATAAAGCGGAT

TTGCGCTTAATCTATTTGGCCTTAGCGCATATGATTAAGTTTCGTGGTCA

TTTTTTGATTGAGGGAGATTTAAATCCTGATAATAGTGATGTGGACAAAC

TATTTATCCAGTTGGTACAAATCTACAATCAATTATTTGAAGAAACCCT

ATTAACGCAAGTAGAGTAGATGCTAAAGCGATTCTTTCTGCACGATTGAG

TAAATCAAGACGATTAGAAAATCTCATTGCTCAGCTCCCCGGTGAGAAGA

GAAATGGCTTGTTTGGGAATCTCATTGCTTTGTCATTGGGATTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTTGGCAGCTAAGAATTTATCAGATGCTATT

TTACTTTCAGATATCCTAAGAGTAAATAGTGAAATAACTAAGGCTCCCCT

ATCAGCTTCAATGATTAAGCGCTACGATGAACATCATCAAGACTTGACTC

-continued

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAGTACTACCAAAACATAGTTTGCTTTATGAGTA

TTTTACGGTTTATAACGAATTGACAAAGGTCAAATATGTTACTGAGGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG

AAGATAGATTTAATGCTTCATTAGGCGCCTACCATGATTTGCTAAAAATT

ATTAAAGATAAAGATTTTTTGGATAATGAAGAAAATGAAGATATCTTAGA

GGATATTGTTTTAACATTGACCTTATTTGAAGATAGGGGGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTTGA

AATCAGATGGTTTTGCCAATCGCAATTTTATGCAGCTGATCCATGATGAT

AGTTTGACATTTAAAGAAGATATTCAAAAAGCACAGGTGTCTGGACAAGG

CCATAGTTTACATGAACAGATTGCTAACTTAGCTGGCAGTCCTGCTATTA

AAAAAGGTATTTTACAGACTGTAAAAATTGTTGATGAACTGGTCAAAGTA

ATGGGGCATAAGCCAGAAAATATCGTTATTGAAATGGCACGTGAAAATCA

GACAACTCAAAAGGGCCAGAAAAATTCGCGAGAGCGTATGAAACGAATCG

AAGAAGGTATCAAAGAATTAGGAAGTCAGATTCTTAAAGAGCATCCTGTT

GAAAATACTCAATTGCAAAATGAAAAGCTCTATCTCTATTATCTACAAAA

TGGAAGAGACATGTATGTGGACCAAGAATTAGATATTAATCGTTTAAGTG

ATTATGATGTCGATCACATTGTTCCACAAAGTTTCATTAAAGACGATTCA

ATAGACAATAAGGTACTAACGCGTTCTGATAAAAATCGTGGTAAATCGGA

TAACGTTCCAAGTGAAGAAGTAGTCAAAAAGATGAAAAACTATTGGAGAC

AACTTCTAAACGCCAAGTTAATCACTCAACGTAAGTTTGATAATTTAACG

AAAGCTGAACGTGGAGGTTTGAGTGAACTTGATAAAGCTGGTTTTATCAA

ACGCCAATTGGTTGAAACTCGCCAAATCACTAAGCATGTGGCACAAATTT

TGGATAGTCGCATGAATACTAAATACGATGAAAATGATAAACTTATTCGA

GAGGTTAAAGTGATTACCTTAAAATCTAAATTAGTTTCTGACTTCCGAAA

AGATTTCCAATTCTATAAAGTACGTGAGATTAACAATTACCATCATGCCC

ATGATGCGTATCTAAATGCCGTCGTTGGAACTGCTTTGATTAAGAAATAT

```
CCAAAACTTGAATCGGAGTTTGTCTATGGTGATTATAAAGTTTATGATGT
TCGTAAAATGATTGCTAAGTCTGAGCAAGAAATAGGCAAAGCAACCGCAA
AATATTTCTTTTACTCTAATATCATGAACTTCTTCAAAACAGAAATTACA
CTTGCAAATGGAGAGATTCGCAAACGCCCTCTAATCGAAACTAATGGGGA
AACTGGAGAAATTGTCTGGGATAAAGGGCGAGATTTTGCCACAGTGCGCA
AAGTATTGTCCATGCCCCAAGTCAATATTGTCAAGAAAACAGAAGTACGA
ACAGGCGGATTCTCCAAGGAGTCAATTTTACCAAAAAGAAATTCGGACAA
GCTTATTGCTCGTAAAAAGACTGGGATCCAAAAAAATATGGTGGTTTTG
ATAGTCCAACGGTAGCTTATTCAGTCCTAGTGGTTGCTAAGGTGGAAAAA
GGGAAATCGAAGAAGTTAAAATCCGTTAAAGAGTTACTAGGGATCACAAT
TATGGAAAGAAGTTCCTTTGAAAAAAATCCGATTGACTTTTTAGAAGCTA
AAGGATATAAGGAAGTTAAAAAAGACTTAATCATTAAACTACCTAAATAT
AGTCTTTTTGAGTTAGAAAACGGTCGTAAACGGATGCTGGCTAGTGCCGG
AGAATTACAAAAGGAAATGAGCTGGCTCTGCCAAGCAAATATGTGAATT
TTTTATATTTAGCTAGTCATTATGAAAAGTTGAAGGGTAGTCCAGAAGAT
AACGAACAAAAACAATTGTTTGTGGAGCAGCATAAGCATTATTTAGATGA
GATTATTGAGCAAATCAGTGAATTTCTAAGCGTGTTATTTTAGCAGATG
CCAATTTAGATAAAGTTCTTAGTGCATATAACAAACATAGAGACAAACCA
ATACGTGAACAAGCAGAAAATATTATTCATTTATTTACGTTGACGAATCT
TGGAGCTCCCGCTGCTTTTAAATATTTTGATACAACAATTGATCGTAAAC
GATATACGTCTACAAAAGAAGTTTTAGATGCCACTCTTATCCATCAATCC
ATCACTGGTCTTTATGAAACACGCATTGATTTGAGTCAGCTAGGAGGTGA
CTGA
```

(SEQ ID NO: 24)
MDKK<u>YSIGLDIGTNSVGWAVITDDYKVPSKKFKVLGNTDRHSIKKNLIGA
LLFGSGET</u>AEATRLKRTARRRYTRRKNRICYLQEIFSNEMAKVDDSFFHR
LEESFLVEEDKKHERHPIFGNIVDEVAYHEKYPTIYHLRKKLADSTDKAD
LRLIYLALAHMIKFRGHFLIEGDLNPDNSDVDKLFIQLVQIYNQLFEENP
INASRVDAKAILSARLSKSRRLENLIAQLPGEKRNGLFGNLIALSLGLTP
NFKSNFDLAEDAKLQLSKDTYDDDLDNLLAQIGDQYADLFLAAKNLSDAI
LLSDILRVNSEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGAYHDLLKI
IKDKDFLDNEENEDILEDIVLTLTLFEDRGMIEERLKTYAHLFDDKVMKQ
LKRRRYTGWGRLSRKLINGIRDKQSGKTILDFLKSDGFANRNFMQLIHDD
SLTFKEDIQKAQVSGQG<u>HSLHEQIANLAGSPAIKKGILQTVKIVDELVKV
MGHKPENIVIEMAR</u>ENQTTQKGQKNSRERMKRIEEGIKELGSQILKEHPV
ENTQLQNEKLYLYYLQNGRDMYVDQELDINRLSDYDVDHIVPQSFIKDDS
IDNKVLTRSDKNRGKSDNVPSEEVVKKMKNYWRQLLNAKLITQRKFDNLT
KAERG<u>GLSELDKAGFIKRQLVETRQITKHVAQILDSRMNTKYDENDKLIR
EVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEIT
LANGEIRKRPLIETNGETGEIVWDKGRDFATVRKVLSMPQVNIVKKTEVQ
T</u>GGFSKESILPKRNSDKLIARKKDWDPKKYGGFDSPTVAYSVLVVAKVEK
GKSKKLKSVKELLGITIMERSSFEKNPIDFLEAKGYKEVKKDLIIKLPKY
SLFELENGRKRMLASAGELQKGNELALPSKYVNFLYLASHYEKLKGSPED
NEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQS
ITGLYETRIDLSQLGGD (single underline: HNH domain; double underline: RuvC domain)

In some embodiments, wild type Cas9 corresponds to, or comprises SEQ ID NO: 25 (nucleotide) and/or SEQ ID NO: 26 (amino acid):

```
                                           (SEQ ID NO: 25)
ATGGATAAAAAGTATTCTATTGGTTTAGACATCGGCACTAATTCCGTTGG
ATGGGCTGTCATAACCGATGAATACAAAGTACCTTCAAAGAAATTTAAGG
TGTTGGGGAACACAGACCGTCATTCGATTAAAAAGAATCTTATCGGTGCC
CTCCTATTCGATAGTGGCGAAACGGCAGAGGCGACTCGCCTGAAACGAAC
CGCTCGGAGAAGGTATACACGTCGCAAGAACCGAATATGTTACTTACAAG
AAATTTTTAGCAATGAGATGGCCAAAGTTGACGATTCTTTCTTTCACCGT
TTGGAAGAGTCCTTCCTTGTCGAAGAGGACAAGAAACATGAACGGCACCC
CATCTTTGGAAACATAGTAGATGAGGTGGCATATCATGAAAAGTACCCAA
CGATTTATCACCTCAGAAAAAAGCTAGTTGACTCAACTGATAAAGCGGAC
CTGAGGTTAATCTACTTGGCTCTTGCCCATATGATAAAGTTCCGTGGGCA
CTTTCTCATTGAGGGTGATCTAAATCCGGACAACTCGGATGTCGACAAAC
TGTTCATCCAGTTAGTACAAACCTATAATCAGTTGTTTGAAGAGAACCCT
ATAAATGCAAGTGGCGTGGATGCGAAGGCTATTCTTAGCGCCCGCCTCTC
TAAATCCCGACGGCTAGAAAACCTGATCGCACAATTACCCGGAGAGAAGA
AAAATGGGTTGTTCGGTAACCTTATAGCGCTCTCACTAGGCCTGACACCA
AATTTTAAGTCGAACTTCGACTTAGCTGAAGATGCCAAATTGCAGCTTAG
TAAGGACACGTACGATGACGATCTCGACAATCTACTGGCACAAATTGGAG
ATCAGTATGCGGACTTATTTTTGGCTGCCAAAAACCTTAGCGATGCAATC
CTCCTATCTGACATACTGAGAGTTAATACTGAGATTACCAAGGCGCCGTT
ATCCGCTTCAATGATCAAAAGGTACGATGAACATCACCAAGACTTGACAC
TTCTCAAGGCCCTAGTCCGTCAGCAACTGCCTGAGAAATATAAGGAAATA
TTCTTTGATCAGTCGAAAAACGGGTACGCAGGTTATATTGACGGCGGAGC
GAGTCAAGAGGAATTCTACAAGTTTATCAAACCCATATTAGAGAAGATGG
ATGGGACGGAAGAGTTGCTTGTAAAACTCAATCGCGAAGATCTACTGCGA
```

-continued

```
AAGCAGCGGACTTTCGACAACGGTAGCATTCCACATCAAATCCACTTAGG
CGAATTGCATGCTATACTTAGAAGGCAGGAGGATTTTTATCCGTTCCTCA
AAGACAATCGTGAAAAGATTGAGAAAATCCTAACCTTTCGCATACCTTAC
TATGTGGGACCCCTGGCCCGAGGGAACTCTCGGTTCGCATGGATGACAAG
AAAGTCCGAAGAAACGATTACTCCATGGAATTTTGAGGAAGTTGTCGATA
AAGGTGCGTCAGCTCAATCGTTCATCGAGAGGATGACCAACTTTGACAAG
AATTTACCGAACGAAAAGTATTGCCTAAGCACAGTTTACTTTACGAGTA
TTTCACAGTGTACAATGAACTCACGAAAGTTAAGTATGTCACTGAGGGCA
TGCGTAAACCCGCCTTTCTAAGCGGAGAACAGAAGAAAGCAATAGTAGAT
CTGTTATTCAAGACCAACCGCAAAGTGACAGTTAAGCAATTGAAAGAGGA
CTACTTTAAGAAAATTGAATGCTTCGATTCTGTCGAGATCTCCGGGGTAG
AAGATCGATTTAATGCGTCACTTGGTACGTATCATGACCTCCTAAAGATA
ATTAAAGATAAGGACTTCCTGGATAACGAAGAGAATGAAGATATCTTAGA
AGATATAGTGTTGACTCTTACCCTCTTTGAAGATCGGGAAATGATTGAGG
AAAGACTAAAAACATACGCTCACCTGTTCGACGATAAGGTTATGAAACAG
TTAAAGAGGCGTCGCTATACGGGCTGGGGACGATTGTCGCGGAAACTTAT
CAACGGGATAAGAGACAAGCAAAGTGGTAAAACTATTCTCGATTTTCTAA
AGAGCGACGGCTTCGCCAATAGGAACTTTATGCAGCTGATCCATGATGAC
TCTTTAACCTTCAAAGAGGATATACAAAAGGCACAGGTTTCCGGACAAGG
GGACTCATTGCACGAACATATTGCGAATCTTGCTGGTTCGCCAGCCATCA
AAAAGGGCATACTCCAGACAGTCAAAGTAGTGGATGAGCTAGTTAAGGTC
ATGGGACGTCACAAACCGGAAAACATTGTAATCGAGATGGCACGCGAAAA
TCAAACGACTCAGAAGGGGCAAAAAACAGTCGAGAGCGGATGAAGAGAA
TAGAAGAGGGTATTAAAGAACTGGGCAGCCAGATCTTAAAGGAGCATCCT
GTGGAAAATACCCAATTGCAGAACGAGAAACTTTACCTCTATTACCTACA
AAATGGAAGGGACATGTATGTTGATCAGGAACTGGACATAAACCGTTTAT
CTGATTACGACGTCGATCACATTGTACCCCAATCCTTTTTGAAGGACGAT
TCAATCGACAATAAAGTGCTTACACGCTCGGATAAGAACCGAGGGAAAAG
TGACAATGTTCCAAGCGAGGAAGTCGTAAAGAAAATGAAGAACTATTGGC
GGCAGCTCCTAAATGCGAAACTGATAACGCAAAGAAAGTTCGATAACTTA
ACTAAAGCTGAGAGGGGTGGCTTGTCTGAACTTGACAAGGCCGGATTTAT
TAAACGTCAGCTCGTGGAAACCCGCCAAATCACAAAGCATGTTGCACAGA
TACTAGATTCCCGAATGAATACGAAATACGACGAGAACGATAAGCTGATT
CGGGAAGTCAAAGTAATCACTTTAAAGTCAAAATTGGTGTCGGACTTCAG
AAAGGATTTTCAATTCTATAAAGTTAGGGAGATAAATAACTACCACCATG
CGCACGACGCTTATCTTAATGCCGTCGTAGGGACCGCACTCATTAAGAAA
TACCCGAAGCTAGAAAGTGAGTTTGTGTATGGTGATTACAAAGTTTATGA
CGTCCGTAAGATGATCGCGAAAAGCGAACAGGAGATAGGCAAGGCTACAG
CCAAATACTTCTTTTATTCTAACATTATGAATTTCTTTAAGACGAAATC
ACTCTGGCAAACGGAGAGATACGCAAACGACCTTTAATTGAAACCAATGG
GGAGACAGGTGAAATCGTATGGGATAAGGGCCGGGACTTCGCGACGGTGA
GAAAAGTTTTGTCCATGCCCCAAGTCAACATAGTAAAGAAAACTGAGGTG
CAGACCGGAGGGTTTTCAAAGGAATCGATTCTTCCAAAAAGGAATAGTGA
TAAGCTCATCGCTCGTAAAAAGGACTGGGACCCGAAAAAGTACGGTGGCT
TCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAAC
GATTATGGAGCGCTCGTCTTTTGAAAAGAACCCCATCGACTTCCTTGAGG
CGAAAGGTTACAAGGAAGTAAAAAAGGATCTCATAATTAAACTACCAAAG
TATAGTCTGTTTGAGTTAGAAAATGGCCGAAAACGGATGTTGGCTAGCGC
CGGAGAGCTTCAAAAGGGGAACGAACTCGCACTACCGTCTAAATACGTGA
ATTTCCTGTATTTAGCGTCCCATTACGAGAAGTTGAAAGGTTCACCTGAA
GATAACGAACAGAAGCAACTTTTTGTTGAGCAGCACAAACATTATCTCGA
CGAAATCATAGAGCAAATTTCGGAATTCAGTAAGAGAGTCATCCTAGCTG
ATGCCAATCTGGACAAAGTATTAAGCGCATACAACAAGCACAGGGATAAA
CCCATACGTGAGCAGGCGGAAAATATTATCCATTTGTTTACTCTTACCAA
CCTCGGCGCTCCAGCCGCATTCAAGTATTTTGACACAACGATAGATCGCA
AACGATACACTTCTACCAAGGAGGTGCTAGACGCGACACTGATTCACCAA
TCCATCACGGGATTATATGAAACTCGGATAGATTTGTCACAGCTTGGGGG
TGACGGATCCCCCAAGAAGAAGAGGAAAGTCTCGAGCGACTACAAAGACC
ATGACGGTGATTATAAAGATCATGACATCGATTACAAGGATGACGATGAC
AAGGCTGCAGGA
```

```
                                             (SEQ ID NO: 26)
MDKKYSIGLAIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKEDNL
```

-continued

TKAERG<u>GLSELDKAGFIKRQLVETRQITKHVAQILDSRMNTKYDENDKLI</u>

<u>REVKVITLKSKLVSDFRKDFQFYKVREINNYHHAHDAYLNAVVGTALIKK</u>

<u>YPKLESEFVYGDYKVYDVRKMIAKSEQEIGKATAKYFFYSNIMNFFKTEI</u>

<u>TLANGEIRKRPLIETNGETGEIVWDKGRDFATVRKVLSMPQVNIVKKTEV</u>

<u>QT</u>GGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
(single underline: HNH domain; double underline: RuvC domain)

In some embodiments, wild type Cas9 corresponds to Cas9 from *Streptococcus pyogenes* (NCBI Reference Sequence: NC_002737.2, SEQ ID NO: 27 (nucleotide); and Uniport Reference Sequence: Q99ZW2, SEQ ID NO: 28 (amino acid).

(SEQ ID NO: 27)
ATGGATAAGAAATACTCAATAGGCTTAGATATCGGCACAAATAGCGTCGG

ATGGGCGGTGATCACTGATGAATATAAGGTTCCGTCTAAAAAGTTCAAGG

TTCTGGGAAATACAGACCGCCACAGTATCAAAAAAATCTTATAGGGGCT

CTTTTATTTGACAGTGGAGAGACAGCGGAAGCGACTCGTCTCAAACGGAC

AGCTCGTAGAAGGTATACACGTCGGAAGAATCGTATTTGTTATCTACAGG

AGATTTTTTCAAATGAGATGGCGAAAGTAGATGATAGTTTCTTTCATCGA

CTTGAAGAGTCTTTTTTGGTGGAAGAAGACAAGAAGCATGAACGTCATCC

TATTTTTGGAAATATAGTAGATGAAGTTGCTTATCATGAGAAATATCCAA

CTATCTATCATCTGCGAAAAAATTGGTAGATTCTACTGATAAAGCGGAT

TTGCGCTTAATCTATTTGGCCTTAGCGCATATGATTAAGTTTCGTGGTCA

TTTTTTGATTGAGGGAGATTTAAATCCTGATAATAGTGATGTGGACAAAC

TATTTATCCAGTTGGTACAAACCTACAATCAATTATTTGAAGAAAACCCT

ATTAACGCAAGTGGAGTAGATGCTAAAGCGATTCTTTCTGCACGATTGAG

TAAATCAAGACGATTAGAAAATCTCATTGCTCAGCTCCCCGGTGAGAAGA

AAAATGGCTTATTTGGGAATCTCATTGCTTTGTCATTGGGTTTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTGGCAGCTAAGAATTTATCAGATGCTATT

TTACTTTCAGATATCCTAAGAGTAAATACTGAAATAACTAAGGCTCCCCT

ATCAGCTTCAATGATTAAACGCTACGATGAACATCATCAAGACTTGACTC

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAGTACTACCAAAACATAGTTTGCTTTATGAGTA

TTTTACGGTTTATAACGAATTGACAAAGGTCAAATATGTTACTGAAGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG

AAGATAGATTTAATGCTTCATTAGGTACCTACCATGATTTGCTAAAAATT

ATTAAAGATAAAGATTTTTTGGATAATGAAGAAAATGAAGATATCTTAGA

GGATATTGTTTTAACATTGACCTTATTTGAAGATAGGGAGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTTGA

AATCAGATGGTTTTGCCAATCGCAATTTTATGCAGCTGATCCATGATGAT

AGTTTGACATTTAAAGAAGACATTCAAAAAGCACAAGTGTCTGGACAAGG

CGATAGTTTACATGAACATATTGCAAATTTAGCTGGTAGCCCTGCTATTA

AAAAAGGTATTTTACGACTGTAAAAGTTGTTGATGAATTGGTCAAAGTA

ATGGGGCGGCATAAGCCAGAAAATATCGTTATTGAAATGGCACGTGAAAA

TCAGACAACTCAAAAGGGCCAGAAAAATTCGCGAGAGCGTATGAAACGAA

TCGAAGAAGGTATCAAAGAATTAGGAAGTCAGATTCTTAAAGAGCATCCT

GTTGAAAATACTCAATTGCAAAATGAAAAGCTCTATCTCTATTATCTCCA

AAATGGAAGAGACATGTATGTGGACCAAGAATTAGATATTAATCGTTTAA

GTGATTATGATGTCGATCACATTGTTCCACAAAGTTTCCTTAAAGACGAT

TCAATAGACAATAAGGTCTTAACGCGTTCTGATAAAAATCGTGGTAAATC

GGATAACGTTCCAAGTGAAGAAGTAGTCAAAAAGATGAAAAACTATTGGA

GACAACTTCTAAACGCCAAGTTAATCACTCAACGTAAGTTTGATAATTTA

ACGAAAGCTGAACGTGGAGGTTTGAGTGAACTTGATAAAGCTGGTTTTAT

CAAACGCCAATTGGTTGAAACTCGCCAAATCACTAAGCATGTGGCACAAA

TTTTGGATAGTCGCATGAATACTAAATACGATGAAAATGATAAACTTATT

CGAGAGGTTAAAGTGATTACCTTAAAATCTAAATTAGTTTCTGACTTCCG

AAAAGATTTCCAATTCTATAAAGTACGTGAGATTAACAATTACCATCATG

CCCATGATGCGTATCTAAATGCCGTCGTTGGAACTGCTTTGATTAAGAAA

TATCCAAAACTTGAATCGGAGTTTGTCTATGGTGATTATAAAGTTTATGA

TGTTCGTAAAATGATTGCTAAGTCTGAGCAAGAAATAGGCAAAGCAACCG

CAAAATATTTCTTTTACTCTAATATCATGAACTTCTTCAAAACAGAAATT

ACACTTGCAAATGGAGAGATTCGCAAACGCCCTCTAATCGAAACTAATGG

GGAAACTGGAGAAATTGTCTGGGATAAAGGGCGAGATTTTGCCACAGTGC

```
GCAAAGTATTGTCCATGCCCCAAGTCAATATTGTCAAGAAAACAGAAGTA

CAGACAGGCGGATTCTCCAAGGAGTCAATTTTACCAAAAAGAAATTCGGA

CAAGCTTATTGCTCGTAAAAAGACTGGGATCCAAAAAAATATGGTGGTT

TTGATAGTCCAACGGTAGCTTATTCAGTCCTAGTGGTTGCTAAGGTGGAA

AAAGGGAAATCGAAGAAGTTAAAATCCGTTAAAGAGTTACTAGGGATCAC

AATTATGGAAAGAAGTTCCTTTGAAAAAAATCCGATTGACTTTTTAGAAG

CTAAAGGATATAAGGAAGTTAAAAAAGACTTAATCATTAAACTACCTAAA

TATAGTCTTTTTGAGTTAGAAAACGGTCGTAAACGGATGCTGGCTAGTGC

CGGAGAATTACAAAAAGGAAATGAGCTGGCTCTGCCAAGCAAATATGTGA

ATTTTTTATATTTAGCTAGTCATTATGAAAAGTTGAAGGGTAGTCCAGAA

GATAACGAACAAAAACAATTGTTTGTGGAGCAGCATAAGCATTATTTAGA

TGAGATTATTGAGCAAATCAGTGAATTTTCTAAGCGTGTTATTTTAGCAG

ATGCCAATTTAGATAAAGTTCTTAGTGCATATAACAAACATAGAGACAAA

CCAATACGTGAACAAGCAGAAAATATTATTCATTTATTTACGTTGACGAA

TCTTGGAGCTCCCGCTGCTTTTAAATATTTTGATACAACAATTGATCGTA

AACGATATACGTCTACAAAAGAAGTTTTAGATGCCACTCTTATCCATCAA

TCCATCACTGGTCTTTATGAAACACGCATTGATTTGAGTCAGCTAGGAGG

TGACTGA
```

(SEQ ID NO: 28)
MDKK<u>YSIGLDIGTNSVGWAVITDEYKVPSKKFKVLGNTDRHSIKKNLIGA</u>

<u>LLEDSGET</u>AEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQG<u>DSLHEHIANLAGSPAIKKGILQTVKVVDELVKV</u>

<u>MGRHKPENIVIEMAR</u>ENQTTQKG<u>QKNSRERMKRIEEGIKELGSQILKEHP</u>

<u>VENTQLQNEKLYLYYLQNGRDMYVDQELDINRLSDYDVDHIVPQSFLKDD</u>

<u>SIDNKVLTRSDKNRGKSDNVPSEEVVKKMKNYWRQLLNAKLITQRKFDNL</u>

<u>TKAERGGL</u>SELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD (single underline: HNH domain; double underline: RuvC domain)

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1), *Listeria innocua* (NCBI Ref: NP_472073.1), *Campylobacter jejuni* (NCBI Ref: YP_002344900.1) or *Neisseria meningitidis* (NCBI Ref: YP_002342100.1) or to a Cas9 from any other suitable organism.

In some embodiments, dCas9 corresponds to, or comprises in part or in whole, a Cas9 amino acid sequence having one or more mutations that inactivate the Cas9 nuclease activity. For example, in some embodiments, a dCas9 domain comprises D10A and/or H840A mutation.

dCas9 (D10A and H840A):

(SEQ ID NO: 29)
MDKK<u>YSIGLAIGTNSVGWAVITDEYKVPSKKFKVLGNTDRHSIKKNLIGALLFDSG</u>

<u>ET</u>AEATRLKRTARRRYTRRKNRICYLQEIFSNEMAKVDDSFFHRLEESFLVEEDKKHER

HPIFGNIVDEVA YHEKYPTIYHLRKKLVDSTDKADLRLIYLALAHMIKFRGHFLIEGDLN

PDNSDVDKLFIQLVQTYNQLFEENPINASGVDAKAILSARLSKSRRLENLIAQLPGEKKN

```
GLFGNLIALSLGLTPNFKSNFDLAEDAKLQLSKDTYDDDLDNLLAQIGDQYADLFLAAK

NLSDAILLSDILRVNTEITKAPLSASMIKRYDEHHQDLTLLKALVRQQLPEKYKEIFFDQS

KNGYAGYIDGGASQEEFYKFIKPILEKMDGTEELLVKLNREDLLRKQRTFDNGSIPHQIH

LGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEG

MRKPAFLSGEQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHLFDDKVMKQLK

RRRYTGWGRLSRKLINGIRDKQSGKTILDFLKSDGFANRNFMQLIHDDSLTFKEDIQKA

QVSGQG DSLHEHIANLAGSPAIKKGILQTVKVVDELVKVMGRHKPENIVIEMA RENQTT

QK GQKNSRERMKRIEEGIKELGSQILKEHPVENTQLQNEKLYLYYLONGRDMYVD

QELDINRLSDYDVDAIVPQSFLKDDSIDNKVLTRSDKNRGKSDNVPSEEVVKKMKN

YWRQLLNAKLITORKFDNLTK AERG GLSELDKAGFIKRQLVETRQITKHVAQILDSR

MNTKYDENDKLIREVKVITLKSKLVSDFRKDFQFYKVREINNYHHAHDAYLNAVVGT

ALIKKYPKLESEFVYGDYKVYDVRKMIASEQEIGKATAKYFFYSNIMNFFKTEITLAN

GEIRKRPLIETNGETGEIVWDKGRDFATVRKVLSMPQVNIVKKTEVQT GGFSKESILPKR

NSDKLIARKKDWDPKKYGGFDSPTVAYSVLVVAKVEKGKSKKLKSVKELLGITIMERS

SFEKNPIDFLEAKGYKEVKKDLIIKLPKYSLFELENGRKRMLASAGELQKGNELALPSKY

VNFLYLASHYEKLKGSPEDNEQKQLFVEQHKHYLDEIIEQISEFSKR VILADANLDKVLS

AYNKHRDKPIREQAENIIHLFTLTNLGAPAAFKYFDTTIDRKRYTSTKEVLDATLIHQSIT

GLYETRIDLSQLGGD
(single underline: HNH domain; double underline: RuvC domain)
```

In some embodiments, the Cas9 domain comprises a D10A mutation, while the residue at position 840 remains a histidine in the amino acid sequence provided in SEQ ID NO: 29, or at a corresponding position in another Cas9 domain. Without wishing to be bound by any particular theory, the presence of the catalytic residue H840 restores the activity of the Cas9 to cleave the non-edited (e.g., non-deaminated) strand containing a G opposite the targeted C. Restoration of H840 (e.g., from A840) does not result in the cleavage of the target strand containing the C. Such Cas9 variants are able to generate a single-strand DNA break (nick) at a specific location based on the gRNA-defined target sequence, leading to repair of the non-edited strand, ultimately resulting in a G to A change on the non-edited strand.

In other embodiments, dCas9 variants having mutations other than D10A and H840A are provided, which, e.g., result in nuclease inactivated Cas9 (dCas9). Such mutations, by way of example, include other amino acid substitutions at D10 and H820, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO: 29) are provided which are at least about 70% identical, at least about 80% identical, at least about 90% identical, at least about 95% identical, at least about 98% identical, at least about 99% identical, at least about 99.5% identical, or at least about 99.9% identical to SEQ ID NO: 29. In some embodiments, variants of dCas9 (e.g., variants of SEQ ID NO: 29) are provided having amino acid sequences which are shorter, or longer than SEQ ID NO: 29, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

In some embodiments, Cas9 fusion proteins as provided herein comprise the full-length amino acid sequence of a Cas9 protein, e.g., one of the Cas9 sequences provided herein. In other embodiments, however, fusion proteins as provided herein do not comprise a full-length Cas9 sequence, but only a fragment thereof. For example, in some embodiments, a Cas9 fusion protein provided herein comprises a Cas9 fragment, wherein the fragment binds crRNA and tracrRNA or sgRNA, but does not comprise a functional nuclease domain, e.g., in that it comprises only a truncated version of a nuclease domain or no nuclease domain at all. Exemplary amino acid sequences of suitable Cas9 domains and Cas9 fragments are provided herein, and additional suitable sequences of Cas9 domains and fragments will be apparent to those of skill in the art.

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref:

NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria meningitidis* (NCBI Ref: YP_002342100.1).

The term "nucleobase editors (NBEs)" or "base editors (BEs)," as used herein, refers to the Cas9 fusion proteins described herein. In some embodiments, the fusion protein comprises a nuclease-inactive Cas9 (dCas9) fused to a deaminase. In some embodiments, the fusion protein comprises a Cas9 nickase fused to a deaminase. In some embodiments, the fusion protein comprises a nuclease-inactive Cas9 fused to a deaminase and further fused to a UGI domain. In some embodiments, the fusion protein comprises a Cas9 nickase fused to a deaminase and further fused to a UGI domain. In some embodiments, the dCas9 of the fusion protein comprises a D10A and a H840A mutation, which inactivates nuclease activity of the Cas9 protein, or which renders Cas9 capable of cleaving only one strand of a nucleic acid duplex. The terms "nucleobase editors (NBEs)" and "base editors (BEs)" may be used interchangeably.

The term "uracil glycosylase inhibitor" or "UGI," as used herein, refers to a protein that is capable of inhibiting a uracil-DNA glycosylase base-excision repair enzyme.

The term "Cas9 nickase," as used herein, refers to a Cas9 protein that is capable of cleaving only one strand of a duplexed nucleic acid molecule (e.g., a duplexed DNA molecule). In some embodiments, a Cas9 nickase comprises a D10A mutation and has a histidine at position H840. Such a Cas9 nickase has an active HNH nuclease domain and is able to cleave the non-targeted strand of DNA, i.e., the strand bound by the gRNA. Further, such a Cas9 nickase has an inactive RuvC nuclease domain and is not able to cleave the targeted strand of the DNA, i.e., the strand where base editing is desired.

Exemplary Cas9 nickase (Cloning vector pPlatTET-gRNA2; Accession No. BAV54124).

```
                                         (SEQ ID NO: 21)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITORKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

The term "linker," as used herein, refers to a chemical group or a molecule linking two molecules or moieties, e.g., two domains of a fusion protein, such as, for example, a nuclease-inactive Cas9 domain and a nucleic acid editing domain (e.g., a deaminase domain). In some embodiments, a linker joins a gRNA binding domain of an RNA-programmable nuclease, including a Cas9 nuclease domain, and the catalytic domain of a nucleic-acid editing protein. In some embodiments, a linker joins a dCas9 and a nucleic-acid editing protein. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The term "nucleic acid editing domain," as used herein refers to a protein or enzyme capable of making one or more modifications (e.g., deamination of a cytidine residue) to a nucleic acid (e.g., DNA or RNA). Exemplary nucleic acid editing domains include, but are not limited to a deaminase, a nuclease, a nickase, a recombinase, a methyltransferase, a methylase, an acetylase, an acetyltransferase, a transcriptional activator, or a transcriptional repressor domain. In some embodiments the nucleic acid editing domain is a deaminase (e.g., a cytidine deaminase, such as an APOBEC or an AID deaminase).

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease:RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is identical or homologous to a tracrRNA as provided in Jinek et al., Science 337:816-821(2012), the entire contents of which is incorporated herein by reference. Other examples of gRNAs (e.g., those including domain 2) can be found in U.S. Provisional Patent Application Ser. No. 61/874,682, filed Sep. 6, 2013, entitled "Switchable Cas9 Nucleases And Uses Thereof," and U.S. Provisional Patent Application Ser. No. 61/874,746, filed Sep. 6, 2013, entitled "Delivery System For Functional Nucleases," the entire contents of each are hereby incorporated by reference in their entirety. In some embodiments, a gRNA comprises two or more of domains (1) and (2), and may be referred to as an "extended gRNA." For example, an extended gRNA will, e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference.

Because RNA-programmable nucleases (e.g., Cas9) use RNA:DNA hybridization to target DNA cleavage sites, these proteins are able to be targeted, in principle, to any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); Mali, P. et al. RNA-guided human genome engineering via Cas9. Science 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. *eLife* 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

The term "host cell," as used herein, refers to a cell that can host, replicate, and transfer a phage vector useful for a continuous evolution process as provided herein. In embodiments where the vector is a viral vector, a suitable host cell is a cell that can be infected by the viral vector, can replicate it, and can package it into viral particles that can infect fresh host cells. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the disclosure is not limited in this respect.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The term "target site" refers to a sequence within a nucleic acid molecule that is deaminated by a deaminase or a fusion protein comprising a deaminase (e.g., a dCas9-deaminase fusion protein provided herein).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. In some embodiments, an effective amount of a fusion protein provided herein, e.g., of a fusion protein comprising a nuclease-inactive Cas9 domain and a nucleic acid editing domain (e.g., a deaminase domain) may refer to the amount of the fusion protein that is sufficient to induce editing of a target site specifically bound and edited by the fusion protein. As will be appreciated by the skilled artisan, the effective amount of an agent, e.g., a fusion protein, a nuclease, a deaminase, a recombinase, a hybrid protein, a protein dimer, a complex of a protein (or protein dimer) and a polynucleotide, or a polynucleotide, may vary depending on various factors as, for example, on the desired biological response, e.g., on the specific allele, genome, or target site to be edited, on the cell or tissue being targeted, and on the agent being used.

DETAILED DESCRIPTION OF CERTAIN EMBODIMENTS

Some aspects of this disclosure provide cytidine deaminase variants (e.g., APOBEC1 protein variants) and methods, compositions, and systems for producing the same. In some embodiments, the disclosure relates to the use of soluble expression phage-assisted continuous evolution (SE-PACE) to produce cytidine deaminase protein variants. In some embodiments, cytidine deaminase protein variants described by the disclosure exhibit improved soluble expression (e.g., improved soluble expression in *E. coli* cells) relative to the wild-type cytidine deaminase protein from which they are derived. Some aspects of this disclosure provide fusion proteins, such as base editors (BEs) comprising a cytidine deaminase protein variant fused to a nuclease-inactive Cas9 protein, and further fused to other domains or sequences (e.g., a UGI domain).

Cytidine Deaminase Protein Variants

Some aspects of the disclosure relate to cytidine deaminase protein variants. The disclosure is based, in part, on cytidine deaminase protein variants that are characterized by increased soluble expression (e.g., increased soluble expression in *E. coli* cells) relative to wild-type cytidine deaminase proteins (e.g., the cytidine deaminase protein from which the variant was evolved). In some embodiments, cytidine deaminase protein variants described by the disclosure are characterized by maintained (e.g., the same) or improved (e.g., increased) deaminase activity relative to wild-type cytidine deaminase proteins (e.g., the cytidine deaminase protein from which the variant was evolved).

Cytidine deaminase protein variants described by the disclosure are typically derived from a wild-type cytidine deaminase protein and have at least one variation in the amino acid sequence of the variant protein as compared to the amino acid sequence of the cognate wild-type cytidine deaminase protein. In some embodiments, a cytidine deaminase protein variant has at least one variation in its encoding nucleic acid sequence that results in a change in the amino acid sequence present within a cognate wild type cytidine deaminase protein. The variation in amino acid sequence generally results from a mutation, insertion, or deletion in a DNA coding sequence. Mutation of a DNA sequence can result in a nonsense mutation (e.g., a transcription termination codon (TAA, TAG, or TGA) that produces a truncated protein), a missense mutation (e.g., an insertion or deletion mutation that shifts the reading frame of the coding sequence), or a silent mutation (e.g., a change in the coding sequence that results in a codon that codes for the same amino acid normally present in the cognate protein, also referred to sometimes as a synonymous mutation). In some embodiments, mutation of a DNA sequence results in a non-synonymous (i.e., conservative, semi-conservative, or radical) amino acid substitution.

The cytidine deaminase protein can be any cytidine deaminase protein known in the art. In some embodiments, a cytidine deaminase protein variant is an apolipoprotein B mRNA-editing complex (APOBEC) family deaminase variant. In some embodiments, the deaminase is an APOBEC1 deaminase protein variant. In some embodiments, the deaminase is an APOBEC2 deaminase protein variant. In some embodiments, the deaminase is an APOBEC3 deaminase protein variant. In some embodiments, the deaminase is an APOBEC3A deaminase protein variant. In some embodiments, the deaminase is an APOBEC3B deaminase protein variant. In some embodiments, the deaminase is an APOBEC3C deaminase protein variant. In some embodiments, the deaminase is an APOBEC3D deaminase protein variant. In some embodiments, the deaminase is an APOBEC3E deaminase. In some embodiments, the deaminase is an APOBEC3F deaminase protein variant. In some embodiments, the deaminase is an APOBEC3G deaminase protein variant. In some embodiments, the deaminase is an APOBEC3H deaminase protein variant. In some embodiments, the deaminase is an APOBEC4 deaminase protein variant.

In some embodiments, a cytidine deaminase protein variant is a vertebrate cytidine deaminase protein variant. In some embodiments, the deaminase is a human, chimpanzee, gorilla, monkey, cow, dog, rat, or mouse deaminase. In some embodiments, the deaminase is a human deaminase. In some embodiments, the deaminase is a rat deaminase, e.g., rAPOBEC1. In some embodiments, a deaminase variant is an invertebrate deaminase variant, for example, a variant of a *Petromyzon marinus* cytosine deaminase 1 (pmCDA1).

In some embodiments, a cytidine deaminase protein variant and a wild-type cytidine deaminase protein (e.g., rAPOBEC1) are from about 50% to about 99.9% identical, about 55% to about 95% identical, about 60% to about 90% identical, about 65% to about 85% identical, or about 70% to about 80% identical at the amino acid sequence level. In some embodiments, a cytidine deaminase protein variant comprises an amino acid sequence that is at least 50%, at least 60%, at least 70%, at least 80%, at least 90%, at least 95%, at least 99%, or at least 99.9% identical to the amino acid sequence of a wild-type cytidine deaminase protein (e.g., an APOBEC1 deaminase, such as rAPOBEC1). In some embodiments, amino acid sequence identity is based on an alignment against a reference sequence (e.g., a wild-type cytidine deaminase protein, for example, an APOBEC1 deaminase, such as rAPOBEC1) by NCBI Constraint-based Multiple Alignment Tool (COBALT), using the following parameters; Alignment Parameters: Gap penalties-11,-1 and End-Gap penalties-5,-1, CDD Parameters: Use RPS BLAST on; Blast E-value 0.003; Find Conserved columns and Recompute on, and Query Clustering Parameters: Use query clusters on; Word Size 4; Max cluster distance 0.8; Alphabet Regular.

In some embodiments, a cytidine deaminase protein variant is about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9% identical to a wild-type cytidine deaminase protein (e.g., an APOBEC1 deaminase, such as rAPOBEC1).

The amount or level of variation between a wild-type cytidine deaminase protein and a cytidine deaminase protein variant can also be expressed as the number of mutations present in the amino acid sequence encoding the cytidine deaminase protein variant relative to the amino acid sequence encoding the wild-type cytidine deaminase protein. In some embodiments, an amino acid sequence encoding a cytidine deaminase protein variant comprises between about 1 mutation and about 100 mutations, about 10 mutations and about 90 mutations, about 20 mutations and about 80 mutations, about 30 mutations and about 70 mutations, or about 40 and about 60 mutations relative to an amino acid sequence encoding a wild-type cytidine deaminase protein (e.g., an APOBEC1 protein, such as rAPOBEC1). In some embodiments, an amino acid sequence encoding a cytidine deaminase protein variant comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mutations relative to an amino acid sequence encoding a wild-type cytidine deaminase protein (e.g., an APOBEC1 protein, such as rAPOBEC1). In some embodiments, an amino acid sequence of a cytidine deaminase protein variant comprises more than 100 mutations relative to an amino acid sequence of a wild-type cytidine deaminase protein.

Particular combinations of mutations present in an amino acid sequence encoding a cytidine deaminase protein variant can be referred to as the "genotype" of the cytidine deaminase protein variant. For example, a cytidine deaminase protein variant genotype may comprise the mutations F113C, A123E, and F205S, relative to a wild-type cytidine deaminase protein rAPOBEC1 (e.g., SEQ ID NO: 15). In some embodiments, a cytidine deaminase protein variant genotype may comprise the mutations G45D, Y75H, F113C, A123E, H166N, and F205S, relative to a wild-type cytidine deaminase protein rAPOBEC1 (e.g., SEQ ID NO: 15). In some embodiments, a cytidine deaminase protein variant genotype may comprise the mutations F113C, A123E, A165T, and F205S, relative to a wild-type cytidine deaminase protein rAPOBEC1 (e.g., SEQ ID NO: 15). Aspects of the disclosure relate to the discovery that cytidine deaminase protein variants having a mutation at position E63 (relative to wild-type rAPOBEC1; SEQ ID NO: 15) are characterized by a loss of deaminase function. Accordingly, in some embodiments, a cytidine deaminase protein variant does not comprise (e.g., lacks) a mutation at the position corresponding to position E63 of wild-type rAPOBEC1 (SEQ ID NO: 15). In some embodiments, a cytidine deaminase protein variant does not comprise an E63A mutation (at a position corresponding to position E63 of rAPOBEC1, SEQ ID NO: 15).

```
rAPOBEC1
                                        (SEQ ID NO: 15)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLK (SEQ ID NO: 30)
MTSEKGPSTGDPTLRRRIEPWEFDVFYDPRELRKEACLLYEIKWGMSRKI

WRSSGKNTTNHVEVNFIKKFTSERDFHPSMSCSITWFLSWSPCWECSQAI

REFLSRHPGVTLVIYVARLFWHMDQQNRQGLRDLVNSGVTIQIMRASEYY

HCWRNFVNYPPGDEAHWPQYPPLWMMLYALELHCIILSLPPCLKISRRWQ

NHLTFFRLHLQNCHYQTIPPHILLATGLIHPSVAWR
```

Base Editing Proteins

Some aspects of the disclosure relate to fusion proteins (e.g., base editing proteins) comprising (i) a RNA-programmable nuclease (e.g., a Cas9 domain); and (ii) a nucleic acid editing domain (e.g., a cytidine deaminase protein variant as described by the disclosure). In some embodiments, a Cas9 domain is a nuclease-inactive Cas9 domain (dCas9), and comprises an amino acid sequence that is at least 80%, at least 85%, at least 90%, at least 92%, at least 95%, at least 96%, at least 97%, at least 98%, at least 99%, or at least 99.5% identical to the amino acid sequence of a Cas9 protein (e.g., SEQ ID NO: 20). Mutations that render the nuclease activity of Cas9 inactive are known in the art. For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of S. pyogenes Cas9 (Jinek et al., Science. 337:816-821(2012); Qi et al., Cell. 28; 152(5):1173-83 (2013)). In some embodiments, the dCas9 comprises a D10A mutation. In some embodiments, the dCas9 comprises a H840A mutation. In some embodiments, a dCas9 comprises both D10A and H840A mutations. It is to be understood that other mutations that inactivate the nuclease activity of Cas9 may also be included in the dCas9 of this disclosure. The above-noted mutations and additional dCas9 mutations are described, for example, in International PCT Application No. PCT/US2016/058344, published on Apr. 27, 2017 as WO 2017/070632; International PCT Application No. PCT/US2016/058345, published on Apr. 27, 2017 as WO 2017/070633; and International PCT Application No. PCT/US2017/045381, published on Feb. 8, 2018 as WO 2018/027078, the entire contents of each application which are incorporated herein by reference.

The Cas9 or dCas9 domains disclosed herein, may be a full-length Cas9, or a fragment thereof. In some embodiments, proteins comprising Cas9, or fragments thereof, are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9, e.g., a Cas9 comprising the amino acid sequence of SEQ ID NO: 24.

Any of the Cas9 fusion proteins of this disclosure may further comprise a nucleic acid editing domain (e.g., an enzyme that is capable of modifying nucleic acid, such as a deaminase). In some embodiments, the nucleic acid editing domain is a DNA-editing domain.

In some embodiments, the Cas9 domain and the nucleic acid editing-editing domain are fused via a linker. In some embodiments, the linker comprises a (GGGS)$_n$ (SEQ ID NO: 31), a (GGGGS)$_n$ (SEQ ID NO: 32), a (G)$_n$, an (EAAAK)$_n$ (SEQ ID NO: 33), a (GGS)$_n$, an SGSETPGTS-ESATPES (SEQ ID NO: 34) motif (see, e.g., Guilinger J P, Thompson D B, Liu D R. Fusion of catalytically inactive Cas9 to FokI nuclease improves the specificity of genome modification. *Nat. Biotechnol.* 2014; 32(6): 577-82; the entire contents are incorporated herein by reference), or an (XP)$_n$ motif, or a combination of any of these, wherein n is independently an integer between 1 and 30. In some embodiments, n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or, if more than one linker or more than one linker motif is present, any combination thereof. In some embodiments, the linker comprises a (GGS)$_n$ motif, wherein n is 1, 2, 3, 4, 5, 6, 7, 8, 9, 10, 11, 12, 13, 14 or 15. In some embodiments, the linker comprises a (GGS)$_n$ motif, wherein n is 1, 3, or 7. In some embodiments, the linker comprises the amino acid sequence SGSETPGTSESATPES (SEQ ID NO: 34). Additional suitable linker motifs and linker configurations will be apparent to those of skill in the art. In some embodiments, suitable linker motifs and configurations include those described in Chen et al., Fusion protein linkers: property, design and functionality. *Adv Drug Deliv Rev.* 2013; 65(10):1357-69, the entire contents of which are incorporated herein by reference. Additional suitable linker sequences will be apparent to those of skill in the art based on the instant disclosure. In some embodiments, the general architecture of exemplary Cas9 fusion proteins provided herein comprises the structure:

[NH$_2$]-[nucleic acid editing domain]-[Cas9]-[COOH] or
[NH$_2$]-[nucleic acid editing domain]-[linker]-[Cas9]-[COOH], wherein NH$_2$ is the N-terminus of the fusion protein, and COOH is the C-terminus of the fusion protein.

The fusion proteins of the present disclosure may comprise one or more additional features. For example, in some embodiments, the fusion protein comprises a nuclear localization sequence (NLS). In some embodiments, the NLS of the fusion protein is localized between the nucleic acid editing domain and the Cas9 domain. In some embodiments, the NLS of the fusion protein is localized C-terminal to the Cas9 domain.

Other exemplary features that may be present are localization sequences, such as cytoplasmic localization sequences, export sequences, such as nuclear export sequences, or other localization sequences, as well as sequence tags that are useful for solubilization, purification, or detection of the fusion proteins. Suitable protein tags provided herein include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art. In some embodiments, the fusion protein comprises one or more His tags.

In some embodiments, the nucleic acid editing domain is a cytidine deaminase protein variant. For example, in some embodiments, the general architecture of exemplary Cas9 fusion proteins with a deaminase domain comprises the structure:

[NH$_2$]-[NLS]-[deaminase]-[Cas9]-[COOH],
[NH$_2$]-[Cas9]-[deaminase]-[COOH],
[NH$_2$]-[deaminase]-[Cas9]-[COOH], or
[NH$_2$]-[deaminase]-[Cas9]-[NLS]-[COOH]

wherein NLS is a nuclear localization sequence, NH$_2$ is the N-terminus of the fusion protein, and COOH is the C-terminus of the fusion protein. Nuclear localization sequences are known in the art and would be apparent to the skilled artisan. For example, NLS sequences are described in Plank et al., PCT/EP2000/011690, the contents of which are incorporated herein by reference for their disclosure of exemplary nuclear localization sequences. In some embodiments, a NLS comprises the amino acid sequence PKKKRKV (SEQ ID NO: 35) or MDSLLMNRRKFLYQFKNVRWAKGRRE-TYLC (SEQ ID NO: 36). In some embodiments, a linker is inserted between the Cas9 and the deaminase. In some embodiments, the NLS is located C-terminal of the Cas9 domain. In some embodiments, the NLS is located N-terminal of the Cas9 domain. In some embodiments, the NLS is located between the deaminase and the Cas9 domain. In some embodiments, the NLS is located N-terminal of the deaminase domain. In some embodiments, the NLS is located C-terminal of the deaminase domain.

Some aspects of this disclosure relate to the recognition that the activity of cytosine deaminase protein variants, such as rAPOBEC1 variants described herein can be directed to a specific site in genomic DNA. Without wishing to be bound by any particular theory, advantages of using Cas9 as a recognition agent include (1) the sequence specificity of Cas9 can be easily altered by simply changing the sgRNA sequence; and (2) Cas9 binds to its target sequence by denaturing the dsDNA, resulting in a stretch of DNA that is single-stranded and therefore a viable substrate for the deaminase. It should be understood that other catalytic domains, or catalytic domains from other deaminases, can also be used to generate fusion proteins with Cas9, and that the disclosure is not limited in this regard. a person of skill in the art will be able to design suitable guide RNAs to target the fusion proteins to a target sequence that comprises a nucleotide to be deaminated.

Some aspects of the disclosure relate to fusion proteins that comprise a uracil glycosylase inhibitor (UGI) domain. In some embodiments, any of the fusion proteins provided herein that comprise a Cas9 domain (e.g., a nuclease active Cas9 domain, a nuclease inactive dCas9 domain, or a Cas9 nickase) may be further fused to a UGI domain either directly or via a linker. Some aspects of this disclosure provide deaminase-dCas9 fusion proteins, deaminase-nuclease active Cas9 fusion proteins and deaminase-Cas9 nickase fusion proteins with increased nucleobase editing efficiency. Without wishing to be bound by any particular theory, cellular DNA-repair response to the presence of U:G heteroduplex DNA may be responsible for the decrease in nucleobase editing efficiency in cells. For example, uracil DNA glycosylase (UDG) catalyzes removal of U from DNA in cells, which may initiate base excision repair, with reversion of the U:G pair to a C:G pair as the most common outcome. In some embodiments, Uracil DNA Glycosylase Inhibitor (UGI) may inhibit human UDG activity. Thus, this disclosure contemplates a fusion protein comprising dCas9-nucleic acid editing domain further fused to a UGI domain. This disclosure also contemplates a fusion protein comprising a Cas9 nickase-nucleic acid editing domain further fused to a UGI domain. It should be understood that the use of a UGI domain may increase the editing efficiency of a nucleic acid editing domain that is capable of catalyzing a C to U change. For example, fusion proteins comprising a UGI domain may be more efficient in deaminating C residues. In some embodiments, the fusion protein comprises the structure:

[deaminase]-[optional linker sequence]-[dCas9]-[optional linker sequence]-[UGI];
[deaminase]-[optional linker sequence]-[UGI]-[optional linker sequence]-[dCas9];
[UGI]-[optional linker sequence]-[deaminase]-[optional linker sequence]-[dCas9];
[UGI]-[optional linker sequence]-[dCas9]-[optional linker sequence]-[deaminase];
[dCas9]-[optional linker sequence]-[deaminase]-[optional linker sequence]-[UGI]; or
[dCas9]-[optional linker sequence]-[UGI]-[optional linker sequence]-[deaminase].

In other embodiments, the fusion protein comprises the structure:
[deaminase]-[optional linker sequence]-[Cas9 nickase]-[optional linker sequence]-[UGI];
[deaminase]-[optional linker sequence]-[UGI]-[optional linker sequence]-[Cas9 nickase];
[UGI]-[optional linker sequence]-[deaminase]-[optional linker sequence]-[Cas9 nickase];
[UGI]-[optional linker sequence]-[Cas9 nickase]-[optional linker sequence]-[deaminase];
[Cas9 nickase]-[optional linker sequence]-[deaminase]-[optional linker sequence]-[UGI]; or
[Cas9 nickase]-[optional linker sequence]-[UGI]-[optional linker sequence]-[deaminase].

In some embodiments, the fusion proteins provided herein do not comprise a linker sequence. In some embodiments, one or both of the optional linker sequences are present.

In some embodiments, the "-" used in the general architecture above indicates the presence of an optional linker sequence. In some embodiments, the fusion proteins comprising a UGI further comprise a nuclear targeting sequence, for example a nuclear localization sequence. In some embodiments, fusion proteins provided herein further comprise a nuclear localization sequence (NLS). In some embodiments, the NLS is fused to the N-terminus of the fusion protein. In some embodiments, the NLS is fused to the C-terminus of the fusion protein. In some embodiments, the NLS is fused to the N-terminus of the UGI protein. In some embodiments, the NLS is fused to the C-terminus of the UGI protein. In some embodiments, the NLS is fused to the N-terminus of the Cas9 protein. In some embodiments, the NLS is fused to the C-terminus of the Cas9 protein. In some embodiments, the NLS is fused to the N-terminus of the deaminase. In some embodiments, the NLS is fused to the C-terminus of the deaminase. In some embodiments, the NLS is fused to the N-terminus of the second Cas9. In some embodiments, the NLS is fused to the C-terminus of the second Cas9. In some embodiments, the NLS is fused to the fusion protein via one or more linkers. In some embodiments, the NLS is fused to the fusion protein without a linker. In some embodiments, the NLS comprises an amino acid sequence of any one of the NLS sequences provided or referenced herein. In some embodiments, the NLS comprises the amino acid PKKKRKV (SEQ ID NO: 35) or MDSLLMNRRKFLYQFKNVRWAKGRRETYLC (SEQ ID NO: 36).

In some embodiments, a UGI domain comprises a wild-type UGI or a UGI as set forth in SEQ ID NO: 22. In some embodiments, the UGI proteins provided herein include fragments of UGI and proteins homologous to a UGI or a UGI fragment. For example, in some embodiments, a UGI domain comprises a fragment of the amino acid sequence set forth in SEQ ID NO: 22. In some embodiments, a UGI fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 22. In some embodiments, a UGI comprises an amino acid sequence homologous to the amino acid sequence set forth in SEQ ID NO: 22 or an amino acid sequence homologous to a fragment of the amino acid sequence set forth in SEQ ID NO: 22. In some embodiments, proteins comprising UGI or fragments of UGI or homologs of UGI or UGI fragments are referred to as "UGI variants." A UGI variant shares homology to UGI, or a fragment thereof. For example a UGI variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild type UGI or a UGI as set forth in SEQ ID NO: 22. In some embodiments, the UGI variant comprises a fragment of UGI, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type UGI or a UGI as set forth in SEQ ID NO: 22. In some embodiments, the UGI comprises the following amino acid sequence:

>splP147391UNGI_BPPB2 Uracil-DNA glycosylase inhibitor MTNLSDIIEKETGKQLVIQE-SILMLPEEVEEVIGNKPESDILVHTAYDEST-DENVMLLTSD APEYKPWALVIQDSNGENKIKML (SEQ ID NO: 22)

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. J. Biol. Chem. 264: 1163-1171(1989); Lundquist et al., Site-directed mutagenesis and characterization of uracil-DNA glycosylase inhibitor protein. Role of specific carboxylic amino acids in complex formation with *Escherichia coli* uracil-DNA glycosylase. J. Biol. Chem. 272:21408-21419(1997); Ravishankar et al., X-ray analysis of a complex of *Escherichia coli* uracil DNA glycosylase (EcUDG) with a proteinaceous inhibitor. The structure elucidation of a prokaryotic UDG. Nucleic Acids Res. 26:4880-4887(1998); and Putnam et al., Protein mimicry of DNA from crystal structures of the uracil-DNA glycosylase inhibitor protein and its complex with *Escherichia coli* uracil-DNA glycosylase. *J. Mol. Biol.* 287:331-346(1999), the entire contents of each are incorporated herein by reference.

Complexes with Guide RNAs (gRNAs)

Some aspects of this disclosure provide complexes comprising any of the fusion proteins provided herein, and a guide RNA bound to a Cas9 domain (e.g., a dCas9, a nuclease active Cas9, or a Cas9 nickase) of the fusion protein.

In some embodiments, the guide RNA is from 15-100 nucleotides long and comprises a sequence of at least 10 contiguous nucleotides that is complementary to a target sequence. In some embodiments, the guide RNA is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. In some embodiments, the guide RNA comprises a sequence of 15, 16, 17, 18, 19, 20, 21, 22, 23, 24, 25, 26, 27, 28, 29, 30, 31, 32, 33, 34, 35, 36, 37, 38, 39, or 40 contiguous nucleotides that is complementary to a target sequence. In some embodiments, the target sequence is a DNA sequence. In some embodiments, the target sequence is a sequence in the genome of a mammal. In some embodiments, the target sequence is a sequence in the genome of a human. In some embodiments, the 3' end of the target sequence is immediately adjacent to a canonical PAM sequence (NGG). In some embodiments, the guide RNA is complementary to a sequence associated with a disease or disorder.

Methods of Use

Some aspects of this disclosure provide methods of using the cytidine deaminase protein variants, fusion proteins, and/or complexes provided herein. For example, some aspects of this disclosure provide methods comprising contacting a DNA molecule (a) with any of the cytidine deaminase protein variants or fusion proteins provided herein, and with at least one guide RNA, wherein the guide RNA is about 15-100 nucleotides long and comprises a sequence of at least 10 contiguous nucleotides that is complementary to a target sequence; or (b) with a RNA-programmable nuclease (e.g., a Cas9 protein, a Cas9 fusion protein, or a Cas9 protein) or fusion protein complex with at least one gRNA as provided herein. In some embodiments, the 3'-end of the target sequence is not immediately adjacent to a canonical PAM sequence (NGG). In some embodiments, the 3'-end of the target sequence is immediately adjacent to an AGC, GAG, TTT, GTG, or CAA sequence.

In some embodiments, the target DNA sequence comprises a sequence associated with a disease or disorder. In some embodiments, the target DNA sequence comprises a point mutation associated with a disease or disorder. In some embodiments, the activity of the cytidine deaminase protein variant, the Cas9 fusion protein, or the complex results in a correction of the point mutation. In some embodiments, the target DNA sequence comprises a T→C point mutation associated with a disease or disorder, and wherein the deamination of the mutant C base results in a sequence that is not associated with a disease or disorder. In some embodiments, the target DNA sequence encodes a protein and wherein the point mutation is in a codon and results in a change in the amino acid encoded by the mutant codon as compared to the wild-type codon. In some embodiments, the deamination of the mutant C results in a change of the amino acid encoded by the mutant codon. In some embodiments, the deamination of the mutant C results in the codon encoding the wild-type amino acid. In some embodiments, the contacting is in vivo in a subject. In some embodiments, the subject has or has been diagnosed with a disease or disorder. In some embodiments, the disease or disorder is cystic fibrosis, phenylketonuria, epidermolytic hyperkeratosis (EHK), Charcot-Marie-Toot disease type 4J, neuroblastoma (NB), von Willebrand disease (vWD), myotonia congenital, hereditary renal amyloidosis, dilated cardiomyopathy (DCM), hereditary lymphedema, familial Alzheimer's disease, HIV, Prion disease, chronic infantile neurologic cutaneous articular syndrome (CINCA), desmin-related myopathy (DRM), a neoplastic disease associated with a mutant PI3KCA protein, a mutant CTNNB1 protein, a mutant HRAS protein, or a mutant p53 protein.

Some embodiments provide methods for using fusion proteins (e.g., base editors) provided herein. In some embodiments, the fusion protein is used to introduce a point mutation into a nucleic acid by deaminating a target nucleobase, e.g., a C residue. In some embodiments, the deamination of the target nucleobase results in the correction of a genetic defect, e.g., in the correction of a point mutation that leads to a loss of function in a gene product. In some embodiments, the genetic defect is associated with a disease or disorder, e.g., a lysosomal storage disorder or a metabolic disease, such as, for example, type I diabetes. In some embodiments, the methods provided herein are used to introduce a deactivating point mutation into a gene or allele that encodes a gene product that is associated with a disease or disorder. For example, in some embodiments, methods are provided herein that employ a Cas9 DNA editing fusion protein to introduce a deactivating point mutation into an oncogene (e.g., in the treatment of a proliferative disease). A deactivating mutation may, in some embodiments, generate a premature stop codon in a coding sequence, which results in the expression of a truncated gene product, e.g., a truncated protein lacking the function of the full-length protein.

In some embodiments, the purpose of the methods provide herein is to restore the function of a dysfunctional gene via genome editing. The Cas9 deaminase fusion proteins provided herein can be validated for gene editing-based human therapeutics in vitro, e.g., by correcting a disease-associated mutation in human cell culture. It will be understood by the skilled artisan that the fusion proteins provided herein, e.g., the fusion proteins comprising a Cas9 domain and a nucleic acid deaminase domain can be used to correct any single point T→C or A→G mutation. In the first case, deamination of the mutant C back to U corrects the mutation, and in the latter case, deamination of the C that is base-paired with the mutant G, followed by a round of replication, corrects the mutation.

It will be apparent to those of skill in the art that in order to target a Cas9:nucleic acid editing enzyme/domain fusion protein as disclosed herein to a target site, e.g., a site comprising a point mutation to be edited, it is typically necessary to co-express the Cas9:nucleic acid editing enzyme/domain fusion protein together with a guide RNA, e.g., an sgRNA. As explained in more detail elsewhere herein, a guide RNA typically comprises a tracrRNA framework allowing for Cas9 binding, and a guide sequence, which confers sequence specificity to the Cas9:nucleic acid editing enzyme/domain fusion protein. In some embodiments, the guide RNA comprises a structure 5'-[guide sequence] guuuuagagcuagaaauagcaaguuaaaauaaggcuaguccguuaucaacuugaaaaaguggcaccgagucggugcuuuuu-3' (SEQ ID NO: 37), wherein the guide sequence comprises a sequence that is complementary to the target sequence.

The guide sequence is typically 20 nucleotides long. The sequences of suitable guide RNAs for targeting Cas9:nucleic acid editing enzyme/domain fusion proteins to specific genomic target sites will be apparent to those of skill in the art based on the instant disclosure. Such suitable guide RNA sequences typically comprise guide sequences that are complementary to a nucleic sequence within 50 nucleotides upstream or downstream of the target nucleotide to be edited.

Some aspects of the disclosure provide methods for editing a nucleic acid. In some embodiments, the method is a method for editing a nucleobase of a nucleic acid (e.g., a base pair of a double-stranded DNA sequence). In some embodiments, the method comprises the steps of: a) contacting a target region of a nucleic acid (e.g., a double-stranded DNA sequence) with a complex comprising a base editor (e.g., a Cas9 domain fused to a cytidine deaminase protein variant) and a guide nucleic acid (e.g., gRNA), wherein the target region comprises a targeted nucleobase pair; b) inducing strand separation of said target region; c) converting a first nucleobase of said target nucleobase pair in a single strand of the target region to a second nucleobase; and d) cutting no more than one strand of said target region, where a third nucleobase complementary to the first nucleobase base is replaced by a fourth nucleobase complementary to the second nucleobase; and the method results in less than 20% indel formation in the nucleic acid.

Vectors and Kits

Some aspects of this disclosure provide expression constructs encoding gene products that select for a desired physiochemical characteristic or desired function of an evolved cytidine deaminase protein, such as rAPOBEC1 in a host cell, e.g., in a bacterial host cell. In some embodiments, a selection system comprises one or more gene products encoded by a nucleic acid (e.g., an isolated nucleic acid). In some embodiments, one or more nucleic acids that are operably linked comprise an expression construct. Expression constructs are sometimes also referred to as vectors. In some embodiments, the expression constructs are plasmids.

In some aspects, the disclosure relates to expression vectors (e.g., plasmids) comprising a gene of interest to be evolved (e.g., a cytidine deaminase protein, such as rAPOBEC1) fused to a sequence encoding a T7 RNA polymerase (RNAP)N-terminal domain. In some embodiments, the plasmid is a selection plasmid (e.g., selection phagemid). In some embodiments, the expression construct comprises a nucleic acid encoding a cytidine deaminase protein is contiguous (e.g., operably linked) to the nucleic acid sequence encoding the T7 RNAP N-terminal domain. In some embodiments, the 3'-end of the nucleic acid encoding the cytidine deaminase protein is contiguous (e.g., operably linked) to the 5'-end of the nucleic acid encoding the T7 RNAP N-terminal domain. In some embodiments, the expression construct further comprises a promoter, such as a $P_{BAD}$ promoter.

An N-terminal domain of a T7 RNAP may comprise between about 1% and about 99% (e.g., any percentage between 1% and 99%), about 10% and about 80%, or about 30% and about 60% of the amino acid residues of a full-length T7 RNAP (e.g., about 1% to about 99% of the amino acid residues of NCBI Accession No. NC_041960.1). In some embodiments, a T7 RNAP N-terminal domain comprises between 1 and 800 amino acid (e.g., any integer between 1 and 800, inclusive) truncations relative to the C-terminus of wild-type T7 RNAP (e.g., NCBI Accession No. NC_041960.1). For example, in some embodiments, an N-terminal domain of T7 RNAP comprises amino acid residues 1-50, 1-100, 1-150, 1-300, 1-400, 1-500, or 1-800 of NCBI Accession No. NC_041960.1.

In some aspects, the disclosure relates to expression vectors (e.g., plasmids) comprising an isolated nucleic acid having a sequence encoding a T7 RNA polymerase (RNAP) C-terminal domain. In some embodiments, the expression vector (e.g., plasmid) is an accessory plasmid. Without wishing to be bound by any particular theory, expression of a C-terminal domain of T7 RNAP in a cell (e.g., a host cell) in which a properly-folded fusion protein (e.g., comprising a gene of interest fused to a T7 RNAP N-terminal domain) is expressed, results in reconstitution of a functional T7 RNAP. A C-terminal domain of a T7 RNAP may comprise between about 1% and about 99% (e.g., any percentage between 1% and 99%), about 10% and about 80%, or about 30% and about 60% of the amino acid residues of a full-length T7 RNAP (e.g., about 1% to about 99% of the amino acid residues of NCBI Accession No. NC_041960.1). In some embodiments, a T7 RNAP C-terminal domain comprises between 1 and 800 amino acid (e.g., any integer between 1 and 800, inclusive) truncations relative to the N-terminus of wild-type T7 RNAP (e.g., NCBI Accession No. NC_041960.1). For example, in some embodiments, an N-terminal domain of T7 RNAP comprises amino acid residues 50-883, 100-883, 200-883, 400-884, or 500-883 of NCBI Accession No. NC_041960.1.

In some aspects, the disclosure relates to expression vectors (e.g., plasmids) comprising a cytidine deaminase protein to be evolved fused to a sequence encoding a T7 RNA polymerase (RNAP)N-terminal domain further comprises a nucleic acid encoding a split intein portion (e.g., fragment). An "intein" refers to a protein that is able to self-catalytically excise itself and join the remaining protein fragments (e.g., exteins) by the process of protein splicing. Generally, the self-splicing function of inteins makes them useful tools for engineering trans-spliced recombinant proteins, as described in U.S. Publication No. 2003-0167533, the entire contents of which are incorporated herein by reference. For example, expressing (i) a nucleic acid sequence encoding a N-terminal intein fragment (or portion) operably linked to a nucleic acid encoding a first protein fragment (A), and (ii) a nucleic acid encoding a C-terminal intein fragment (or portion) operably linked to a nucleic acid encoding a second protein fragment (B), in a cell would result, in some embodiments, in trans-splicing of the inteins within the cell to produce a fusion molecule comprising (in the following order) "A-B".

Inteins are present in both prokaryotic and eukaryotic organisms. In some embodiments, an intein is a bacterial intein, such as a cyanobacterial intein (e.g., intein from *Synechocystis* or *Nostoc*). In some embodiments, the intein is a *Nostoc punctiforme* (Npu) intein, for example as described in Oeemig et al. (2009) *FEBS Lett.* 583(9):1451-6.

In some embodiments, an expression construct described herein comprises a nucleic acid encoding a split intein portion (e.g., a split intein N-terminal portion or split intein C-terminal portion) operably linked to a nucleic acid encoding a gene required for the production of infectious phage particles, such as gIII protein (pIII protein), or a portion (e.g., fragment) thereof. In some embodiments, the split intein portion is a split intein C-terminal portion (e.g., a Npu split intein C-terminal portion). In some embodiments, the split intein C-terminal portion is positioned upstream of (e.g., 5' relative to) the nucleic acid encoding the gene required for the production of infectious phage particles, or portion thereof. In some embodiments, the split intein portion is a split intein N-terminal portion (e.g., a Npu split intein N-terminal portion). In some embodiments, the split intein N-terminal portion is positioned downstream of (e.g., 3' relative to) the nucleic acid encoding the gene required for the production of infectious phage particles, or portion thereof.

In some embodiments, the nucleic acid encoding a gene required for the production of infectious phage particles, such as gIII protein (pIII protein), is truncated (e.g., missing one or more nucleic acid bases relative to a full-length gene encoding pIII protein). In some embodiments, the nucleic acid is 1, 2, 3, 4, 5, 6, 7, 8, 9, 10, or more nucleic acid bases shorter than a full-length gene encoding pIII protein. It should be appreciated that the nucleic acid encoding truncated pIII protein may be truncated at either the 5'-end or the 3'-end. However, in preferred embodiments, the nucleic acid is truncated at the 5'-end. In some embodiments, the gene product encoded by the truncated nucleic acid lacks a full-length N-terminal signal peptide. In some embodiments, the gene product lacks amino acid residues 1-10 of a gIII protein signal peptide. In some embodiments, the gene product lacks amino acid residues 1-11, 1-12, 1-13, 1-14, 1-15, 1-16, 1-17, or 1-18 (e.g., the entire signal peptide) of pIII. In some embodiments, a portion of a pIII protein comprises the sequence set forth in SEQ ID NO: 38 (MKKLLPAIP). In some embodiments, a portion of a pIII protein comprises the sequence set forth in SEQ ID NO: 39:

VVPFYSHSAETVESCLAKPHTENSFTNVWKDDKTLDRYANYEGCLWNATG

VVVCTGDETQCYGTWVPIGLAIPENEGGGSEGGGSEGGGSEGGGTKPPEY

GDTPIPGYTYINPLDGTYPPGTEQNPANPNPSLEESQPLNTFMFQNNRFR

NRQGALTVYTGTVTQGTDPVKTYYQYTPVSSKAMYDAYWNGKFRDCAFHS

GFNEDPFVCEYQGQSSDLPQPPVNAGGGSGGGSGGGSEGGGSEGGGSEGG

GSEGGGSGGGSGSGDFDYEKMANANKGAMTENADENALQSDAKGKLDSVA

TDYGAAIDGFIGDVSGLANGNGATGDFAGSNSQMAQVGDGDNSPLMNNFR

QYLPSLPQSVECRPFVFGAGKPYEFSIDCDKINLFRGVFAFLLYVATFMY

VFSTFANILRNKES.

In some embodiments, expression constructs (e.g., plasmids), or combinations of expression constructs (e.g. combinations of plasmids) described herein may be used as a bacterial 2-hybrid system to positively select for evolved cytidine deaminase protein variants having desirable physiochemical characteristics (e.g., solubility, stability, etc.) or desirable function. In the context of PACE, bacterial 2-hybrid selections have been described, for example in International PCT Application, PCT/US2016/043559, filed Jul. 22, 2016, published as WO 2017/015559 on Jan. 26, 2017, and Badran et al. (2016) *Nature* 533:58-63, the entire contents of each of which are incorporated herein by reference.

In some embodiments, a bacterial 2-hybrid system comprises a first expression construct comprising a nucleic acid encoding a split intein C-terminal portion fused (e.g., operably linked) to a gene encoding a truncated gIII as described herein, and a second expression construct comprising a nucleic acid encoding a split intein N-terminal portion fused (e.g., operably linked) to a gene encoding a truncated gIII, where expression of the first expression construct and the second expression construct in a cell results in reconstitution (e.g., protein splicing) of a full-length functional pIII protein. In some embodiments, the first expression construct is operably linked to a promoter, such as a T7 RNAP promoter. In some embodiments, the first expression construct or the second expression construct further comprises a nucleic acid encoding a phage repressor protein, for example 434 cI repressor protein. In some embodiments, the first expression construct or the second expression construct is encodes a fusion protein comprising 434 cI repressor protein and the SH2 domain of an ABL1 kinase.

The first expression construct and the second expression construct can be located on the same vector (e.g., plasmid) or on separate vectors (e.g., different plasmids). In some embodiments, the vector is an accessory plasmid (AP). In some embodiments, a bacterial 2-hybrid system comprises a third expression construct comprising a nucleic acid encoding a cytidine deaminase protein, such as rAPOBEC1, to be evolved, T7 RNAP N-terminal domain, and an RNA polymerase subunit. In some embodiments, the RNA polymerase is RNA polymerase subunit omega (RpoZ). In some embodiments, the first expression construct, second expression construct, or third expression construct comprises a nucleic acid encoding a T7 RNAP C-terminal domain.

In some aspects, the disclosure provides expression constructs (e.g., plasmids) comprising an isolated nucleic acid encoding a leucine zipper domain of the yeast GCN4 transcription factor ("GCN4 tag") fused upstream of the protein of the cytidine deaminase protein to be evolved. In some embodiments the expression construct is a selection plasmid (SP). For example, using a split intein system described elsewhere in the disclosure, two simultaneous PACE selections are run: the first is a split T7 RNAP-based solubility selection, and the second is a protein binding selection with an accessory plasmid (AP) encoding the anti-GCN4 scFv m3, which recognizes the GCN4 tag. The T7 RNAP based solubility selection evolves for increased protein solubility, while the GCN4 tag protein binding selection prevents potential cheating in the same way as an activity-dependent selection.

Some aspects of this disclosure provide a cell comprising an expression construct or a plasmid as provided herein. In some embodiments, the cell is a bacterial cell. In some embodiments, the cell further comprises a selection plasmid or an accessory plasmid. In some embodiments, the cell is a host cell for a bacteriophage. In some embodiments, the cell is an *E. coli* cell. In some embodiments, the cell is comprised in a lagoon.

Some aspects of this disclosure provide a vector system comprising: (i) a selection phagemid comprising an isolated nucleic acid comprising an expression construct encoding a fusion protein comprising, in the following order: a GCN4 peptide, a cytidine deaminase protein, a T7 RNA polymerase, and an *E. coli* RNA polymerase omega subunit (rpoZ); (ii) a first accessory plasmid comprising an isolated nucleic acid comprising an expression construct encoding a RNA polymerase I promoter operably linked to an expression cassette comprising, in the following order: a sequence encoding a M13 phage gIII protein signal peptide, and a sequence encoding a Npu split intein N-terminal portion, wherein the sequence encoding the gIII protein signal peptide lacks one or more nucleic acid bases of the signal peptide domain; and (iii) a second accessory plasmid comprising an isolated nucleic acid comprising an expression construct encoding a T7 promoter operably linked to an expression cassette comprising, in the following order: a sequence encoding a Npu split intein C-terminal portion, and a sequence encoding a M13 phage gIII protein, wherein the sequence encoding the gIII protein lacks one or more nucleic acid bases in the signal peptide domain.

In some embodiments, a vector system is provided as part of a kit, which is useful, in some embodiments, for performing SE-PACE to produce cytidine deaminase protein variants. For example, in some embodiments, a kit comprises a first container housing the selection phagemid of the vector system, a second container housing the first accessory plasmid of the vector system, and a third container housing the second accessory plasmid of the vector system. In some embodiments, a kit further comprises a mutagenesis plasmid. Mutagenesis plasmids for PACE are generally known in the art, and are described, for example in International PCT Application No. PCT/US2016/027795, filed Sep. 16, 2016, published as WO 2016/168631, the entire contents of which are incorporated herein by reference. In some embodiments, the kit further comprises a set of written or electronic instructions for performing SE-PACE.

EXAMPLE

General methods: Antibiotics (Gold Biotechnology) were used at the following working concentrations: carbenicillin 50 µg/mL, spectinomycin 50 µg/mL, chloramphenicol 25 µg/mL, kanamycin 50 µg/mL, tetracycline 10 µg/mL, streptomycin 50 µg/mL. HyClone water (GE Healthcare Life Sciences) was used for PCR reactions and cloning. For all other experiments, water was purified using a MilliQ purification system (Millipore). Phusion U Hot Start DNA polymerase (Thermo Fisher Scientific) was used for all PCRs. Plasmids and selection phages (SPs) were cloned by USER assembly. Genes were obtained as synthesized gBlock gene fragments from Integrated DNA Technologies or PCR amplified directly from *E. coli* genomic DNA. Plasmids were cloned and amplified using either Mach1 (Thermo Fisher Scientific) or Turbo (New England BioLabs) cells. Unless otherwise noted, plasmid or SP DNA was amplified using the Illustra Templiphi 100 Amplification Kit (GE Healthcare Life Sciences) prior to Sanger sequencing.

Preparation and transformation of chemically competent cells: Strain S2060 was used in all luciferase, phage propagation, and plaque assays, and in all PACE experiments. To prepare competent cells, an overnight culture was diluted 1000-fold into 50 mL of 2× YT media (United States Biologicals) supplemented with tetracycline and streptomycin and grown at 37° C. with shaking at 230 RPM to $OD_{600}$~0.4-0.6. Cells were pelleted by centrifugation at 4000 g for 10 minutes at 4° C. The cell pellet was then resuspended by gentle stirring in 2 mL of ice-cold LB media (United States Biologicals) 2 mL of 2×TSS (LB media supplemented with 5% v/v DMSO, 10% w/v PEG 3350, and 20 mM $MgCl_2$) was added. The cell suspension was stirred to mix completely, aliquoted and frozen on dry ice, and stored at −80° C. until use.

To transform cells, 100 µL of competent cells thawed on ice was added to a pre-chilled mixture of plasmid (2 µL each; up to 3 plasmids per transformation) in 95 µL KCM solution (100 mM KCl, 30 mM $CaCl_2$), and 50 mM $MgCl_2$ in $H_2O$) and stirred gently with a pipette tip. The mixture was incubated on ice for 10 min and heat shocked at 42° C. for 75 s before 600 µL of SOC media (New England BioLabs) was added. Cells were allowed to recover at 37° C. with shaking at 230 RPM for 1.5 h, streaked on 2× YT media+1.5% agar (United States Biologicals) plates containing the appropriate antibiotics, and incubated at 37° C. for 16-18 h.

Phage propagation assay: S2060 cells were transformed with the accessory plasmids AP(s) of interest. Overnight cultures of single colonies grown in 2× YT media supplemented with maintenance antibiotics were diluted 1000-fold into DRM media with maintenance antibiotics and grown at 37° C. with shaking at 230 RPM to $OD_{600}$~0.4-0.6. Cells were then infected with SP at a starting titer of $5 \times 10^4$ pfu/mL. Cells were incubated for another 16-18 h at 37° C. with shaking at 230 RPM, then centrifuged at 8000 g for 2 min. The supernatant containing phage was removed and stored at 4° C. until use.

Plaque assay: S2060 cells were transformed with the AP(s) of interest. Overnight cultures of single colonies grown in 2× YT media supplemented with maintenance antibiotics were diluted 1000-fold into fresh 2× YT media with maintenance antibiotics and grown at 37° C. with shaking at 230 RPM to $OD_{600}$~0.6-0.8 before use. SP were serially diluted 100-fold (4 dilutions total) in $H_2O$. 150 µL of cells was added to 10 µL of each phage dilution and to this 1 mL of liquid (55° C.) top agar (2× YT media+0.6% agar) supplemented with 2% Bluo-gal (Gold Biotechnology) was added and mixed by pipetting up and down once. This mixture was then immediately pipetted onto one quadrant of a quartered Petri dish already containing 2 mL of solidified bottom agar (2× YT media+1.5% agar, no antibiotics). After solidification of the top agar, plates were incubated at 37° C. for 16-18 h.

Phage-assisted continuous evolution (PACE): Unless otherwise noted, PACE apparatus, including host cell strains, lagoons, chemostats, and media, were all used as previously described. To reduce the likelihood of contamination with gIII-encoding recombined SP, phage stocks were purified.

Chemically competent S2060s were transformed with AP(s) and MP6 or DP6 as described above, plated on 2× YT media+1.5% agar supplemented with 25 mM glucose (to prevent induction of mutagenesis) in addition to maintenance antibiotics, and grown at 37° C. for 18-20 h. Four colonies were picked into 1 mL DRM each in a 96-well deep well plate, and this was diluted 5-fold eight times serially into DRM. The plate was sealed with a porous sealing film and grown at 37° C. with shaking at 230 RPM for 16-18 h. Dilutions with $OD_{600}$~0.4-0.8 were then used to inoculate a chemostat containing 80 mL DRM. The chemostat was grown to $OD_{600}$~0.8-1.0, then continuously diluted with fresh DRM at a rate of ~1.5 chemostat volumes/h as previously described[17]. The chemostat was maintained at a volume of 60-80 mL.

Prior to SP infection, lagoons were continuously diluted with culture from the chemostat at 1 lagoon volume/h and pre-induced with 10 mM arabinose for at least 2 h. If DP6 was used, the lagoons were also pre-induced with aTc. Lagoons were infected with SP at a starting titer of $10^6$ pfu/mL and maintained at a volume of 15 mL. Samples (500 µL) of the SP population were taken at indicated times from lagoon waste lines. These were centrifuged at 8000 g for 2 min, and the supernatant was passed through a 0.22 µm PVDF Ultrafree centrifugal filter (Millipore) and stored at 4° C. Lagoon titers were determined by plaque assays using S2060 cells transformed with pJC175e. For Sanger sequencing of lagoons, single plaques were PCR amplified using primers AB1793

(5'-TAATGGAAACTTCCTCATGAAAAAGTCTTTAG; SEQ ID NO: 40)

and AB1396

(5'-ACAGAGAGAATAACATAAAAACAGGGAAGC; SEQ ID NO: 41), both of which anneal to regions of the phage backbone flanking the evolving gene of interest. Generally, eight plaques were picked and sequenced per lagoon.

Activity Independent SE-PACE of rAPOBEC1: Host cells transformed with pTW084b, pTW051d, and DP6 were maintained in a 40 mL chemostat. The lagoon was cycled at 1 volume/h with 10 mM arabinose and 20 ng/mL aTc for 4 h prior to infection with SP30. Upon infection, lagoon dilution rates were decreased to 0.5 volume/h. At 18 h, the aTc concentration was decreased to 0 ng/mL. The lagoon dilution rate was increased to 1 volume/h at 28 h and 1.5 volumes/h at 66 h. The experiment ended at 74 h.

Evolution was continued on host cells transformed with pTW084b, pTW051d, and MP6 in an 80 mL chemostat. Lagoons were infected with a 1:1 ratio of 35.1 and 35.2, SP clones isolated from the previous experiment. Upon infection, lagoon dilution rates were maintained at 1 volume/h.

The lagoon dilution rate was increased to 1.5 volume/h at 18 h, 2 volumes/h at 66 h, and 3 volumes/h at 90 h. The experiment ended at 112 h.

Evolution was continued on host cells transformed with pTW084b, pTW051b4, and MP6 in an 80 mL chemostat. Lagoons were infected with either 36.1 or 36.2, SP clones isolated from the previous experiment. Upon infection, lagoon dilution rates were decreased to 0.5 volume/h. The lagoon dilution rate was increased to 1 volume/h at 17 h, 1.5 volumes/h at 41 h, and 2 volumes/h at 66 h. At 96 h, the chemostat was replaced with a fresh 80 mL chemostat containing host cells transformed with pTW084b, pTW051d2, and MP6, and the lagoon dilution rate was decreased to 1 volume/h. The lagoon dilution rate was increased to 1.5 volumes/h at 115 h and 2 volumes/h at 168 h. The experiment ended at 184 h.

Small-scale protein expression: BL21 DE3 cells (New England BioLabs) were transformed with the expression plasmids (EPs) of interest according to manufacturer protocol. Overnight cultures of single colonies grown in 2× YT media supplemented with maintenance antibiotics were diluted 1000-fold into fresh 2× YT media (2 mL) with maintenance antibiotics and grown at 37° C. with shaking at 230 RPM to $OD_{600}$~0.4-0.6 before induction with 1 mM isopropyl-β-D-thiogalactoside (IPTG; Gold Biotechnology) or rhamnose (Gold Biotechnology). Cells were grown for a further 3 h at 37° C. with shaking at 230 RPM. Cells from 1.4 mL of culture were isolated by centrifugation at 8000 g for 2 min. The resulting pellet was resuspended in 150 µL B-per reagent (Thermo Fisher Scientific) supplemented with protease inhibitor cocktail (Roche) and incubated on ice for 10 min before centrifugation at 16,000 g for 2 min. The supernatant was collected as the soluble fraction and the resulting pellet was resuspended in an additional 150 µL B-per reagent to obtain the insoluble fraction. To 37.5 µL of each fraction was added 12.5 µL 4× Laemmli sample loading buffer (Bio-Rad) containing 2 mM Dithiothreitol (DTT; Sigma Aldrich). After vortexing, the fractions were incubated at 95° C. for 10 min. 12 µL of each soluble fraction and 6 µL of each insoluble fraction was loaded into the wells of a Bolt 4-12% Bis-Tris Plus (Thermo Fisher Scientific) pre-cast gel. 6 µL of Precision Plus Protein Dual Color Standard (Bio-Rad) was used as a reference. Samples were separated by electrophoresis at 180 V for 35 min in Bolt MES SDS running buffer (Thermo Fisher Scientific). Gels were stained with InstantBlue reagent (Expedeon) for 1 h to overnight, then washed several times with $H_2O$ before imaging with a G:Box Chemi XRQ (Syngene). Band densities were quantified using ImageJ and normalized to reference bands to control for protein loading.

Medium-scale protein expression and purification: BL21 DE3 cells were transformed with the EPs of interest according to manufacturer protocol. Overnight cultures of single colonies grown in 2× YT media supplemented with maintenance antibiotics were diluted 1000-fold into fresh 2× YT media (250 mL) with maintenance antibiotics and grown at 37° C. with shaking at 230 RPM to $OD_{600}$~0.4-0.6. Cells were chilled on ice for 1 h, then induced with 1 mM IPTG and grown for a further 16-18 h at 16° C. with shaking at 200 RPM. For 37° C. post-induction growth, the cold shock step was omitted and the cells were grown for a further 3 h at 37° C. with shaking at 200 RPM after induction with 1 mM IPTG. Cells were isolated by centrifugation at 8000 g for 10 min. The resulting pellet was resuspended in 4 mL B-per reagent supplemented with EDTA-free protease inhibitor cocktail (Roche) and incubated on ice for 20 min before centrifugation at 12,000 g for 15 min. The supernatant was decanted into a 15 mL conical tube and incubated with 250 µL of TALON Cobalt (Clontech) resin at 4° C. with constant agitation for 1-2 h, after which the resin was isolated by centrifugation at 500 g for 5 min. The supernatant was decanted, and the resin resuspended in 2 mL binding buffer (50 mM $NaH_2PO_4$, 300 mM NaCl, 20 mM imidazole, pH 7.8) and transferred to a column. The resin was washed 4× with 1 mL binding buffer before protein was eluted with 1 mL of binding buffer containing increasing concentrations of imidazole (50-250 mM in 50 mM increments). The fractions were analyzed by SDS-PAGE for purity. Combined fractions were buffer-exchanged with TBS (20 mM Tris-Cl, 500 mM NaCl, pH 7.5) and concentrated using an Amicon Ultra-15 centrifugal filter unit (10,000 molecular weight cutoff; Millipore), then stored at 4° C. until further use. Proteins were quantified using Quick Start Bradford reagent (Bio-Rad) using BSA standards (Bio-Rad).

Medium-scale BE3 expression and purification: BE3 variants were expressed and purified. BL21 DE3 cells were transformed with the BE3-expressing EPs of interest according to manufacturer protocol. Overnight cultures of single colonies grown in 2× YT media supplemented with maintenance antibiotics were diluted 1000-fold into fresh 2× YT media (200 mL) with maintenance antibiotics and grown at 37° C. with shaking at 230 RPM to $OD_{600}$~0.7-0.8. Cells were chilled on ice for 1 h, then induced IPTG and grown for a further 16-18 h at 16° C. with shaking at 200 RPM. Cells were isolated by centrifugation at 8000 g for 15 min. The resulting pellet was resuspended in 8 mL high salt buffer (100 mM Tris-Cl, 1 M NaCl, 5 mM tris(2-carboxyethyl) phosphine (TCEP; Gold Biotechnology), 20% glycerol, pH 8.0) supplemented with EDTA-free protease inhibitor cocktail and 1 mM phenylmethane sulfonyl fluoride (PMSF; Sigma-Aldrich). Cells were sonicated on ice (3 s on/3 s off; 6 min total) and the lysate centrifuged at 16,000 g for 15 min. The supernatant was decanted into a 15 mL conical tube and incubated with 500 µL of TALON Cobalt resin at 4° C. with constant agitation for 1 h, after which the resin was isolated by centrifugation at 500 g for 5 min. The resin was washed 5× with 1 mL high salt buffer, then eluted with 1 mL of elution buffer (100 mM Tris-Cl, 500 mM NaCl, 5 mM TCEP, 200 mM imidazole, 20% glycerol, pH 8.0). The isolated protein was then buffer-exchanged with medium salt buffer (100 mM Tris-Cl, 500 mM NaCl, 5 mM TCEP, 20% glycerol, pH 8.0) and concentrated using an Amicon Ultra-15 centrifugal filter unit (100,000 molecular weight cutoff). Proteins were quantified using Quick Start Bradford reagent using BSA standards.

Rifampicin resistance assay: BL21 DE3 cells were transformed with the EPs of interest according to manufacturer protocol. Overnight cultures of single colonies grown in DRM media supplemented with maintenance antibiotics were diluted 1000-fold into DRM media with maintenance antibiotics in a 96-well deep well plate. The plate was sealed with a porous sealing film and grown at 37° C. with shaking at 230 RPM for until the culture reached $OD_{600}$~0.4. The cells were then either induced with 5 mM rhamnose or repressed with 5 mM glucose before incubation for an additional 16-18 h at 37° C. with shaking at 230 RPM. Cultures were serially diluted on 2× YT+1.5% agar plates supplemented with 50 µg/mL spectinomycin, 100 µg/mL rifampin (Alfa Aesar), and 25 mM glucose. The total number of colony-forming units (cfus) was determined by serially diluting the same cultures on 2× YT+1.5% agar plates supplemented with 50 µg/mL spectinomycin and 25 mM glucose. Plates were grown at 37° C. for 16-18 h. The surviving colonies on the plates containing rifampin were counted and this number was normalized to the total cfu count.

High-throughput sequencing of genomic DNA: Genomic sites were amplified with primers targeting the region of interest and the appropriate universal Illumina forward and reverse adapters. 25 µL scale PCR 1 reactions used 1.25 µL each of 10 µM forward and reverse primers and 0.5 µL genomic DNA extract, all diluted to 12.5 µL with nuclease-free water, and 12.5 µL Phusion U Green Multiplex PCR MasterMix (Thermo Fisher Scientific). PCR 1 conditions: 98° C. for 2 min, then 30 cycles of (98° C. for 15 s, 61° C. for 20 s, 72° C. for 15 s), followed by a final 72° C. extension for 2 min. PCR products were verified by comparison with DNA standards (Quick-Load 2-Log Ladder; New England BioLabs) on a 2% agarose gel supplemented with ethidium bromide. Unique Illumina barcoding primers which anneal to the universal Illumina adapter region were subsequently appended to each PCR 1 sample in a second PCR reaction (PCR 2). PCR 2 reactions used 1.25 µL each of 10 µM forward and reverse Illumina barcoding primers and 1 µL of unpurified PCR 1 reaction product, all diluted to 12.5 µL with nuclease-free water, and 12.5 µL Phusion U Green Multiplex PCR MasterMix (Thermo Fisher Scientific). PCR 2 conditions: 98° C. for 2 min, then 12 cycles of (98° C. for 15 s, 61° C. for 20 s, 72° C. for 20 s), followed by a final 72° C. extension for 2 min. PCR products were pooled and purified by electrophoresis with a 2% agarose gel using a Monarch DNA Gel Extraction Kit (New England BioLabs) eluting with 30 µL $H_2O$. DNA concentration was quantified with the KAPA Library Quantification Kit-Illumina (KAPA Biosystems) and sequenced on an Illumina MiSeq instrument (paired-end read—R1: 220 cycles, R2: 0 cycles) according to the manufacturer's protocols.

General HTS data analysis: Sequencing reads were demultiplexed in MiSeq Reporter (Illumina). Alignment of amplicon sequences to a reference sequence was performed using a custom Matlab script. In brief, the Smith-Waterman algorithm was used to align sequences without indels to a reference sequence; bases with a quality score of less than 30 were converted to 'N' to prevent base miscalling as a result of sequencing error. Indels were quantified separately using a modified version of a previously described Matlab script in which sequencing reads with more than half the base calls below a quality score of Q30 were filtered out. Indels were counted as reads which contained insertions or deletions of greater than or equal to 1 bp within a 30 bp window surrounding the predicted Cas9 cleavage site.

Base editing values are representative of N=4 independent biological replicates collected over different days, with the mean±s.e.m shown. Base editing values are reported as a percentage of the number of reads with cytidine mutagenesis over the combined number of aligned reads and indel-containing reads.

Data availability: Selection plasmids used in this example will be available through Addgene and are described in Table 2.

Evolution of rAPOBEC1

This example relates to a phage-assisted continuous evolution (PACE) system for rapidly evolving proteins with improved soluble protein expression in *E. coli*, either in the presence or absence of a simultaneous selection for protein function. The system uses an AND logic gate that enables PACE under two simultaneous positive selections. In particular, this example describes activity-independent evolution of APOBEC1 cytidine deaminase variants characterized by improved solubility, enhanced purification yields, and editing activity of base editors in *E. coli* and mammalian cells.

In some embodiments, an activity-independent selection for improving protein expression provides a useful complement to a dual (e.g., positive and negative) selection PACE system. Here, activity-independent, soluble expression PACE (SE-PACE) methods were used to address the primary source of "cheating" observed with evolution based on split T7 RNAP folding reporter—the formation of premature truncation products upstream of translation-initiating Met residues.

Figure 1B:
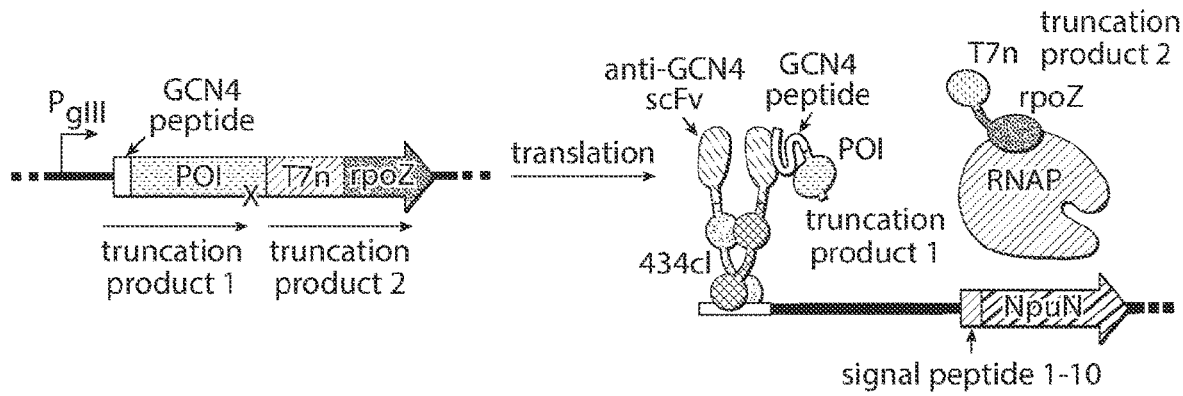

One embodiment of SE-PACE is depicted in FIGS. 1A-1B. Briefly, a protein of interest (POI) is fused between an affinity tag (e.g., a GCN4 peptide) and an *E. coli* T7 RNA polymerase variant-*E. coli* RNA polymerase omega subunit fusion protein (T7n-rpoZ), allowing both the protein expression and protein binding selections to operate (FIG. 1A). As the PACE selection phages (SP) carry the GCN4 peptide linked to rpoZ, they begin PACE with the ability to pass the protein binding selection. Any SP that cheat by forming truncations in the POI lose the ability to propagate on the protein binding selection, as the GCN4 peptide is no longer connected to rpoZ, and thus cheating phages are washed out of the lagoon (FIG. 1B).

Figure 2A:
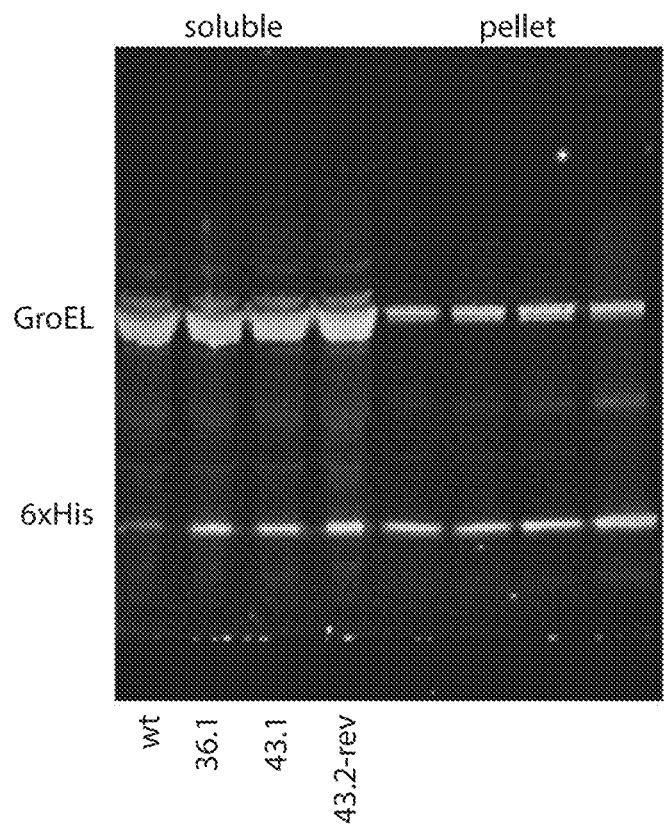
Figure 2A:
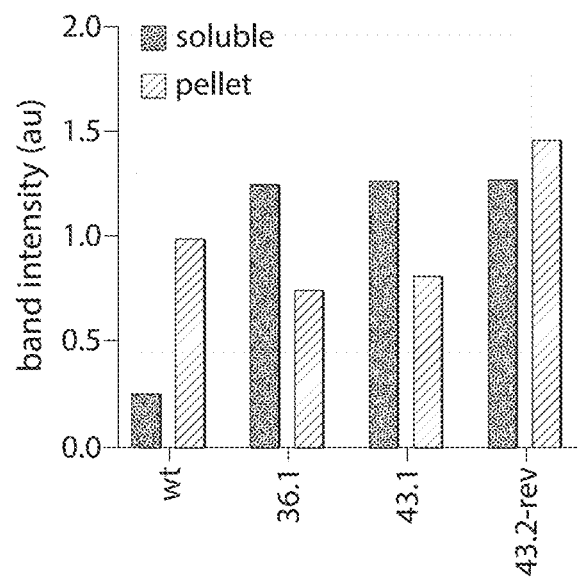
Figure 3A:
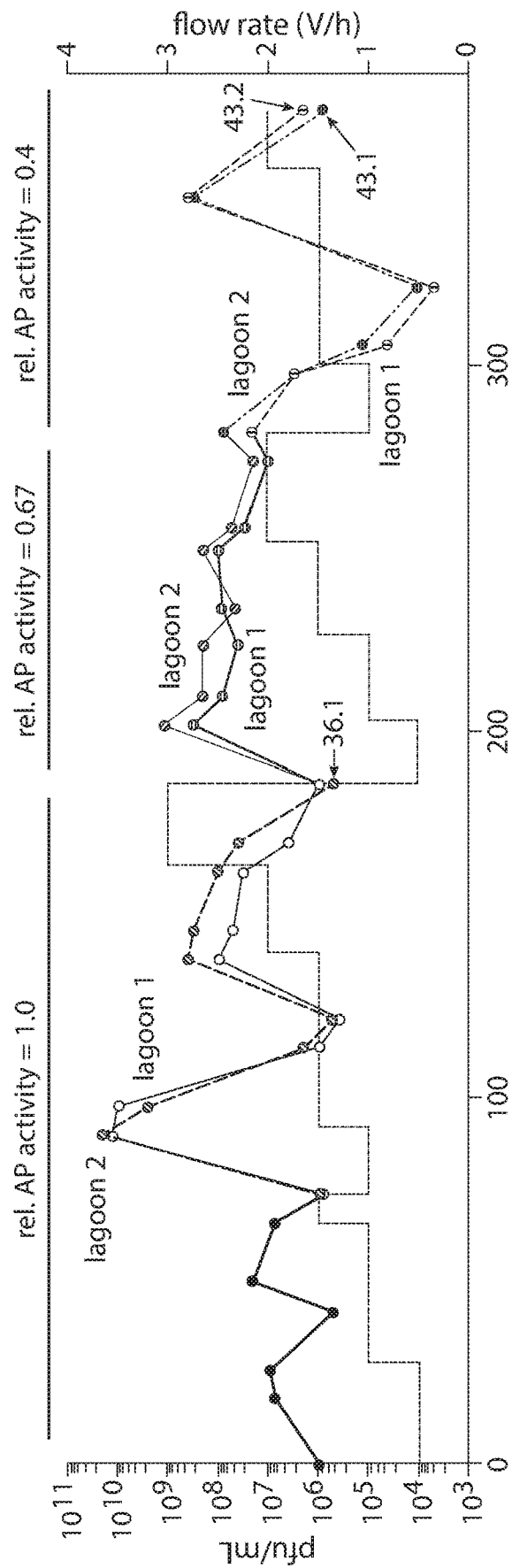
FIGS. 3A-3D show activity-independent selection for rAPOBEC1 protein variants in SE-PACE.
Figure 3C:
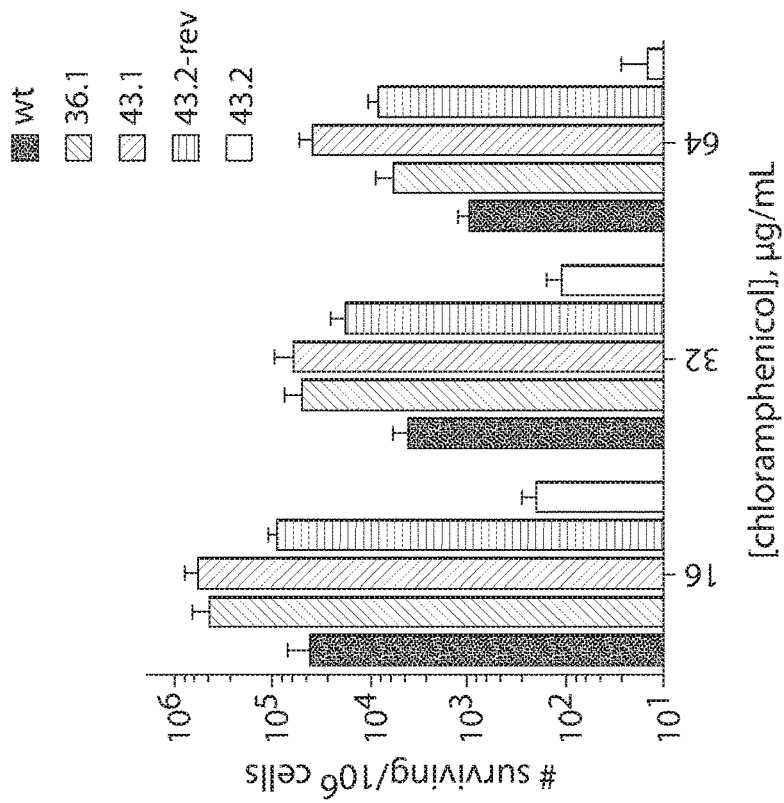
Figure 3B:
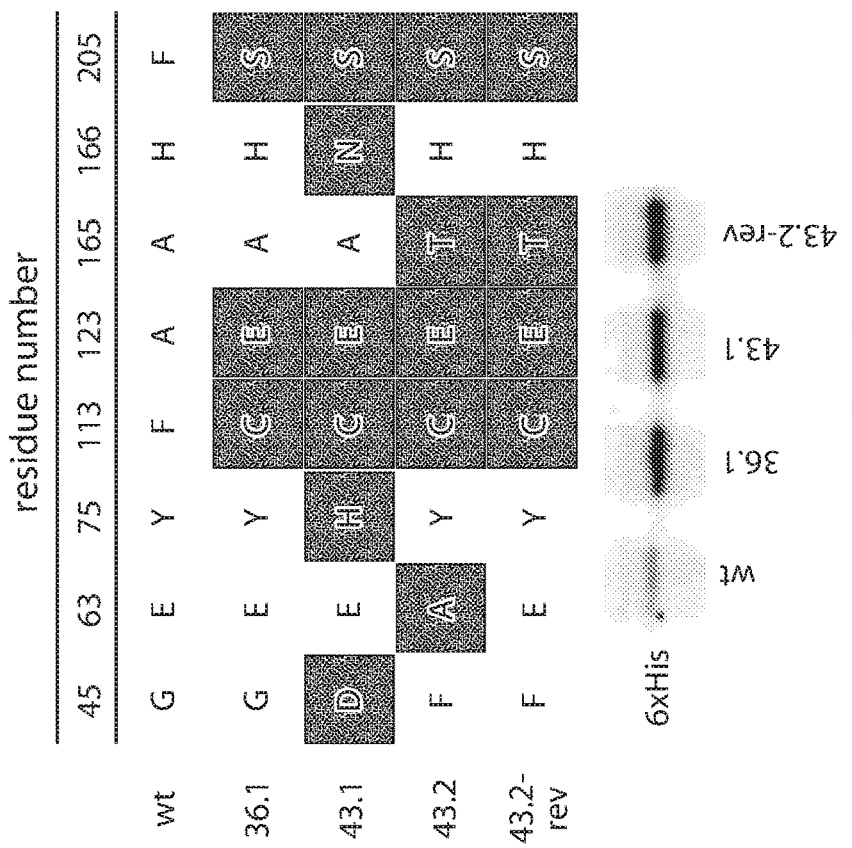
Figure 4A:
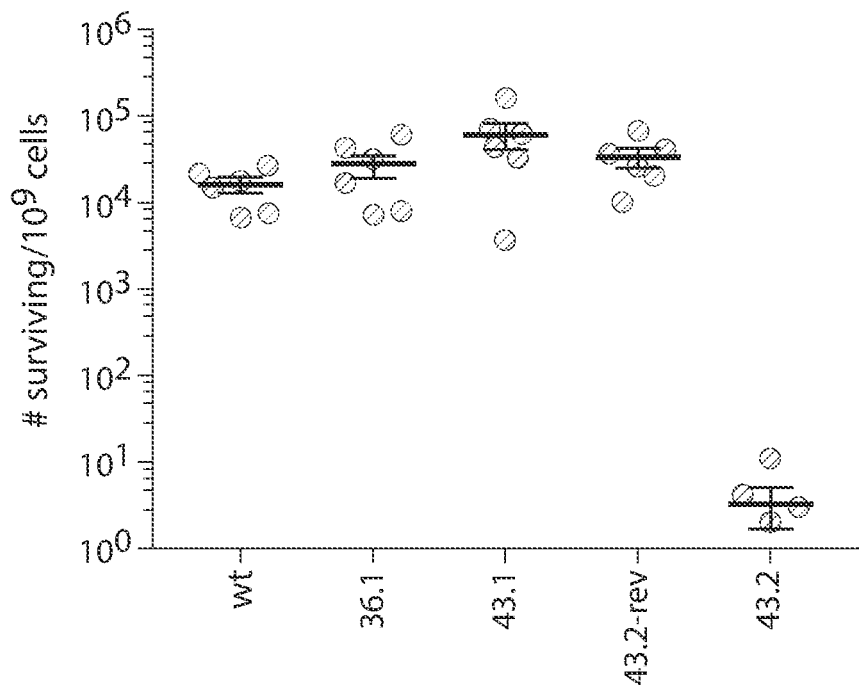
FIGS. 4A-4B show activity of rAPOBEC1 variants in BL21 cells.
Figure 4B:
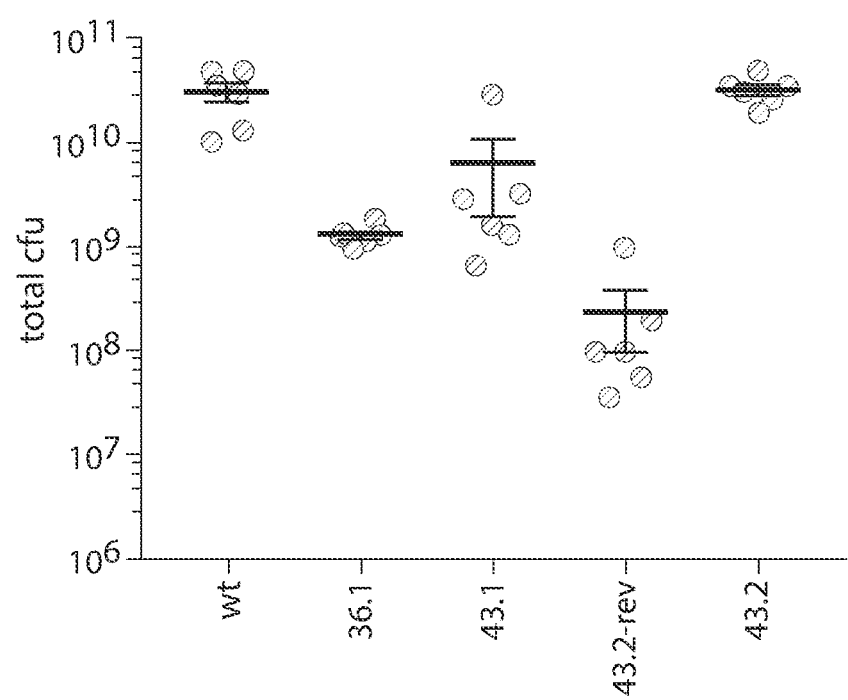

SE-PACE was used to improve the soluble expression of rat apolipoprotein B mRNA editing catalytic subunit 1 (rAPOBEC1). APOBEC1 is a potent cytidine deaminase that can act on both RNA and DNA. Like many eukaryotic proteins, rAPOBEC1 expresses poorly in *E. coli* and localizes almost exclusively to the insoluble fraction (FIG. 2A). SP encoding rAPOBEC1 were evolved using SE-PACE for a total of 370 h (260 average generations) using three protein expression accessory plasmids (APs) of increasing stringency (FIG. 3A). Consensus mutations from SP isolated in lagoons 1 and 2 of the first two SE-PACE experiments are shown in FIG. 2B. Mutations in rAPOBEC1 after 370 hours of SE-PACE are shown in FIG. 2C. After the first 74 h, SPs containing the two dominant genotypes were pooled and this mixture was used to infect two parallel, identically-run lagoons. At 186 h, both lagoons converged on mutations (F113C+A123E+F205S) that yielded the 36.1 genotype (FIG. 3B); however, lagoon 1 had also collected an inactivating mutation (E63A). The final 184 h of PACE produced two variants (43.1 and 43.2) that enhanced expression >4-fold (FIG. 3B and FIG. 2A). As 43.2 was identified from lagoon 1, it also carried the E63A mutation, which was reverted to obtain 43.2-rev (FIG. 3B). When tested in a rifampicin resistance assay, neither 36.1 nor 43.1 showed defects in apparent deaminase activity. Evolved APOBEC clone 43.2-rev also showed comparable activity to wild-type rAPOBEC1, while 43.2 was completely inactive (FIG. 4A). Clones 36.1, 43.1, and 43.2-rev were all observed to have a negative impact on cell growth rate when expressed, while wild-type rAPOBEC1 and 43.2 exhibited no such effect, indicating that the observed growth inhibition may be due to increased expression of active deaminase (FIG. 4B).

Figure 3D:
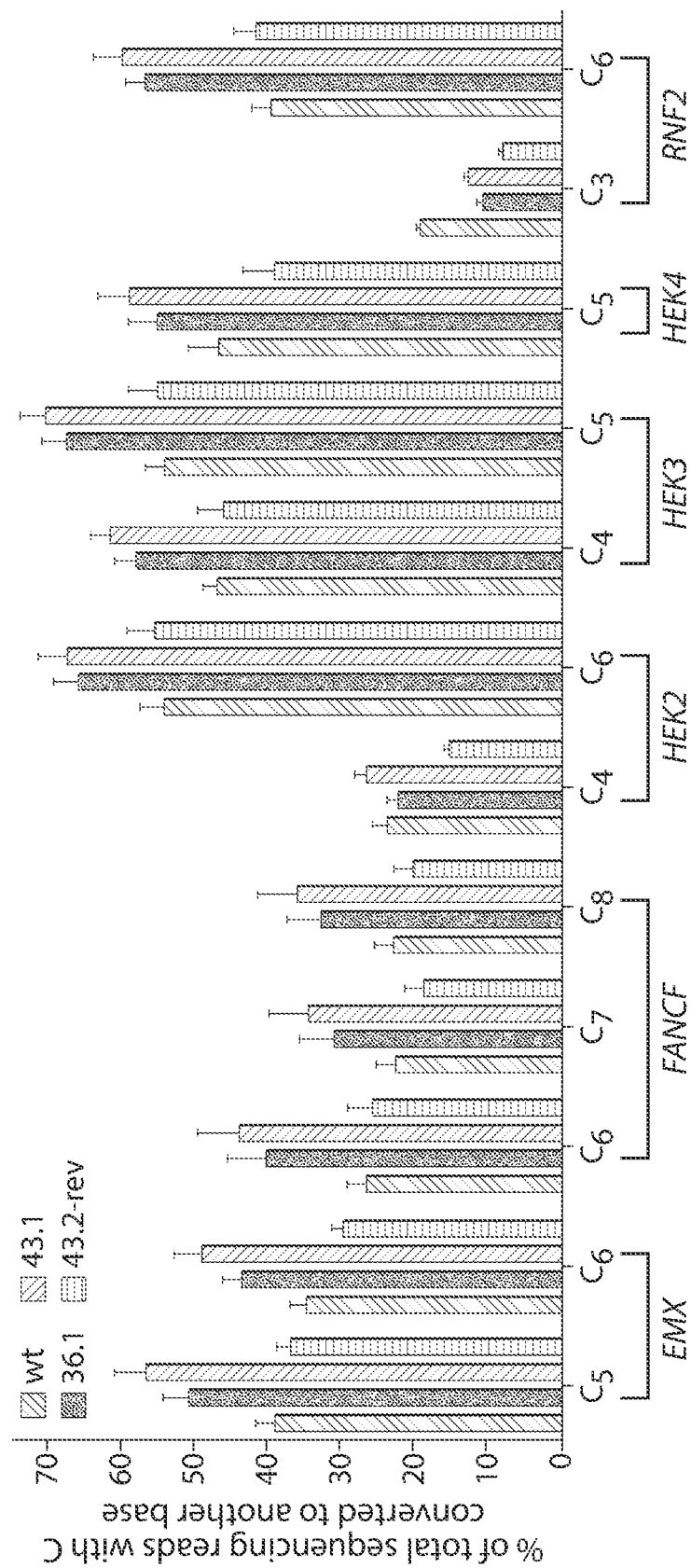
Figure 5:
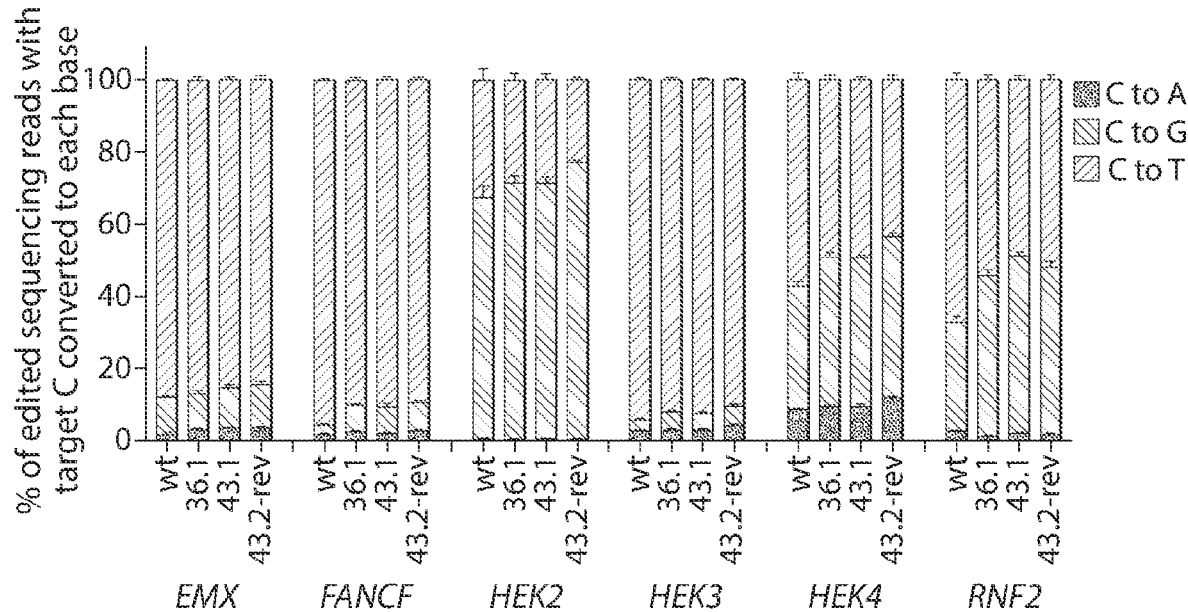
FIG. 5 shows product purity of BE3 mediated cytidine editing in HEK293T cells using wild-type rAPOBEC1 and evolved variants. The top panel refers to editing at the bolded C at each site. The bottom panel shows indel formation resulting from editing with BE3 variants in HEK293T cells at the same sites shown in the top panel. Sequences correspond from top to bottom to SEQ ID NOs: 43-48.
Figure 5:
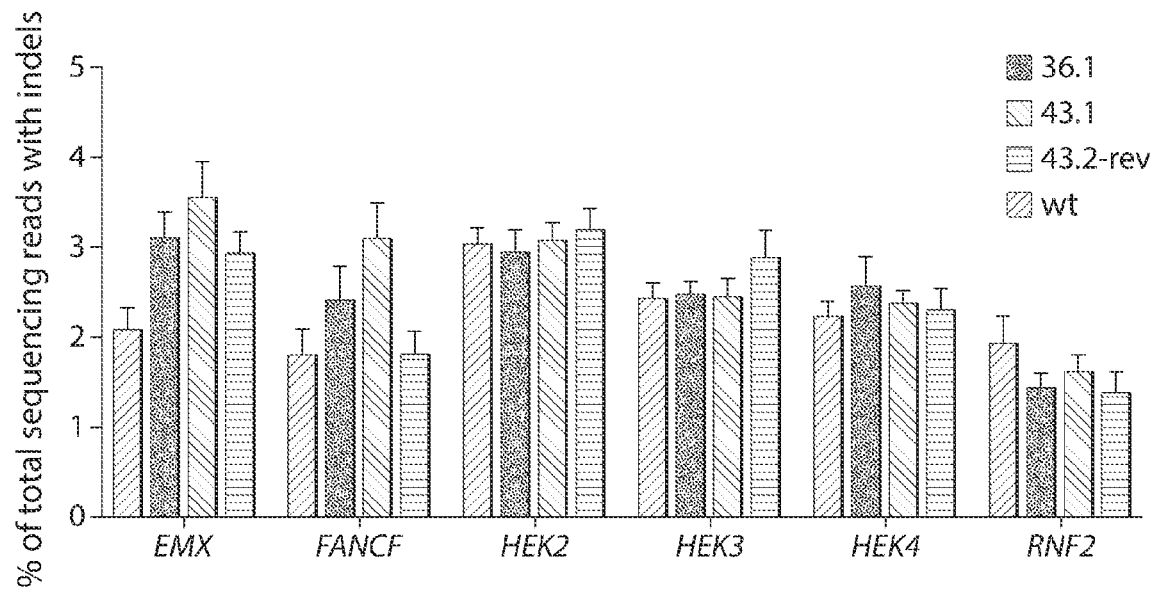

The SE-PACE-evolved APOBEC1 variants were also observed to have increased soluble expression levels in *E. coli* when incorporated into "base editors", engineered genome editing proteins consisting of a fusion of rAPOBEC1, a catalytically impaired Cas9, and a uracil glycosylase inhibitor (ugi) that enable targeted conversion of individual DNA base pairs in living cells. Substitution of wild-type rAPOBEC1 with 36.1, 43.1, and 43.2-rev in the base editor BE3 improved soluble expression yields by 2-3 fold (Table 1), despite the fact that rAPOBEC1 only accounts for ~15% of the total BE3 protein by molecular weight. Base editors incorporating evolved APOBEC variants 36.1, 43.1, and 43.2-rev also exhibited higher apparent editing activity in *E. coli*, as measured by the ability of BE2 (which contains dCas9 in place of Cas9 nickase) to rescue an active site mutation (H193R) in chloramphenicol acetyl transferase (FIG. 3C). Increased cytidine deamination was also observed in HEK293T cells transfected with BE3 variants 36.1 and 43.1 (FIG. 3D), albeit with modestly decreased product purities (FIG. 5). Together, these data indicate that SE-PACE improves base editor expression in *E. coli*.

TABLE 1

Yields of purified BE3 variants

| protein | Yield (mg)[a] | |
|---|---|---|
|  | Replicate 1 | Replicate 2 |
| BE3 (wt) | 0.25 | 0.21 |
| 36.1-BE3 | 0.45 | 0.33 |
| 43.1-BE3 | 0.71 | 0.54 |
| 43.2-rev-BE3 | 0.56 | 0.39 |

[a] Yield isolated from 200 mL culture in 2xYT at 16° C.

TABLE 2

Plasmids used in the Example

| Name | Class (res) | Origin | ORF1 Prom | [RBS][1] Genes | ORF2 Prom | [RBS] Genes | ORF3 Prom | [RBS] Genes |
|---|---|---|---|---|---|---|---|---|
| pTW006a | AP (carb^R) | SC101 | $P_{T7}$ | [SD8] luxAB | $P_{BAD}$ | [SD8] T7c | $P_c$ | araC |
| pTW006a2 | AP (carb^R) | SC101 | $P_{T7}$ | [SD8] luxAB | $P_{BAD}$ | [SD8] T7c R632S | $P_c$ | araC |
| pTW006a3 | AP (carb^R) | SC101 | $P_{T7}$ | [SD8] luxAB | $P_{BAD}$ | [SD8] T7c L637A | $P_c$ | araC |
| pTW006a4 | AP (carb^R) | SC101 | $P_{T7}$ | [SD8] luxAB | $P_{BAD}$ | [SD8] T7c Y639F | $P_c$ | araC |
| pTW006a5 | AP (carb^R) | SC101 | $P_{T7}$ | [SD8] luxAB | $P_{BAD}$ | [SD8] T7c Q649S | $P_c$ | araC |
| pTW006a6 | AP (carb^R) | SC101 | $P_{T7}$ | [SD8] luxAB | $P_{BAD}$ | [SD8] T7c F644A | $P_c$ | araC |
| pTW006aP1a | AP (carb^R) | SC101 | $P_{T7}$ | [SD8] gIII, luxAB | $P_{pro1}$ | [SD8] T7c |  |  |
| pJC175e | AP (carb^R) | SC101 | $P_{psp}$ | [SD8] gIII, luxAB |  |  |  |  |
| pTW026a3c | AP (carb^R) | SC101 | $P_{psp}$ | [SD8] gIII-N |  |  |  |  |
| pTW048a3 | AP (carb^R) | SC101 | $P_{lacZ\text{-}opt}$ (OR1 + 2) | [sd5] gIII-N | $P_{pro1}$[2] | 434cI – SH2$_{ABL1}$ |  |  |
| pTW055a3 | AP (carb^R) | SC101 | $P_{lacZ\text{-}opt}$ (OR1 + 2) | [sd8] gIII-N | $P_{pro1}$ | 434cI – GCN4 7P14P |  |  |
| pTW074c | AP (carb^R) | SC101 | $P_{lacZ\text{-}opt}$ (OR1) | [sd5] gIII-N | $P_{pro1}$ | 434cI – htt 1-17 |  |  |
| pTW084b | AP (carb^R) | SC101 | $P_{lacZ\text{-}opt}$ (OR1 + 2) | [sd5] gIII-N | $P_{pro1}$ | 434cI – m3 |  |  |
| pTW032b2c | AP (spec^R) | ColE1 | $P_{psp}$ | [sd5] gIII-C |  |  |  |  |
| pTW051a | AP (spec^R) | ColE1 | $P_{T7}$ | [sd5] gIII-C | $P_{pro1}$ | T7c |  |  |
| pTW051b2 | AP (spec^R) | ColE1 | $P_{T7a}$ | [sd5] gIII-C | $P_{pro1}$ | T7c R632S |  |  |
| pTW051b4 | AP (spec^R) | ColE1 | $P_{T7d}$ | [sd5] gIII-C | $P_{pro1}$ | T7c R632S |  |  |
| pTW051d | AP (spec^R) | ColE1 | $P_{T7a}$ | [sd5] gIII-C | $P_{pro1}$ | T7c R632S + Q649S |  |  |
| pTW051d2 | AP (spec^R) | ColE1 | $P_{T7d}$ | [sd5] gIII-C | $P_{pro1}$ | T7c R632S + Q649S |  |  |
| pTW004a | CP (spec^R) | ColE1 | $P_{tet}$ | [SD8] MBP – T7n |  |  |  |  |
| pTW004b | CP (spec^R) | ColE1 | $P_{tet}$ | [SD8] MBP G32D + I33P – T7n |  |  |  |  |
| pTW004d | CP (spec^R) | ColE1 | $P_{tet}$ | [SD8] MBP V8G – T7n |  |  |  |  |
| pTW004e | CP (spec^R) | ColE1 | $P_{tet}$ | [SD8] MBP G19C – T7n |  |  |  |  |
| pTW004f | CP (spec^R) | ColE1 | $P_{tet}$ | [SD8] MBP A276G – T7n |  |  |  |  |
| pTW004g | CP (spec^R) | ColE1 | $P_{tet}$ | [SD8] MBP Y283D – T7n |  |  |  |  |
| pTW004h | CP (spec^R) | ColE1 | $P_{tet}$ | [SD8] MBP T345I – T7n |  |  |  |  |
| pTW035d | EP (kan^R) | pBR322 | $P_{T7lac}$ | 6xHis – MBP G32D + I33P |  |  |  |  |
| pTW035e | EP (kan^R) | pBR322 | $P_{T7lac}$ | 6xHis – MBP |  |  |  |  |

TABLE 2-continued

Plasmids used in the Example

| Name | Class (res) | Origin | ORF1 Prom | [RBS]¹ Genes | ORF2 Prom | [RBS] Genes | ORF3 Prom | [RBS] Genes |
|---|---|---|---|---|---|---|---|---|
| pTW035g | EP (kan^R) | pBR322 | $P_{T7lac}$ | 6xHis – MBP V8G | | | | |
| pTW035h | EP (kan^R) | pBR322 | $P_{T7lac}$ | 6xHis – MBP G19C | | | | |
| pTW035i | EP (kan^R) | pBR322 | $P_{T7lac}$ | 6xHis – MBP A276G | | | | |
| pTW035j | EP (kan^R) | pBR322 | $P_{T7lac}$ | 6xHis – MBP Y283D | | | | |
| pTW035b | EP (kan^R) | pBR322 | $P_{T7lac}$ | 6xHis – MBP P33T + T275I | | | | |
| pTW035c | EP (kan^R) | pBR322 | $P_{T7lac}$ | 6xHis – MBP P33T + V76I + A167V + V373I | | | | |
| pTW035aa | EP (kan^R) | pBR322 | $P_{T7lac}$ | 6xHis – MBP D33T + F258Y | | | | |
| pTW035ab | EP (kan^R) | pBR322 | $P_{T7lac}$ | 6xHis – MBP D33L | | | | |
| pTW035ac | EP (kan^R) | pBR322 | $P_{T7lac}$ | 6xHis – MBP G24V + D33S | | | | |
| pTW069a | EP (kan^R) | pBR322 | $P_{T7lac}$ | 6xHis – Ωg | | | | |
| pTW069h | EP (kan^R) | pBR322 | $P_{T7lac}$ | 6xHis – m3 | | | | |
| pTW075I | EP (kan^R) | pBR322 | $P_{T7lac}$ | 6xHis – 29.1.2 | | | | |
| pTW075k | EP (kan^R) | pBR322 | $P_{T7lac}$ | 6xHis – 29.1.5 | | | | |
| pTW087a | EP (kan^R) | pBR322 | $P_{T7lac}$ | 6xHis – MBP – TEV – GCN4 7P14P | | | | |
| pTW081a | EP (kan^R) | pBR322 | $P_{T7lac}$ | 6xHis – C4 | | | | |
| pTW081d | EP (kan^R) | pBR322 | $P_{T7lac}$ | 6xHis – C4 V38F | | | | |
| pTW081e | EP (kan^R) | pBR322 | $P_{T7lac}$ | 6xHis – C4 A98V | | | | |
| pTW081i | EP (kan^R) | pBR322 | $P_{T7lac}$ | 6xHis – 34.1.2 | | | | |
| pTW081j | EP (kan^R) | pBR322 | $P_{T7lac}$ | 6xHis – 34.2.3 | | | | |
| pTW081k | EP (kan^R) | pBR322 | $P_{T7lac}$ | 6xHis – 34.2.6 | | | | |
| pTW101a | EP (spec^R) | ColE1 | $rhaP_{BAD}$ | 6xHis – rAPOBEC1 | $rhaP_{RS}$ | rhaS, rhaR | | |
| pTW101h | EP (spec^R) | ColE1 | $rhaP_{BAD}$ | 6xHis – 36.1 | $rhaP_{RS}$ | rhaS, rhaR | | |
| pTW101t | EP (spec^R) | ColE1 | $rhaP_{BAD}$ | 6xHis – 43.1 | $rhaP_{RS}$ | rhaS, rhaR | | |
| pTW101m | EP (spec^R) | ColE1 | $rhaP_{BAD}$ | 6xHis – 43.2 | $rhaP_{RS}$ | rhaS, rhaR | | |
| pTW101m2 | EP (spec^R) | ColE1 | $rhaP_{BAD}$ | 6xHis – 43.2-rev | $rhaP_{RS}$ | rhaS, rhaR | | |
| pHR41[13] | EP (kan^R) | pBR322 | $P_{T7lac}$ | 6xHis – BE3 | | | | |
| pTW142a | EP (kan^R) | pBR322 | $P_{T7lac}$ | 6xHis – 36.1-BE3 | | | | |
| pTW142b | EP (kan^R) | pBR322 | $P_{T7lac}$ | 6xHis – 43.1-BE3 | | | | |
| pTW142c | EP (kan^R) | pBR322 | $P_{T7lac}$ | 6xHis – 43.2-rev-BE3 | | | | |
| pNMG98[14] | EP (carb^R) | SC101 | $P_{lac}$ | gRNA | $P_{BAD}$ | BE2 | $P_c$ | araC |
| pTW143a | EP (carb^R) | SC101 | $P_{lac}$ | gRNA | $P_{BAD}$ | 36.1-BE2 | $P_c$ | araC |
| pTW143b | EP (carb^R) | SC101 | $P_{lac}$ | gRNA | $P_{BAD}$ | 43.1-BE2 | $P_c$ | araC |
| pTW143c | EP (carb^R) | SC101 | $P_{lac}$ | gRNA | $P_{BAD}$ | 43.2-rev-BE2 | $P_c$ | araC |
| pTW143d | EP (carb^R) | SC101 | $P_{lac}$ | gRNA | $P_{BAD}$ | 43.2-BE2 | $P_c$ | araC |

TABLE 2-continued

Plasmids used in the Example

| Name | Class (res) | Origin | ORF1 Prom | [RBS]¹ Genes | ORF2 Prom | [RBS] Genes | ORF3 Prom | [RBS] Genes |
|---|---|---|---|---|---|---|---|---|
| antibiotic selection uracil[14] | spec$^R$ | RSF1030 | $P_{kan}$ | kan$^R$ | $P_{cat}$ | cam$^R$ H193R | | |
| PACK129[15] | carb$^R$ | pBR322 | $P_{CMV}$ | BE3 | | | | |
| pTW107a | carb$^R$ | pBR322 | $P_{CMV}$ | 36.1 BE3 | | | | |
| pTW107b | carb$^R$ | pBR322 | $P_{CMV}$ | 43.1 BE3 | | | | |
| pTW107c | carb$^R$ | pBR322 | $P_{CMV}$ | 43.2-rev BE3 | | | | |
| MP6 | MP (chlor$^R$) | cloDF13 | $P_{BAD}$ | dnaQ926, dam, seqA, emrR, ugi, cda1 | $P_c$ | araC | | |
| DP6 | MP (chlor$^R$) | cloDF13 | $P_{BAD}$ | dnaQ926, dam, seqA, emrR, ugi, cda1 | $P_c$ | araC | $P_{psp\text{-}tet}$ | [sd8] gIII |
| SP01a | SP (none) | M13 fl | $P_{gIII}$ | MBP – T7n | | | | |
| SP01z | SP (none) | M13 fl | $P_{gIII}$ | T7n | | | | |
| SP02a | SP (none) | M13 fl | $P_{gIII}$ | MBP G32D + I33P – T7n | | | | |
| SP02b | SP (none) | M13 fl | $P_{gIII}$ | MBP Y283D – T7n | | | | |
| SP09b3 | SP (none) | M13 fl | $P_{gIII}$ | HA4 – T7n – rpoZ | | | | |
| SP10b2 | SP (none) | M13 fl | $P_{gIII}$ | HA4 Y87A – T7n – rpoZ | | | | |
| SP16c3 | SP (none) | M13 fl | $P_{gIII}$ | Ωg – eT7n – rpoZ | | | | |
| SP24a3 | SP (none) | M13 fl | $P_{gIII}$ | C4 – eT7n – rpoZ | | | | |
| SP27b | SP (none) | M13 fl | $P_{gIII}$ | GCN4 7P14P – MBP G32D + I33P – eT7n – rpoZ | | | | |
| SP30 | SP (none) | M13 fl | $P_{gIII}$ | GCN4 7P14P – rAPOBEC1 – eT7n – rpoZ | | | | |
| SP39b | SP (none) | M13 fl | $P_{gIII}$ | m3-noCys – eT7n – rpoZ | | | | |
| SP39d | SP (none) | M13 fl | $P_{gIII}$ | 29.1.5-noCys – eT7n – rpoZ | | | | |
| SP13 | SP (none) | M13 fl | $P_{gIII}$ | kan | | | | |
| SP98 | SP (none) | M13 fl | $P_{gIII}$ | rpoZ – HA4 | | | | |

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

>SEQ ID NO: 1; gIII-N (NpuN is shown in bold.)
ATGAAAAAATTATTATTCGCAATTCCTTTATGTCTCAGCTACGAAACCGA

AATCTTGACCGTCGAATATGGTCTGCTGCCAATCGGCAAGATTGTTGAAA

AACGTATTGAATGTACGGTCTACTCAGTGGATAACAACGGCAATATCTAC

ACCCAGCCGGTGGCCCAGTGGCATGACCGTGGTGAACAGGAAGTGTTCGA

ATATTGTCTGGAAGACGGATCTTTAATCCGTGCCACAAAGGATCACAAAT

TTATGACTGTAGATGGTCAGATGCTCCCAATCGACGAAATTTTTGAACGC

GAATTAGACCTGATGCGCGTGGATAATCTCCCGAATTAA

>SEQ ID NO: 2; gIII-C (NpuC is highlighted in bold. The +1, +2, and +3 exteins are underlined.)
ATGATCAAAATTGCCACGCGTAAATATTTAGGCAAACAGAATGTTTATGA

TATCGGTGTCGAGCGCGATCATAATTTCGCGCTGAAAAACGGCTTTATCG

CCAGCAAT<u>TGTTTTAAT</u>GTTGTTCCTTTCTATTCTCACTCCGCTGAAACT

GTTGAAAGTTGTTTAGCAAAACCCCATACAGAAAATTCATTTACTAACGT

CTGGAAAGACGACAAAACTTTAGATCGTTACGCTAACTATGAGGGCTGTC

TGTGGAATGCTACAGGCGTTGTAGTTTGTACTGGTGACGAAACTCAGTGT

TACGGTACATGGGTTCCTATTGGGCTTGCTATCCCTGAAAATGAGGGTGG

TGGCTCTGAGGGTGGCGGTTCTGAGGGTGGCGGTTCTGAGGGTGGCGGTA

CTAAACCTCCTGAGTACGGTGATACACCTATTCCGGGCTATACTTATATC

AACCCTCTCGACGGCACTTATCCGCCTGGTACTGAGCAAAACCCCGCTAA

TCCTAATCCTTCTCTTGAGGAGTCTCAGCCTCTTAATACTTTCATGTTTC

AGAATAATAGGTTCCGAAATAGGCAGGGGGCATTAACTGTTTATACGGGC

ACTGTTACTCAAGGCACTGACCCCGTTAAAACTTATTACCAGTACACTCC

TGTATCATCAAAAGCCATGTATGACGCTTACTGGAACGGTAAATTCAGAG

ACTGCGCTTTCCATTCTGGCTTTAATGAGGATCCATTCGTTTGTGAATAT

CAAGGCCAATCGTCTGACCTGCCTCAACCTCCTGTCAATGCTGGCGGCGG

CTCTGGTGGTGGTTCTGGTGGCGGCTCTGAGGGTGGTGGCTCTGAGGGTG

GCGGTTCTGAGGGTGGCGGCTCTGAGGGAGGCGGTTCCGGTGGTGGCTCT

GGTTCCGGTGATTTTGATTATGAAAGATGGCAAACGCTAATAAGGGGGC

TATGACCGAAAATGCCGATGAAAACGCGCTACAGTCTGACGCTAAAGGCA

AACTTGATTCTGTCGCTACTGATTACGGTGCTGCTATCGATGGTTTCATT

GGTGACGTTTCCGGCCTTGCTAATGGTAATGGTGCTACTGGTGATTTTGC

TGGCTCTAATTCCCAAATGGCTCAAGTCGGTGACGGTGATAATTCACCTT

TAATGAATAATTTCCGTCAATATTTACCTTCCCTCCCTCAATCGGTTGAA

TGTCGCCCTTTTGTCTTTGGCGCTGGTAAACCTTACGAGTTCAGTATCGA

CTGCGATAAGATCAACCTGTTCCGCGGTGTCTTTGCGTTTCTTTTATATG

TTGCCACCTTTATGTATGTATTTTCTACGTTTGCTAACATACTGCGTAAT

AAGGAGTCTTAA

>SEQ ID NO: 3; T7n
AACACGATTAACATCGCTAAGAACGACTTCTCTGACATCGAACTGGCTGC

TATCCCGTTCAACACTCTGGCTGACCATTACGGTGAGCGTTTAGCTCGCG

AACAGTTGGCCCTTGAGCATGAGTCTTACGAGATGGGTGAAGCACGCTTC

CGCAAGATGTTTGAGCGTCAACTTAAAGCTGGTGAGGTTGCGGATAACGC

TGCCGCCAAGCCTCTCATCACTACCCTACTCCCTAAGATGATTGCACGCA

TCAACGACTGGTTTGAGGAAGTGAAAGCTAAGCGCGGCAAGCGCCCGACA

GCCTTCCAGTTCCTGCAAGAAATCAAGCCGGAAGCCGTAGCGTACATCAC

CATTAAGACCACTCTGGCTTGCCTAACCAGTGCTGACAATACAACCGTTC

AGGCTGTAGCAAGCGCAATCGGTCGGGCCATTGAGGACGAGGCTCGCTTC

GGTCGTATCCGTGACCTTGAAGCTAAGCACTTCAAGAAAAACGTTGAGGA

ACAACTCAACAAGCGCGTAGGGCACGTCTACAAG

>SEQ ID NO: 4; eT7n (Nucleotides in bold represent mutations relative to T7n, SEQ ID NO: 3)
AACACCATTAATATCGCTAAGAACGGCTTCTCTGATATCGAACTGGCTGC

TATCCCGTTCAACACTCTGGCTGACCATTACGGTGAGCGTTTAGCTCGCG

AACAGTTGGCCCTTGAGCATGAGTCTTACGAGATGGATGAAGCACGCTTC

CGCAAGATGTTTGAGCGTCAACTTAAAGCTGGTGAGGTTGCGGATAACAC

TGCCGCCAATCCTCTCATCACTACCCTACTCCTTAAGATGATTGCACGCA

TCAAGGACTGGTTTGAGGAAGTGAAAGCTAAGCGCGGCAAGCGCCCGACA

GCCTTCCATTTCCTGAAAGAAATCAAGCCGGAAGCCGTAGCGTACATCAC

CATTAAGGCCACTCTGGCTTGCCTAACCAGTGCTAACAAAACAACCGTTC

AGGCTGTAGCAAGCGCAATCGGTCGGGCCATTGAGGACGAGGCTCGCTTC

GGTCGTATCCGTTACCTTGAAGCTAAGCACTTCAAGAAAAACGTTGAGGA

ACAACTCAACAAGCGCGTAGGGCACGTCCACAAG

>SEQ ID NO: 5; GCN4 7P14P peptide
TTGCAAAGAATGAAACAACTTGAACCGAAGGTTGAAGAATTGCTTCCGAA

AAATTATCACTTGGAAAATGAGGTTGCCAGATTAAAGAAATTAGTTGGCG

AACGC

>SEQ ID NO: 6; Wild-type rAPOBEC1 Nucleic Acid
Sequence
TCTTCTGAAACCGGTCCGGTTGCGGTTGACCCGACCCTGCGTCGTCGTAT

CGAACCGCACGAATTCGAAGTTTTCTTCGACCCGCGTGAACTGCGTAAAG

AAACCTGCCTGCTGTACGAAATCAACTGGGGTGGTCGTCACTCTATCTGG

CGTCACACCTCTCAGAACACCAACAAACACGTTGAAGTTAACTTCATCGA

AAAATTCACCACCGAACGTTACTTCTGCCCGAACACCCGTTGCTCTATCA

CCTGGTTCCTGTCTTGGTCTCCGTGCGGTGAATGCTCTCGTGCGATCACC

GAATTCCTGTCTCGTTACCCGCACGTTACCCTGTTCATCTACATCGCGCG

TCTGTACCACCACGCGGACCCGCGTAACCGTCAGGGTCTGCGTGACCTGA

TCTCTTCTGGTGTTACCATCCAGATCATGACCGAACAGGAATCTGGTTAC

TGCTGGCGTAACTTCGTTAACTACTCTCCGTCTAACGAAGCGCACTGGCC

GCGTTACCCGCACCTGTGGGTTCGTCTGTACGTTCTGGAACTGTACTGCA

TCATCCTGGGTCTGCCGCCGTGCCTGAACATCCTGCGTCGTAAACAGCCG

CAGCTGACCTTCTTCACCATCGCGCTGCAGTCTTGCCACTACCAGCGTCT

GCCGCCGCACATCCTGTGGGCGACCGGTCTGAAA

>SEQ ID NO: 7; rAPOBEC variant 36.1
(Nucleotides in bold represent mutations relative
to wild-type rAPOBEC1, SEQ ID NO: 6)
TCTTCTGAAACCGGTCCGGTTGCGGTTGACCCGACCCTGCGTCGTCGTAT

CGAACCGCACGAATTCGAAGTTTTCTTCGACCCGCGTGAACTGCGTAAAG

AAACCTGCCTGCTGTACGAAATCAACTGGGGTGGTCGTCACTCTATCTGG

CGTCACACCTCTCAGAACACCAACAAACACGTTGAAGTTAACTTCATCGA

AAAATTCACCACCGAACGTTACTTCTGCCCGAACACCCGTTGCTCTATCA

CCTGGTTCCTGTCTTGGTCTCCGTGCGGTGAATGCTCTCGTGCGATCACC

GAATTCCTGTCTCGTTACCCGCACGTTACCCTGTGCATCTACATCGCGCG

TCTGTACCACCACGAGGACCCGCGTAACCGTCAGGGTCTGCGTGACCTGA

TCTCTTCTGGTGTTACCATCCAGATCATGACCGAACAGGAATCTGGTTAC

TGCTGGCGTAACTTCGTTAACTACTCTCCGTCTAACGAAGCGCACTGGCC

GCGTTACCCGCACCTGTGGGTTCGTCTGTACGTTCTGGAACTGTACTGCA

TCATCCTGGGTCTGCCGCCGTGCCTGAACATCCTGCGTCGTAAACAGCCG

CAGCTGACCTCCTTCACCATCGCGCTGCAGTCTTGCCACTACCAGCGTCT

GCCGCCGCACATCCTGTGGGCGACCGGTCTGAA
A

>SEQ ID NO: 8; rAPOBEC variant 43.1
(Nucleotides in bold represent mutations relative
to wild-type rAPOBEC1, SEQ ID NO: 6)
TCTTCTGAAACCGGTCCGGTTGCGGTTGACCCGACCCTGCGTCGTCGTAT

CGAACCGCACGAATTCGAAGTTTTCTTCGACCCGCGTGAACTGCGTAAAG

AAACCTGCCTGCTGTACGAAATCAACTGGGATGGTCGTCACTCTATCTGG

CGTCACACCTCTCAGAACACCAACAAACACGTTGAAGTTAACTTCATCGA

AAAATTCACCACCGAACGTCACTTCTGCCCTAACACCCGTTGCTCTATCA

CCTGGTTCCTGTCTTGGTCTCCGTGCGGTGAATGCTCTCGTGCGATCACC

GAATTCCTGTCTCGTTACCCGCACGTTACCCTGTGCATCTACATCGCGCG

TCTGTACCACCACGAGGACCCGCGTAACCGTCAGGGTCTGCGTGACCTGA

TCTCTTCTGGTGTTACCATCCAGATCATGACCGAACAGGAATCTGGTTAC

TGCTGGCGTAACTTCGTTAACTACTCTCCGTCTAACGAAGCGAACTGGCC

GCGTTACCCGCACCTGTGGGTTCGTCTGTACGTTCTGGAACTGTACTGCA

TCATCCTGGGTCTGCCGCCGTGCCTGAACATCCTGCGTCGTAAACAGCCG

CAGCTGACCTCCTTCACCATCGCGCTGCAGTCTTGCCACTACCAGCGTCT

GCCGCCGCACATCCTGTGGGCGCCCGGTCTGAAA

>SEQ ID NO: 9; rAPOBEC variant 43.2 (Nucleotides
in bold represent mutations relative to wild-type
rAPOBEC1, SEQ ID NO: 6; the nucleotide that is
bold underlined was reverted to an A in 43.2-rev)
TCTTCTGAAACCGGTCCGGTTGCGGTTGACCCGACCCTGCGTCGTCGTAT

CGAACCGCACGAATTCGAAGTTTTCTTCGACCCGCGTGAACTGCGTAAAG

AAACCTGTCTGCTGTACGAAATCAACTGGGGTGGTCGTCACTCTATCTGG

CGTCACACCTCTCAGAACACCAACAAACACGTTGCAGTTAACTTCATCGA

AAAATTCACCACCGAACGTTACTTCTGCCCGAACACCCGTTGCTCTATCA

CCTGGTTCCTGTCTTGGTCTCCGTGCGGTGAATGCTCTCGTGCGATCACC

GAATTCCTGTCTCGTTACCCGCACGTTACCCTGTGCATCTACATCGCGCG

TCTGTACCACCACGAGGACCCGCGTAACCGTCAGGGTCTGCGTGACCTGA

TCTCTTCTGGTGTTACCATCCAGATCATGACCGAACAGGAATCTGGTTAC

TGCTGGCGTAACTTCGTTAACTACTCTCCGTCTAACGAAACGCACTGGCC

GCGTTACCCGCACCTGTGGGTTCGTCTGTACGTTCTGGAACTGTACTGCA

TCATCCTGGGTCTGCCGCCGTGCCTGAACATCCTGCGTCGTAAACAGCCG

CAGCTGACCTCCTTCACCATCGCGCTGCAGTCTTGCCACTACCAGCGTCT

GCCGCCGCACATCCTGTGGGCGACCGGTCTGAAA

>SEQ ID NO: 10; rAPOBEC variant 43.2-rev
(Nucleotides in bold represent mutations relative
to wild-type rAPOBEC1, SEQ ID NO: 6; the
nucleotide that is bold underlined was reverted
from a C in 43.2)
TCTTCTGAAACCGGTCCGGTTGCGGTTGACCCGACCCTGCGTCGTCGTAT

CGAACCGCACGAATTCGAAGTTTTCTTCGACCCGCGTGAACTGCGTAAAG

AAACCTGTCTGCTGTACGAAATCAACTGGGGTGGTCGTCACTCTATCTGG

CGTCACACCTCTCAGAACACCAACAAACACGTTGAAGTTAACTTCATCGA

AAAATTCACCACCGAACGTTACTTCTGCCCGAACACCCGTTGCTCTATCA

CCTGGTTCCTGTCTTGGTCTCCGTGCGGTGAATGCTCTCGTGCGATCACC

GAATTCCTGTCTCGTTACCCGCACGTTACCCTGTGCATCTACATCGCGCG

TCTGTACCACCACGAGGACCCGCGTAACCGTCAGGGTCTGCGTGACCTGA

TCTCTTCTGGTGTTACCATCCAGATCATGACCGAACAGGAATCTGGTTAC

TGCTGGCGTAACTTCGTTAACTACTCTCCGTCTAACGAAACGCACTGGCC

GCGTTACCCGCACCTGTGGGTTCGTCTGTACGTTCTGGAACTGTACTGCA

TCATCCTGGGTCTGCCGCCGTGCCTGAACATCCTGCGTCGTAAACAGCCG

CAGCTGACCTCCTTCACCATCGCGCTGCAGTCTTGCCACTACCAGCGTCT

GCCGCCGCACATCCTGTGGGCGACCGGTCTGAAA

>SEQ ID NO: 11; wild-type rAPOBEC mammalian codon
optimized sequence
AGCTCAGAGACTGGCCCAGTGGCTGTGGACCCCACATTGAGACGGCGGAT

CGAGCCCCATGAGTTTGAGGTATTCTTCGATCCGAGAGAGCTCCGCAAGG

AGACCTGCCTGCTTTACGAAATTAATTGGGGGGGCCGGCACTCCATTTGG

CGACATACATCACAGAACACTAACAAGCACGTCGAAGTCAACTTCATCGA

GAAGTTCACGACAGAAAGATATTTCTGTCCGAACACAAGGTGCAGCATTA

CCTGGTTTCTCAGCTGGAGCCCATGCGGCGAATGTAGTAGGGCCATCACT

GAATTCCTGTCAAGGTATCCCCACGTCACTCTGTTTATTTACATCGCAAG

GCTGTACCACCACGCTGACCCCCGCAATCGACAAGGCCTGCGGGATTTGA

TCTCTTCAGGTGTGACTATCCAAATTATGACTGAGCAGGAGTCAGGATAC

TGCTGGAGAAACTTTGTGAATTATAGCCCGAGTAATGAAGCCCACTGGCC

TAGGTATCCCCATCTGTGGGTACGACTGTACGTTCTTGAACTGTACTGCA

TCATACTGGGCCTGCCTCCTTGTCTCAACATTCTGAGAAGGAAGCAGCCA

CAGCTGACATTCTTTACCATCGCTCTTCAGTCTTGTCATTACCAGCGACT

GCCCCCACACATTCTCTGGGCCACCGGGTTGAAA

>SEQ ID NO: 12; rAPOBEC variant 36.1 mammalian
codon optimized sequence
AGCTCAGAGACTGGCCCAGTGGCTGTGGACCCCACATTGAGACGGCGGAT

CGAGCCCCATGAGTTTGAGGTATTCTTCGATCCGAGAGAGCTCCGCAAGG

AGACCTGCCTGCTTTACGAAATTAATTGGGGGGGCCGGCACTCCATTTGG

CGACATACATCACAGAACACTAACAAGCACGTCGAAGTCAACTTCATCGA

GAAGTTCACGACAGAAAGATATTTCTGTCCGAACACAAGGTGCAGCATTA

CCTGGTTTCTCAGCTGGAGCCCATGCGGCGAATGTAGTAGGGCCATCACT

GAATTCCTGTCAAGGTATCCCCACGTCACTCTGTGTATTTACATCGCAAG

GCTGTACCACCACGAGACCCCCGCAATCGACAAGGCCTGCGGGATTTGA

TCTCTTCAGGTGTGACTATCCAAATTATGACTGAGCAGGAGTCAGGATAC

TGCTGGAGAAACTTTGTGAATTATAGCCCGAGTAATGAAGCCCACTGGCC

TAGGTATCCCCATCTGTGGGTACGACTGTACGTTCTTGAACTGTACTGCA

TCATACTGGGCCTGCCTCCTTGTCTCAACATTCTGAGAAGGAAGCAGCCA

CAGCTGACATCCTTTACCATCGCTCTTCAGTCTTGTCATTACCAGCGACT

GCCCCCACACATTCTCTGGGCCACCGGGTTGAAA

>SEQ ID NO: 13; rAPOBEC variant 43.1 mammalian
codon optimized sequence
AGCTCAGAGACTGGCCCAGTGGCTGTGGACCCCACATTGAGACGGCGGAT

CGAGCCCCATGAGTTTGAGGTATTCTTCGATCCGAGAGAGCTCCGCAAGG

AGACCTGCCTGCTTTACGAAATTAATTGGGATGGCCGGCACTCCATTTGG

CGACATACATCACAGAACACTAACAAGCACGTCGAAGTCAACTTCATCGA

GAAGTTCACGACAGAAAGACACTTCTGTCCGAACACAAGGTGCAGCATTA

CCTGGTTTCTCAGCTGGAGCCCATGCGGCGAATGTAGTAGGGCCATCACT

GAATTCCTGTCAAGGTATCCCCACGTCACTCTGTGTATTTACATCGCAAG

GCTGTACCACCACGAGACCCCCGCAATCGACAAGGCCTGCGGGATTTGA

TCTCTTCAGGTGTGACTATCCAAATTATGACTGAGCAGGAGTCAGGATAC

TGCTGGAGAAACTTTGTGAATTATAGCCCGAGTAATGAAGCCAACTGGCC

TAGGTATCCCCATCTGTGGGTACGACTGTACGTTCTTGAACTGTACTGCA

TCATACTGGGCCTGCCTCCTTGTCTCAACATTCTGAGAAGGAAGCAGCCA

CAGCTGACATCCTTTACCATCGCTCTTCAGTCTTGTCATTACCAGCGACT

GCCCCCACACATTCTCTGGGCCACCGGGTTGAAA

>SEQ ID NO: 14; rAPOBEC variant 43.2-rev
mammalian codon optimized sequence
AGCTCAGAGACTGGCCCAGTGGCTGTGGACCCCACATTGAGACGGCGGAT

CGAGCCCCATGAGTTTGAGGTATTCTTCGATCCGAGAGAGCTCCGCAAGG

AGACCTGCCTGCTTTACGAAATTAATTGGGGGGGCCGGCACTCCATTTGG

CGACATACATCACAGAACACTAACAAGCACGTCGAAGTCAACTTCATCGA

GAAGTTCACGACAGAAAGATATTTCTGTCCGAACACAAGGTGCAGCATTA

CCTGGTTTCTCAGCTGGAGCCCATGCGGCGAATGTAGTAGGGCCATCACT

GAATTCCTGTCAAGGTATCCCCACGTCACTCTGTGTATTTACATCGCAAG

GCTGTACCACCACGAGACCCCCGCAATCGACAAGGCCTGCGGGATTTGA

TCTCTTCAGGTGTGACTATCCAAATTATGACTGAGCAGGAGTCAGGATAC

TGCTGGAGAAACTTTGTGAATTATAGCCCGAGTAATGAAACCCACTGGCC

TAGGTATCCCCATCTGTGGGTACGACTGTACGTTCTTGAACTGTACTGCA

TCATACTGGGCCTGCCTCCTTGTCTCAACATTCTGAGAAGGAAGCAGCCA

CAGCTGACATCCTTTACCATCGCTCTTCAGTCTTGTCATTACCAGCGACT

GCCCCCACACATTCTCTGGGCCACCGGGTTGAAA

>SEQ ID NO: 15; Wild-type rAPOBEC1 Amino
Acid Sequence
MSSETGPVAVDPTLRRRIEPHEFEVFFDPRELRKETCLLYEINWGGRHSI
WRHTSQNTNKHVEVNFIEKFTTERYFCPNTRCSITWFLSWSPCGECSRAI
TEFLSRYPHVTLFIYIARLYHHADPRNRQGLRDLISSGVTIQIMTEQESG
YCWRNFVNYSPSNEAHWPRYPHLWVRLYVLELYCIILGLPPCLNILRRKQ
PQLTFFTIALQSCHYQRLPPHILWATGLK >SEQ ID NO: 16; rAPOBEC variant 36.1 Amino
Acid Sequence
MSSETGPVAVDPTLRRRIEPHEFEVFFDPRELRKETCLLYEINWGGRHSI
WRHTSQNTNKHVEVNFIEKFTTERYFCPNTRCSITWFLSWSPCGECSRAI
TEFLSRYPHVTLCIYIARLYHHEDPRNRQGLRDLISSGVTIQIMTEQESG
YCWRNFVNYSPSNEAHWPRYPHLWVRLYVLELYCIILGLPPCLNILRRKQ
PQLTSFTIALQSCHYQRLPPHILWATGLK >SEQ ID NO: 17; rAPOBEC variant 43.1 Amino
Acid Sequence
MSSETGPVAVDPTLRRRIEPHEFEVFFDPRELRKETCLLYEINWDGRHSI
WRHTSQNTNKHVEVNFIEKFTTERHFCPNTRCSITWFLSWSPCGECSRAI
TEFLSRYPHVTLCIYIARLYHHEDPRNRQGLRDLISSGVTIQIMTEQESG
YCWRNFVNYSPSNEANWPRYPHLWVRLYVLELYCIILGLPPCLNILRRKQ
PQLTSFTIALQSCHYQRLPPHILWAPGLK >SEQ ID NO: 18; rAPOBEC variant 43.2 Amino
Acid Sequence
MSSETGPVAVDPTLRRRIEPHEFEVFFDPRELRKETCLLYEINWGGRHSI
WRHTSQNTNKHVAVNFIEKFTTERYFCPNTRCSITWFLSWSPCGECSRAI
TEFLSRYPHVTLCIYIARLYHHEDPRNRQGLRDLISSGVTIQIMTEQESG
YCWRNFVNYSPSNETHWPRYPHLWVRLYVLELYCIILGLPPCLNILRRKQ
PQLTSFTIALQSCHYQRLPPHILWATGLK >SEQ ID NO: 19; rAPOBEC variant 43.2-rev
Amino Acid Sequence
MSSETGPVAVDPTLRRRIEPHEFEVFFDPRELRKETCLLYEINWGGRHSI
WRHTSQNTNKHVEVNFIEKFTTERYFCPNTRCSITWFLSWSPCGECSRAI
TEFLSRYPHVTLCIYIARLYHHEDPRNRQGLRDLISSGVTIQIMTEQESG
YCWRNFVNYSPSNETHWPRYPHLWVRLYVLELYCIILGLPPCLNILRRKQ
PQLTSFTIALQSCHYQRLPPHILWATGLK >SEQ ID NO: 20; wild-type Cas9 domain used
in BE3 and BE4
DKKYSIGLDIGTNSVGWAVITDEYKVPSKKFKVLGNTDRHSIKKNLIGAL
LFDSGETAEATRLKRTARRRYTRRKNRICYLQEIFSNEMAKVDDSFFHRL
EESFLVEEDKKHERHPIFGNIVDEVAYHEKYPTIYHLRKKLVDSTDKADL
RLIYLALAHMIKFRGHFLIEGDLNPDNSDVDKLFIQLVQTYNQLFEENPI
NASGVDAKAILSARLSKSRRLENLIAQLPGEKKNGLFGNLIALSLGLTPN
FKSNFDLAEDAKLQLSKDTYDDDLDNLLAQIGDQYADLFLAAKNLSDAIL
LSDILRVNTEITKAPLSASMIKRYDEHHQDLTLLKALVRQQLPEKYKEIF
FDQSKNGYAGYIDGGASQEEFYKFIKPILEKMDGTEELLVKLNREDLLRK
QRTFDNGSIPHQIHLGELHAILRRQEDFYPFLKDNREKIEKILTFRIPYY
VGPLARGNSRFAWMTRKSEETITPWNFEEVVDKGASAQSFIERMTNFDKN
LPNEKVLPKHSLLYEYFTVYNELTKVKYVTEGMRKPAFLSGEQKKAIVDL
LFKTNRKVTVKQLKEDYFKKIECFDSVEISGVEDRFNASLGTYHDLLKII
KDKDFLDNEENEDILEDIVLTLTLFEDREMIEERLKTYAHLFDDKVMKQL
KRRRYTGWGRLSRKLINGIRDKQSGKTILDFLKSDGFANRNFMQLIHDDS
LTFKEDIQKAQVSGQGDSLHEHIANLAGSPAIKKGILQTVKVVDELVKVM
GRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDS
IDNKVLTRSDKNRGKSDNVPSEEVVKKMKNYWRQLLNAKLITQRKFDNLT
KAERGGLSELDKAGFIKRQLVETRQITKHVAQILDSRMNTKYDENDKLIR
EVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEIT
LANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEK
GKSKKLKSVKELLGITIMERSSFEKNPIDFLEAKGYKEVKKDLIIKLPKY
SLFELENGRKRMLASAGELQKGNELALPSKYVNFLYLASHYEKLKGSPED
NEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQS
ITGLYETRIDLSQLGGD >SEQ ID NO: 21; Cas9 domain nickase used in
BE3 and BE4 base editors
DKKYSIGLAIGTNSVGWAVITDEYKVPSKKFKVLGNTDRHSIKKNLIGAL
LFDSGETAEATRLKRTARRRYTRRKNRICYLQEIFSNEMAKVDDSFFHRL
EESFLVEEDKKHERHPIFGNIVDEVAYHEKYPTIYHLRKKLVDSTDKADL
RLIYLALAHMIKFRGHFLIEGDLNPDNSDVDKLFIQLVQTYNQLFEENPI
NASGVDAKAILSARLSKSRRLENLIAQLPGEKKNGLFGNLIALSLGLTPN
FKSNFDLAEDAKLQLSKDTYDDDLDNLLAQIGDQYADLFLAAKNLSDAIL
LSDILRVNTEITKAPLSASMIKRYDEHHQDLTLLKALVRQQLPEKYKEIF
FDQSKNGYAGYIDGGASQEEFYKFIKPILEKMDGTEELLVKLNREDLLRK
QRTFDNGSIPHQIHLGELHAILRRQEDFYPFLKDNREKIEKILTFRIPYY
VGPLARGNSRFAWMTRKSEETITPWNFEEVVDKGASAQSFIERMTNFDKN
LPNEKVLPKHSLLYEYFTVYNELTKVKYVTEGMRKPAFLSGEQKKAIVDL
LFKTNRKVTVKQLKEDYFKKIECFDSVEISGVEDRFNASLGTYHDLLKII
KDKDFLDNEENEDILEDIVLTLTLFEDREMIEERLKTYAHLFDDKVMKQL
KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

>SEQ ID NO: 22; UGI domain
MTNLSDIIEKETGKQLVIQESILMLPEEVEEVIGNKPESDILVHTAYDES

TDENVMLLTSDAPEYKPWALVIQDSNGENKIKML

>SEQ ID NO: 42; NpuC-SP11-18-g3p
MIKIATRKYLGKQNVYDIGVERDHNFALKNGFIASNCFNVVPFYSHSAET

VESCLAKPHTENSFTNVWKDDKTLDRYANYEGCLWNATGVVVCTGDETQC

YGTWVPIGLAIPENEGGGSEGGGSEGGGSEGGGTKPPEYGDTPIPGYTYI

NPLDGTYPPGTEQNPANPNPSLEESQPLNTFMFQNNRFRNRQGALTVYTG

TVTQGTDPVKTYYQYTPVSSKAMYDAYWNGKFRDCAFHSGFNEDPFVCEY

QGQSSDLPQPPVNAGGGSGGGSGGGSEGGGSEGGGSEGGGSEGGGSGGGS

GSGDFDYEKMANANKGAMTENADENALQSDAKGKLDSVATDYGAAIDGFI

GDVSGLANGNGATGDFAGSNSQMAQVGDGDNSPLMNNFRQYLPSLPQSVE

CRPFVFGAGKPYEFSIDCDKINLFRGVFAFLLYVATFMYVFSTFANILRN

KES

---

What is claimed is:

1. A cytidine deaminase protein variant comprising an amino acid sequence that is at least 95% identical to the amino acid sequence of SEQ ID NO: 15 [rAPOBEC1], wherein the amino acid sequence of the cytidine deaminase protein variant includes at least three mutations at a position selected from the group consisting of R33, G45, N57, N65, Y75, T101, F113, A123, S149, A165, H166, T204, F205, and W224 of SEQ ID NO: 15 [rAPOBEC1], and wherein the cytidine deaminase protein variant has deaminase activity.

2. The cytidine deaminase protein variant of claim 1, wherein the amino acid sequence includes three or more of the following mutations: R33C, G45D, N57S, N65D, Y75H, T101I, F113C, F113R, A123E, S149Y, A165T H166N, T204P, F205S, or W224R.

3. The cytidine deaminase protein variant of claim 1, wherein the amino acid sequence of the protein does not comprise a mutation at position E63.

4. The cytidine deaminase protein variant of claim 1, wherein the amino acid sequence includes mutations at positions F113, A123, and F205.

5. The cytidine deaminase protein variant of claim 4, wherein the amino acid sequence includes the following mutations: F113C, A123E, and F205S.

6. The cytidine deaminase protein variant of claim 4 comprising the amino acid sequence set forth in SEQ ID NO: 16.

7. The cytidine deaminase protein variant of claim 1, wherein the amino acid sequence includes mutations at positions G45, Y75, F113, A123, H166, and F205.

8. The cytidine deaminase protein variant of claim 7, wherein the amino acid sequence includes the following mutations: G45D, Y75H, F113C, A123E, H166N, and F205S.

9. The cytidine deaminase protein variant of claim 7 comprising the amino acid sequence set forth in SEQ ID NO: 17.

10. The cytidine deaminase protein variant of claim 1, wherein the amino acid sequence includes mutations at positions F113, A123, A165, and F205.

11. The cytidine deaminase protein variant of claim 10, wherein the amino acid sequence includes the following mutations: F113C, A123E, A165T, and F205S.

12. The cytidine deaminase protein variant of claim 10 comprising the amino acid sequence set forth in SEQ ID NO: 19.

13. A fusion protein comprising: (i) a RNA-programmable nuclease; (ii) the cytidine deaminase protein variant of claim 1; and (iii) a uracil glycosylase inhibitor (UGI) domain.

14. The fusion protein of claim 13, wherein the RNA-programmable nuclease is a Cas9 domain comprising an amino acid sequence that is at least 85% identical to the amino acid sequence provided in SEQ ID NO: 20 or 21.

15. The fusion protein of claim 13, wherein the Cas9 domain is a Cas9 nickase domain that cuts a nucleotide target strand of a nucleotide duplex, wherein the nucleotide target strand is the strand that binds to a guide RNA (gRNA) of the Cas9 nickase domain.

16. The fusion protein of claim 13, wherein the UGI domain comprises a domain capable of inhibiting Uracil DNA Glycosylase (UDG) activity.

17. The fusion protein of claim 13, wherein the UGI domain comprises an amino acid sequence that is at least 85% identical to SEQ ID NO: 22.

18. A complex comprising the fusion protein of claim 13, and a guide RNA (gRNA) bound to the RNA-programmable nuclease of the fusion protein.

19. The complex of claim 18, wherein the gRNA is from 15-100 nucleotides long and comprises a sequence of at least 10 contiguous nucleotides that is complementary to a target sequence.

20. A fusion protein comprising: (i) a RNA-programmable nuclease, and (ii) the cytidine deaminase protein variant of claim 16.

21. The cytidine deaminase protein variant of claim 16, wherein the cytidine deaminase protein variant has increased soluble expression in a bacterial expression system relative to SEQ ID NO: 15.

\* \* \* \* \*

UNITED STATES PATENT AND TRADEMARK OFFICE
CERTIFICATE OF CORRECTION

PATENT NO. : 11,913,044 B2
APPLICATION NO. : 17/251276
DATED : February 27, 2024
INVENTOR(S) : David R. Liu et al.

It is certified that error appears in the above-identified patent and that said Letters Patent is hereby corrected as shown below:

In the Claims

In Claim 2, at Column 147, Line 63, the text: "T101I, F113C, F113R, A123E, S149Y, A165T H166N," should be replaced with: -- T101I, F113C, F113R, A123E, S149Y, A165T, H166N, --.

In Claim 20, at Column 150, Lines 16-18, the text: "A fusion protein comprising: (i) a RNA-programmable nuclease, and (ii) the cytidine deaminase protein variant of claim 16." should be replaced with: -- A fusion protein comprising: (i) a RNA-programmable nuclease, and (ii) the cytidine deaminase protein variant of claim 1. --.

In Claim 21, at Column 150, Lines 19-22, the text: "The cytidine deaminase protein variant of claim 16, wherein the cytidine deaminase protein variant has increased soluble expression in a bacterial expression system relative to SEQ ID NO: 15." should be replaced with: -- The cytidine deaminase protein variant of claim 1, wherein the cytidine deaminase protein variant has increased soluble expression in a bacterial expression system relative to SEQ ID NO: 15. --.

Signed and Sealed this
Fourteenth Day of May, 2024

Katherine Kelly Vidal
*Director of the United States Patent and Trademark Office*